(12) United States Patent
Johnston et al.

(10) Patent No.: US 6,583,121 B1
(45) Date of Patent: Jun. 24, 2003

(54) SYSTEM FOR THE IN VIVO DELIVERY AND EXPRESSION OF HETEROLOGOUS GENES IN THE BONE MARROW

(75) Inventors: Robert E. Johnston; Nancy L. Davis; Dennis A. Simpson, all of Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/367,764

(22) PCT Filed: Feb. 18, 1998

(86) PCT No.: PCT/US98/02945

§ 371 (c)(1),
(2), (4) Date: Nov. 12, 1999

(87) PCT Pub. No.: WO98/36779

PCT Pub. Date: Aug. 27, 1998

Related U.S. Application Data

(63) Continuation-in-part of application No. 08/801,263, filed on Feb. 19, 1997, now Pat. No. 5,811,407.

(51) Int. Cl.$^7$ .......................... A61K 48/00; C12N 15/64
(52) U.S. Cl. ..................................... 514/44; 435/320.1
(58) Field of Search ........................ 514/44; 435/320.1

(56) References Cited

U.S. PATENT DOCUMENTS

| | | | |
|---|---|---|---|
| 4,650,764 A | 3/1987 | Temin et al. | 435/240 |
| 5,091,309 A | 2/1992 | Schlesinger et al. | 435/69.1 |
| 5,185,440 A | 2/1993 | Davis et al. | 536/237 |
| 5,217,879 A | 6/1993 | Huang et al. | 435/69.1 |
| 5,505,947 A | 4/1996 | Johnston et al. | 424/218.1 |
| 5,639,650 A | 6/1997 | Johnston et al. | 435/236 |
| 5,643,576 A | 7/1997 | Johnston et al. | 424/199.1 |
| 5,739,026 A | 4/1998 | Garoff et al. | 435/240.2 |
| 5,789,245 A | 8/1998 | Dubensky, Jr. et al. | 435/320.1 |
| 5,792,462 A | 8/1998 | Johnston et al. | 424/199.1 |
| 5,814,482 A | 9/1998 | Dubensky, Jr. et al. | 435/69.3 |
| 5,843,723 A | 12/1998 | Dubensky, Jr. et al. | 435/69.3 |
| 6,156,304 A | 12/2000 | Glorioso et al. | 424/93.2 |

FOREIGN PATENT DOCUMENTS

| | | | |
|---|---|---|---|
| WO | WO92/10578 | 6/1992 | |
| WO | WO 95/07994 | 3/1995 | |
| WO | WO 95/27044 | 10/1995 | C12N/7/01 |
| WO | WO 95/31565 | 11/1995 | C12N/7/01 |
| WO | WO 96/17072 | 6/1996 | C12N/15/86 |
| WO | WO 96/37220 | 11/1996 | A61K/39/12 |
| WO | WO 96/37616 | 11/1996 | C12N/15/33 |
| WO | WO 97/38087 | 10/1997 | |

OTHER PUBLICATIONS

Bredenbeek et al.; Sindbis Virus Expression Vectors: Packaging of RNA Replicons by Using Defective Helper RNAs, *J. of Virology*, 67(11):6439–6446 (1993).

Corsini et al.; Efficiency of Transduction by Recombinant Sindbis Replicon Virus Varies Among Cell Lines, Including Mosquito Cells and Rat Sensory Neurons, BioTechniques, vol. 21, No. 3, p. 492–497, Sep. 1996.

Davis et al.; Attenuating Mutations in the E2 Glycoprotein Gene of Venezuelan Equine Encephalitis Virus: Construction of Single and Multiple Mutants in a Full–Length cDNA Clone, *Virology*, 183:20–31 (1991).

Davis et al.; Attenuated Mutants of Venezuelan Equine Encephalitis Virus Containing Lethal Mutations in the PE2 Cleavage Signal Combined with a Second–Site Suppressor Mutation in E1, *Virology*, 212:102–110 (1995).

Davis et al; A Genetically Engineered Live Virus Vaccine for Venezuelan Equine Encephalitis ( Abstract N404), *J. Cell Biochemistry*, Supplement 0 No. 17 Part D:79 (1993).

Dubensky, Jr. et al.; Sindbis Virus DNA–Based Expression Vectors: Utility for In Vitro and In Vivo Gene Transfer, Journal of Virology, 70:(508–519) Jan. 1996.

Frolov et al.: Alphavirus–based expression vectors: Strategies and applications, *Proc. Natl. Acad. Sci. USA*, 93:11371–11377 (1996).

Frolova et al.; Packaging Signals in Alphaviruses, Journal of Virology, 71:(248–258) Jan. 1997.

Grieder et al.; Specific Restrictions in the Progression of Venezuelan Equine Encephalitis Virus–Induced Disease Resulting from Single Amino Acid Changes in the Glycoproteins, Virology 206, p. 994–1006, 1995.

Hahn et al., Infectious Sindbis virus transient expression vectors for studying antigen processing and presentation, *Proc. Natl. Acad. Sci. USA* 89:2679–2683 (1992).

Lemm et al.; Polypeptide requirements for assembly of functional Sindbis virus replication complexes: a model for the temporal regulation of minus–and plus–strand RNA, The EMBO Journal, vol. 13, No. 12, p. 2925–2934, 1994.

Liljeström et al.; A New Generation of Animal Cell Expression Vectors Based on the Semliki Forest Virus Replicon, *Bio/Technology, Research*, 9:1356–1361 (1991).

Liljeström; Alphavirus Vectors for Gene Delivery, OECD Documents, Gene Delivery Systems, 1996, p. 109–118, XP002093351.

(List continued on next page.)

*Primary Examiner*—Marianne P. Allen
(74) *Attorney, Agent, or Firm*—Myers Bigel Sibley & Sajovec, P.A.

(57) ABSTRACT

The present invention provides a method of delivering immunogenic or therapeutic proteins to bone marrow cells using alphavirus vectors. The alphavirus vectors disclosed herein target specifically to bone marrow tissue, and viral genomes persist in bone marrow for at least three months post-infection. No or very low levels of virus were detected in quadricep, brain, and sera of treated animals. The sequence of a consensus Sindbis cDNA clone, pTR339, and infectious RNA transcripts, infectious virus particles, and pharmaceutical formulations derived therefrom are also disclosed. The sequence of the genomic RNA of the Girdwood S.A. virus, and cDNA clones, infectious RNA transcripts, infectious virus particles, and pharmaceutical formulations derived therefrom are also disclosed.

53 Claims, No Drawings

OTHER PUBLICATIONS

Liljeström; Alphavirus Expression Systems, *Current Opinion in Biotechnology*, 5:(495–500) 1994.

London et al., Infectious enveloped RNA virus antigenic chimeras, *Proc. Natl. Acad. Sci. USA*, 89:207–211 (1992).

McKnight et al.; Deduced Consensus Sequence of Sindbis Virus Strain AR339: Mutations Contained in Laboratory Strains Which Affect Cell Culture and In Vivo Phenotyples, *J. of Virology*, 70(3):1981–1989 (1996).

Morgenstern et al.; Advanced mammalian gene transfer: high titre retroviral vectors wit multiple drug selection markers and a complementary helper–free packaging cell line, *Nucleic Acids Research*, 18(12):3587–3596 (1990).

Orkin et al.; Report and Recommendations of the Panel to Assess the NIH Investment in Research on Gene Therapy, pp. 1–41 (1995).

Polo et al.; Attenuating Mutations in Glycoproteins E1 and E2 of Sindbis Virus Produce a Highly Attenuated Strain When Combined In Vitro, *J. of Virology*, 64(9):4438–4444 (1990).

Russell et al.; Sindbis Virus Mutations Which Coordinately Affect Glycoprotein Processing, Penetration, and Virulence in Mice, Journal of Virology, vol. 63, No. 4, p. 1619–1629, Apr. 1989.

Schoepp et al.; Directed Mutagenesis of a Sindbis Virus Pathogenesis Site, *Virology*, 193:149–159 (1993).

Simpson et al.; Sindbis–like Virus Isolate Girdwood S.A., Complete Genome, EMBL Database, Accession No. U38304, Jan. 3, 1996.

Simpson et al.; Complete Nucleotide Sequence and Full–Lenght cDNA Clone of S.A.AR86, a South African Alphavirus Related to Sindbis, *Virology*, 222(Article No. 445):464–469 (1996).

Sindbis Virus (HRSP and Wild–Type Strains) Complete Genome, EMBL Database, Accession No. J02363, J02364, J20366, J20367 and V00073, Jul. 3, 1991.

Strauss et al.; The Alphaviruses: Gene Expression, Replication, and Evolution, *Biological Reviews*, 58(3):491–562 (1994).

Suomalainen et al.; Spike Protein–Nucleocapsid Interactions Drive the Budding of Alphavirus, *J. of Virology* 66(8):4737–4747 (1992).

L. Ye Bulychyov, et al. "Disease Course in Guniea Pigs After Aerogenous Infection WIth Venezuelan Equine Encaphalomyeitis Virus." English Abstract attached. 1995.

D.K. Lvov, et al. ""Karshi Virus, a New Flavivirus (Togaviridae) Isolated ftrom Ornithodoros Papillipes (Birula, 1895) Ticks in Uzbek S.S.R."*Archives of Virolog*. vol. 50, pp. 29–36, 1976.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 11663 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 60..7559

(ix) FEATURE:
      (A) NAME/KEY: CDS
      (B) LOCATION: 7608..11342

(xi) SEQUENCE DESCRIPTION: SEQ ID NO:1:

```
ATTGGCGGCG TAGTACACAC TATTGAATCA AACAGCCGAC CAATTGCACT ACCATCACA         59

ATG GAG AAG CCA GTA GTT AAC GTA GAC GTA GAC CCT CAG AGT CCG TTT        107
Met Glu Lys Pro Val Val Asn Val Asp Val Asp Pro Gln Ser Pro Phe
  1               5                  10                  15

GTC GTG CAA CTG CAA AAG AGC TTC CCG CAA TTT GAG GTA GTA GCA CAG        155
Val Val Gln Leu Gln Lys Ser Phe Pro Gln Phe Glu Val Val Ala Gln
```

-continued

```
                20                      25                      30
CAG GTC ACT CCA AAT GAC CAT GCT AAT GCC AGA GCA TTT TCG CAT CTG       203
Gln Val Thr Pro Asn Asp His Ala Asn Ala Arg Ala Phe Ser His Leu
            35                      40                      45

GCC AGT AAA CTA ATC GAG CTG GAG GTT CCT ACC ACA GCG ACG ATT TTG       251
Ala Ser Lys Leu Ile Glu Leu Glu Val Pro Thr Thr Ala Thr Ile Leu
        50                      55                      60

GAC ATA GGC AGC GCA CCG GCT CGT AGA ATG TTT TCC GAG CAC CAG TAC       299
Asp Ile Gly Ser Ala Pro Ala Arg Arg Met Phe Ser Glu His Gln Tyr
65                      70                      75                      80

CAT TGC GTT TGC CCC ATG CGT AGT CCA GAA GAC CCG GAC CGC ATG ATG       347
His Cys Val Cys Pro Met Arg Ser Pro Glu Asp Pro Asp Arg Met Met
                    85                      90                      95

AAA TAT GCC AGC AAA CTG GCG GAA AAA GCA TGT AAG ATT ACA AAC AAG       395
Lys Tyr Ala Ser Lys Leu Ala Glu Lys Ala Cys Lys Ile Thr Asn Lys
                100                     105                     110

AAC TTG CAT GAG AAG ATC AAG GAC CTC CGG ACC GTA CTT GAT ACA CCG       443
Asn Leu His Glu Lys Ile Lys Asp Leu Arg Thr Val Leu Asp Thr Pro
            115                     120                     125

GAT GCT GAA ACG CCA TCA CTC TGC TTC CAC AAC GAT GTT ACC TGC AAC       491
Asp Ala Glu Thr Pro Ser Leu Cys Phe His Asn Asp Val Thr Cys Asn
130                     135                     140

ACG CGT GCC GAG TAC TCC GTC ATG CAG GAC GTG TAC ATC AAC GCT CCC       539
Thr Arg Ala Glu Tyr Ser Val Met Gln Asp Val Tyr Ile Asn Ala Pro
145                     150                     155                     160

GGA ACT ATT TAC CAC CAG GCT ATG AAA GGC GTG CGG ACC CTG TAC TGG       587
Gly Thr Ile Tyr His Gln Ala Met Lys Gly Val Arg Thr Leu Tyr Trp
                    165                     170                     175

ATT GGC TTC GAC ACC ACC CAG TTC ATG TTC TCG GCT ATG GCA GGT TCG       635
Ile Gly Phe Asp Thr Thr Gln Phe Met Phe Ser Ala Met Ala Gly Ser
                180                     185                     190

TAC CCT GCA TAC AAC ACC AAC TGG GCC GAC GAA AAA GTC CTT GAA GCG       683
Tyr Pro Ala Tyr Asn Thr Asn Trp Ala Asp Glu Lys Val Leu Glu Ala
            195                     200                     205

CGT AAC ATC GGA CTC TGC AGC ACA AAG CTG AGT GAA GGC AGG ACA GGA       731
Arg Asn Ile Gly Leu Cys Ser Thr Lys Leu Ser Glu Gly Arg Thr Gly
        210                     215                     220

AAG TTG TCG ATA ATG AGG AAG AAG GAG TTG AAG CCC GGG TCA CGG GTT       779
Lys Leu Ser Ile Met Arg Lys Lys Glu Leu Lys Pro Gly Ser Arg Val
225                     230                     235                     240

TAT TTC TCC GTT GGA TCG ACA CTT TAC CCA GAA CAC AGA GCC AGC TTG       827
Tyr Phe Ser Val Gly Ser Thr Leu Tyr Pro Glu His Arg Ala Ser Leu
                    245                     250                     255

CAG AGC TGG CAT CTT CCA TCG GTG TTC CAC TTG AAA GGA AAG CAG TCG       875
Gln Ser Trp His Leu Pro Ser Val Phe His Leu Lys Gly Lys Gln Ser
                260                     265                     270

TAC ACT TGC CGC TGT GAT ACA GTG GTG AGC TGC GAA GGC TAC GTA GTG       923
Tyr Thr Cys Arg Cys Asp Thr Val Val Ser Cys Glu Gly Tyr Val Val
            275                     280                     285

AAG AAA ATC ACC ATC AGT CCC GGG ATC ACG GGA GAA ACC GTG GGA TAC       971
Lys Lys Ile Thr Ile Ser Pro Gly Ile Thr Gly Glu Thr Val Gly Tyr
        290                     295                     300

GCG GTT ACA AAC AAT AGC GAG GGC TTC TTG CTA TGC AAA GTT ACC GAT      1019
Ala Val Thr Asn Asn Ser Glu Gly Phe Leu Leu Cys Lys Val Thr Asp
305                     310                     315                     320

ACA GTA AAA GGA GAA CGG GTA TCG TTC CCC GTG TGC ACG TAT ATC CCG      1067
Thr Val Lys Gly Glu Arg Val Ser Phe Pro Val Cys Thr Tyr Ile Pro
                    325                     330                     335

GCC ACC ATA TGC GAT CAG ATG ACC GGC ATA ATG GCC ACG GAT ATC TCA      1115
```

```
              Ala Thr Ile Cys Asp Gln Met Thr Gly Ile Met Ala Thr Asp Ile Ser
                          340                 345                 350

CCT GAC GAT GCA CAA AAA CTT CTG GTT GGG CTC AAC CAG CGA ATC GTC          1163
Pro Asp Asp Ala Gln Lys Leu Leu Val Gly Leu Asn Gln Arg Ile Val
                355                 360                 365

ATT AAC GGT AAG ACT AAC AGG AAC ACC AAT ACC ATG CAA AAT TAC CTT          1211
Ile Asn Gly Lys Thr Asn Arg Asn Thr Asn Thr Met Gln Asn Tyr Leu
    370                 375                 380

CTG CCA ATC ATT GCA CAA GGG TTC AGC AAA TGG GCC AAG GAG CGC AAA          1259
Leu Pro Ile Ile Ala Gln Gly Phe Ser Lys Trp Ala Lys Glu Arg Lys
385                 390                 395                 400

GAA GAT CTT GAC AAT GAA AAA ATG CTG GGC ACC AGA GAG CGC AAG CTT          1307
Glu Asp Leu Asp Asn Glu Lys Met Leu Gly Thr Arg Glu Arg Lys Leu
                405                 410                 415

ACA TAT GGC TGC TTG TGG GCG TTT CGC ACT AAG AAA GTG CAC TCG TTC          1355
Thr Tyr Gly Cys Leu Trp Ala Phe Arg Thr Lys Lys Val His Ser Phe
                420                 425                 430

TAT CGC CCA CCT GGA ACG CAG ACC ATC GTA AAA GTC CCA GCC TCT TTT          1403
Tyr Arg Pro Pro Gly Thr Gln Thr Ile Val Lys Val Pro Ala Ser Phe
        435                 440                 445

AGC GCT TTC CCC ATG TCA TCC GTA TGG ACT ACC TCT TTG CCC ATG TCG          1451
Ser Ala Phe Pro Met Ser Ser Val Trp Thr Thr Ser Leu Pro Met Ser
    450                 455                 460

CTG AGG CAG AAG ATG AAA TTG GCA TTA CAA CCA AAG AAG GAG GAA AAA          1499
Leu Arg Gln Lys Met Lys Leu Ala Leu Gln Pro Lys Lys Glu Glu Lys
465                 470                 475                 480

CTG CTG CAA GTC CCG GAG GAA TTA GTT ATG GAG GCC AAG GCT GCT TTC          1547
Leu Leu Gln Val Pro Glu Glu Leu Val Met Glu Ala Lys Ala Ala Phe
                485                 490                 495

GAG GAT GCT CAG GAG GAA TCC AGA GCG GAG AAG CTC CGA GAA GCA CTC          1595
Glu Asp Ala Gln Glu Glu Ser Arg Ala Glu Lys Leu Arg Glu Ala Leu
                500                 505                 510

CCA CCA TTA GTG GCA GAC AAA GGT ATC GAG GCA GCT GCG GAA GTT GTC          1643
Pro Pro Leu Val Ala Asp Lys Gly Ile Glu Ala Ala Ala Glu Val Val
            515                 520                 525

TGC GAA GTG GAG GGG CTC CAG GCG GAC ACC GGA GCA GCA CTC GTC GAA          1691
Cys Glu Val Glu Gly Leu Gln Ala Asp Thr Gly Ala Ala Leu Val Glu
        530                 535                 540

ACC CCG CGC GGT CAT GTA AGG ATA ATA CCT CAA GCA AAT GAC CGT ATG          1739
Thr Pro Arg Gly His Val Arg Ile Ile Pro Gln Ala Asn Asp Arg Met
545                 550                 555                 560

ATC GGA CAG TAT ATC GTT GTC TCG CCG ATC TCT GTG CTG AAG AAC GCT          1787
Ile Gly Gln Tyr Ile Val Val Ser Pro Ile Ser Val Leu Lys Asn Ala
                565                 570                 575

AAA CTC GCA CCA GCA CAC CCG CTA GCA GAC CAG GTT AAG ATC ATA ACG          1835
Lys Leu Ala Pro Ala His Pro Leu Ala Asp Gln Val Lys Ile Ile Thr
                580                 585                 590

CAC TCC GGA AGA TCA GGA AGG TAT GCA GTC GAA CCA TAC GAC GCT AAA          1883
His Ser Gly Arg Ser Gly Arg Tyr Ala Val Glu Pro Tyr Asp Ala Lys
            595                 600                 605

GTA CTG ATG CCA GCA GGA AGT GCC GTA CCA TGG CCA GAA TTC TTA GCA          1931
Val Leu Met Pro Ala Gly Ser Ala Val Pro Trp Pro Glu Phe Leu Ala
        610                 615                 620

CTG AGT GAG AGC GCC ACG CTT GTG TAC AAC GAA AGA GAG TTT GTG AAC          1979
Leu Ser Glu Ser Ala Thr Leu Val Tyr Asn Glu Arg Glu Phe Val Asn
625                 630                 635                 640

CGC AAG CTG TAC CAT ATT GCC ATG CAC GGT CCC GCT AAG AAT ACA GAA          2027
Arg Lys Leu Tyr His Ile Ala Met His Gly Pro Ala Lys Asn Thr Glu
                645                 650                 655
```

```
GAG GAG CAG TAC AAG GTT ACA AAG GCA GAG CTC GCA GAA ACA GAG TAC    2075
Glu Glu Gln Tyr Lys Val Thr Lys Ala Glu Leu Ala Glu Thr Glu Tyr
            660                 665                 670

GTG TTT GAC GTG GAC AAG AAG CGA TGC GTT AAG AAG GAA GAA GCC TCA    2123
Val Phe Asp Val Asp Lys Lys Arg Cys Val Lys Lys Glu Glu Ala Ser
                675                 680                 685

GGA CTT GTC CTT TCG GGA GAA CTG ACC AAC CCG CCC TAT CAC GAA CTA    2171
Gly Leu Val Leu Ser Gly Glu Leu Thr Asn Pro Pro Tyr His Glu Leu
        690                 695                 700

GCT CTT GAG GGA CTG AAG ACT CGA CCC GCG GTC CCG TAC AAG GTT GAA    2219
Ala Leu Glu Gly Leu Lys Thr Arg Pro Ala Val Pro Tyr Lys Val Glu
705                 710                 715                 720

ACA ATA GGA GTG ATA GGC ACA CCA GGA TCG GGC AAG TCA GCT ATC ATC    2267
Thr Ile Gly Val Ile Gly Thr Pro Gly Ser Gly Lys Ser Ala Ile Ile
            725                 730                 735

AAG TCA ACT GTC ACG GCA CGT GAT CTT GTT ACC AGC GGA AAG AAA GAA    2315
Lys Ser Thr Val Thr Ala Arg Asp Leu Val Thr Ser Gly Lys Lys Glu
                740                 745                 750

AAC TGC CGC GAA ATT GAG GCC GAC GTG CTA CGG CTG AGG GGC ATG CAG    2363
Asn Cys Arg Glu Ile Glu Ala Asp Val Leu Arg Leu Arg Gly Met Gln
        755                 760                 765

ATC ACG TCG AAG ACA GTG GAT TCG GTT ATG CTC AAC GGA TGC CAC AAA    2411
Ile Thr Ser Lys Thr Val Asp Ser Val Met Leu Asn Gly Cys His Lys
770                 775                 780

GCC GTA GAA GTG CTG TAT GTT GAC GAA GCG TTC CGG TGC CAC GCA GGA    2459
Ala Val Glu Val Leu Tyr Val Asp Glu Ala Phe Arg Cys His Ala Gly
785                 790                 795                 800

GCA CTA CTT GCC TTG ATT GCA ATC GTC AGA CCC CGT AAG AAG GTA GTA    2507
Ala Leu Leu Ala Leu Ile Ala Ile Val Arg Pro Arg Lys Lys Val Val
            805                 810                 815

CTA TGC GGA GAC CCT AAG CAA TGC GGA TTC TTC AAC ATG ATG CAA CTA    2555
Leu Cys Gly Asp Pro Lys Gln Cys Gly Phe Phe Asn Met Met Gln Leu
                820                 825                 830

AAG GTA CAT TTC AAC CAC CCT GAA AAA GAC ATA TGT ACC AAG ACA TTC    2603
Lys Val His Phe Asn His Pro Glu Lys Asp Ile Cys Thr Lys Thr Phe
        835                 840                 845

TAC AAG TTT ATC TCC CGA CGT TGC ACA CAG CCA GTC ACG GCT ATT GTA    2651
Tyr Lys Phe Ile Ser Arg Arg Cys Thr Gln Pro Val Thr Ala Ile Val
850                 855                 860

TCG ACA CTG CAT TAC GAT GGA AAA ATG AAA ACC ACA AAC CCG TGC AAG    2699
Ser Thr Leu His Tyr Asp Gly Lys Met Lys Thr Thr Asn Pro Cys Lys
865                 870                 875                 880

AAG AAC ATC GAA ATC GAC ATT ACA GGG GCC ACG AAG CCG AAG CCA GGG    2747
Lys Asn Ile Glu Ile Asp Ile Thr Gly Ala Thr Lys Pro Lys Pro Gly
            885                 890                 895

GAC ATC ATC CTG ACA TGT TTC CGC GGG TGG GTT AAG CAA CTG CAA ATC    2795
Asp Ile Ile Leu Thr Cys Phe Arg Gly Trp Val Lys Gln Leu Gln Ile
                900                 905                 910

GAC TAT CCC GGA CAT GAG GTA ATG ACA GCC GCG GCC TCA CAA GGG CTA    2843
Asp Tyr Pro Gly His Glu Val Met Thr Ala Ala Ala Ser Gln Gly Leu
        915                 920                 925

ACC AGA AAA GGA GTA TAT GCC GTC CGG CAA AAA GTC AAT GAA AAC CCG    2891
Thr Arg Lys Gly Val Tyr Ala Val Arg Gln Lys Val Asn Glu Asn Pro
930                 935                 940

CTG TAC GCG ATC ACA TCA GAG CAT GTG AAC GTG TTG CTC ACC CGC ACT    2939
Leu Tyr Ala Ile Thr Ser Glu His Val Asn Val Leu Leu Thr Arg Thr
945                 950                 955                 960

GAG GAC AGG CTA GTA TGG AAA ACT TTA CAG GGC GAC CCA TGG ATT AAG    2987
Glu Asp Arg Leu Val Trp Lys Thr Leu Gln Gly Asp Pro Trp Ile Lys
            965                 970                 975
```

```
CAG CTC ACT AAC GTA CCT AAA GGA AAT TTT CAG GCC ACC ATC GAG GAC    3035
Gln Leu Thr Asn Val Pro Lys Gly Asn Phe Gln Ala Thr Ile Glu Asp
            980                 985                 990

TGG GAA GCT GAA CAC AAG GGA ATA ATT GCT GCG ATA AAC AGT CCC GCT    3083
Trp Glu Ala Glu His Lys Gly Ile Ile Ala Ala Ile Asn Ser Pro Ala
            995                 1000                1005

CCC CGT ACC AAT CCG TTC AGC TGC AAG ACT AAC GTT TGC TGG GCG AAA    3131
Pro Arg Thr Asn Pro Phe Ser Cys Lys Thr Asn Val Cys Trp Ala Lys
            1010                1015                1020

GCA CTG GAA CCG ATA CTG GCC ACG GCC GGT ATC GTA CTT ACC GGT TGC    3179
Ala Leu Glu Pro Ile Leu Ala Thr Ala Gly Ile Val Leu Thr Gly Cys
1025                1030                1035                1040

CAG TGG AGC GAG CTG TTC CCA CAG TTT GCG GAT GAC AAA CCA CAC TCG    3227
Gln Trp Ser Glu Leu Phe Pro Gln Phe Ala Asp Asp Lys Pro His Ser
            1045                1050                1055

GCC ATC TAC GCC TTA GAC GTA ATT TGC ATT AAG TTT TTC GGC ATG GAC    3275
Ala Ile Tyr Ala Leu Asp Val Ile Cys Ile Lys Phe Phe Gly Met Asp
            1060                1065                1070

TTG ACA AGC GGG CTG TTT TCC AAA CAG AGC ATC CCG TTA ACG TAC CAT    3323
Leu Thr Ser Gly Leu Phe Ser Lys Gln Ser Ile Pro Leu Thr Tyr His
            1075                1080                1085

CCT GCC GAC TCA GCG AGG CCA GTA GCT CAT TGG GAC AAC AGC CCA GGA    3371
Pro Ala Asp Ser Ala Arg Pro Val Ala His Trp Asp Asn Ser Pro Gly
            1090                1095                1100

ACA CGC AAG TAT GGG TAC GAT CAC GCC GTT GCC GCC GAA CTC TCC CGT    3419
Thr Arg Lys Tyr Gly Tyr Asp His Ala Val Ala Ala Glu Leu Ser Arg
1105                1110                1115                1120

AGA TTT CCG GTG TTC CAG CTA GCT GGG AAA GGC ACA CAG CTT GAT TTG    3467
Arg Phe Pro Val Phe Gln Leu Ala Gly Lys Gly Thr Gln Leu Asp Leu
            1125                1130                1135

CAG ACG GGC AGA ACT AGA GTT ATC TCT GCA CAG CAT AAC TTG GTC CCA    3515
Gln Thr Gly Arg Thr Arg Val Ile Ser Ala Gln His Asn Leu Val Pro
            1140                1145                1150

GTG AAC CGC AAT CTC CCT CAC GCC TTA GTC CCC GAG CAC AAG GAG AAA    3563
Val Asn Arg Asn Leu Pro His Ala Leu Val Pro Glu His Lys Glu Lys
            1155                1160                1165

CAA CCC GGC CCG GTC GAA AAA TTC TTG AGC CAG TTC AAA CAC CAC TCC    3611
Gln Pro Gly Pro Val Glu Lys Phe Leu Ser Gln Phe Lys His His Ser
    1170                1175                1180

GTA CTT GTG ATC TCA GAG AAA AAA ATT GAA GCT CCC CAC AAG AGA ATC    3659
Val Leu Val Ile Ser Glu Lys Lys Ile Glu Ala Pro His Lys Arg Ile
1185                1190                1195                1200

GAA TGG ATC GCC CCG ATT GGC ATA GCC GGC GCA GAT AAG AAC TAC AAC    3707
Glu Trp Ile Ala Pro Ile Gly Ile Ala Gly Ala Asp Lys Asn Tyr Asn
            1205                1210                1215

CTG GCT TTC GGG TTT CCG CCG CAG GCA CGG TAC GAC CTG GTG TTC ATC    3755
Leu Ala Phe Gly Phe Pro Pro Gln Ala Arg Tyr Asp Leu Val Phe Ile
            1220                1225                1230

AAT ATT GGA ACT AAA TAC AGA AAC CAT CAC TTT CAA CAG TGC GAA GAC    3803
Asn Ile Gly Thr Lys Tyr Arg Asn His His Phe Gln Gln Cys Glu Asp
            1235                1240                1245

CAC GCG GCG ACC TTG AAA ACC CTT TCG CGT TCG GCC CTG AAC TGC CTT    3851
His Ala Ala Thr Leu Lys Thr Leu Ser Arg Ser Ala Leu Asn Cys Leu
            1250                1255                1260

AAC CCC GGA GGC ACC CTC GTG GTG AAG TCC TAC GGT TAC GCC GAC CGC    3899
Asn Pro Gly Gly Thr Leu Val Val Lys Ser Tyr Gly Tyr Ala Asp Arg
1265                1270                1275                1280

AAT AGT GAG GAC GTA GTC ACC GCT CTT GCC AGA AAA TTT GTC AGA GTG    3947
Asn Ser Glu Asp Val Val Thr Ala Leu Ala Arg Lys Phe Val Arg Val
```

-continued

```
            1285                    1290                    1295
TCT GCA GCG AGG CCA GAG TGC GTC TCA AGC AAT ACA GAA ATG TAC CTG        3995
Ser Ala Ala Arg Pro Glu Cys Val Ser Ser Asn Thr Glu Met Tyr Leu
            1300                    1305                    1310

ATT TTC CGA CAA CTA GAC AAC AGC CGC ACA CGA CAA TTC ACC CCG CAT        4043
Ile Phe Arg Gln Leu Asp Asn Ser Arg Thr Arg Gln Phe Thr Pro His
            1315                    1320                    1325

CAT TTG AAT TGT GTG ATT TCG TCC GTG TAC GAG GGT ACA AGA GAC GGA        4091
His Leu Asn Cys Val Ile Ser Ser Val Tyr Glu Gly Thr Arg Asp Gly
            1330                    1335                    1340

GTT GGA GCC GCA CCG TCG TAC CGT ACT AAA AGG GAG AAC ATT GCT GAT        4139
Val Gly Ala Ala Pro Ser Tyr Arg Thr Lys Arg Glu Asn Ile Ala Asp
1345                    1350                    1355                    1360

TGT CAA GAG GAA GCA GTT GTC AAT GCA GCC AAT CCA CTG GGC AGA CCA        4187
Cys Gln Glu Glu Ala Val Val Asn Ala Ala Asn Pro Leu Gly Arg Pro
            1365                    1370                    1375

GGA GAA GGA GTC TGC CGT GCC ATC TAT AAA CGT TGG CCG AAC AGT TTC        4235
Gly Glu Gly Val Cys Arg Ala Ile Tyr Lys Arg Trp Pro Asn Ser Phe
            1380                    1385                    1390

ACC GAT TCA GCC ACA GAG ACA GGT ACC GCA AAA CTG ACT GTG TGC CAA        4283
Thr Asp Ser Ala Thr Glu Thr Gly Thr Ala Lys Leu Thr Val Cys Gln
            1395                    1400                    1405

GGA AAG AAA GTG ATC CAC GCG GTT GGC CCT GAT TTC CGG AAA CAC CCA        4331
Gly Lys Lys Val Ile His Ala Val Gly Pro Asp Phe Arg Lys His Pro
            1410                    1415                    1420

GAG GCA GAA GCC CTG AAA TTG CTG CAA AAC GCC TAC CAT GCA GTG GCA        4379
Glu Ala Glu Ala Leu Lys Leu Leu Gln Asn Ala Tyr His Ala Val Ala
1425                    1430                    1435                    1440

GAC TTA GTA AAT GAA CAT AAT ATC AAG TCT GTC GCC ATC CCA CTG CTA        4427
Asp Leu Val Asn Glu His Asn Ile Lys Ser Val Ala Ile Pro Leu Leu
            1445                    1450                    1455

TCT ACA GGC ATT TAC GCA GCC GGA AAA GAC CGC CTT GAG GTA TCA CTT        4475
Ser Thr Gly Ile Tyr Ala Ala Gly Lys Asp Arg Leu Glu Val Ser Leu
            1460                    1465                    1470

AAC TGC TTG ACA ACC GCG CTA GAC AGA ACT GAT GCG GAC GTA ACC ATC        4523
Asn Cys Leu Thr Thr Ala Leu Asp Arg Thr Asp Ala Asp Val Thr Ile
            1475                    1480                    1485

TAC TGC CTG GAT AAG AAG TGG AAG GAA AGA ATC GAC GCG GTG CTC CAA        4571
Tyr Cys Leu Asp Lys Lys Trp Lys Glu Arg Ile Asp Ala Val Leu Gln
            1490                    1495                    1500

CTT AAG GAG TCT GTA ACT GAG CTG AAG GAT GAG GAT ATG GAG ATC GAC        4619
Leu Lys Glu Ser Val Thr Glu Leu Lys Asp Glu Asp Met Glu Ile Asp
1505                    1510                    1515                    1520

GAC GAG TTA GTA TGG ATC CAT CCG GAC AGT TGC CTG AAG GGA AGA AAG        4667
Asp Glu Leu Val Trp Ile His Pro Asp Ser Cys Leu Lys Gly Arg Lys
            1525                    1530                    1535

GGA TTC AGT ACT ACA AAA GGA AAG TTG TAT TCG TAC TTT GAA GGC ACC        4715
Gly Phe Ser Thr Thr Lys Gly Lys Leu Tyr Ser Tyr Phe Glu Gly Thr
            1540                    1545                    1550

AAA TTC CAT CAA GCA GCA AAA GAT ATG GCG GAG ATA AAG GTC CTG TTC        4763
Lys Phe His Gln Ala Ala Lys Asp Met Ala Glu Ile Lys Val Leu Phe
            1555                    1560                    1565

CCA AAT GAC CAG GAA AGC AAC GAA CAA CTG TGT GCC TAC ATA TTG GGG        4811
Pro Asn Asp Gln Glu Ser Asn Glu Gln Leu Cys Ala Tyr Ile Leu Gly
            1570                    1575                    1580

GAG ACC ATG GAA GCA ATC CGC GAA AAA TGC CCG GTC GAC CAC AAC CCG        4859
Glu Thr Met Glu Ala Ile Arg Glu Lys Cys Pro Val Asp His Asn Pro
1585                    1590                    1595                    1600

TCG TCT AGC CCG CCA AAA ACG CTG CCG TGC CTC TGT ATG TAT GCC ATG        4907
```

```
Ser Ser Ser Pro Pro Lys Thr Leu Pro Cys Leu Cys Met Tyr Ala Met
            1605            1610                1615

ACG CCA GAA AGG GTC CAC AGA CTC AGA AGC AAT AAC GTC AAA GAA GTT        4955
Thr Pro Glu Arg Val His Arg Leu Arg Ser Asn Asn Val Lys Glu Val
        1620                1625                1630

ACA GTA TGC TCC TCC ACC CCC CTT CCA AAG TAC AAA ATC AAG AAT GTT        5003
Thr Val Cys Ser Ser Thr Pro Leu Pro Lys Tyr Lys Ile Lys Asn Val
1635                1640                1645

CAG AAG GTT CAG TGC ACA AAA GTA GTC CTG TTT AAC CCG CAT ACC CCC        5051
Gln Lys Val Gln Cys Thr Lys Val Val Leu Phe Asn Pro His Thr Pro
    1650                1655                1660

GCA TTC GTT CCC GCC CGT AAG TAC ATA GAA GCA CCA GAA CAG CCT GCA        5099
Ala Phe Val Pro Ala Arg Lys Tyr Ile Glu Ala Pro Glu Gln Pro Ala
1665                1670                1675                1680

GCT CCG CCT GCA CAG GCC GAG GAG GCC CCC GGA GTT GTA GCG ACA CCA        5147
Ala Pro Pro Ala Gln Ala Glu Glu Ala Pro Gly Val Val Ala Thr Pro
            1685                1690                1695

ACA CCA CCT GCA GCT GAT AAC ACC TCG CTT GAT GTC ACG GAC ATC TCA        5195
Thr Pro Pro Ala Ala Asp Asn Thr Ser Leu Asp Val Thr Asp Ile Ser
                1700                1705                1710

CTG GAC ATG GAA GAC AGT AGC GAA GGC TCA CTC TTT TCG AGC TTT AGC        5243
Leu Asp Met Glu Asp Ser Ser Glu Gly Ser Leu Phe Ser Ser Phe Ser
        1715                1720                1725

GGA TCG GAC AAC TAC CGA AGG CAG GTG GTG GTG GCT GAC GTC CAT GCC        5291
Gly Ser Asp Asn Tyr Arg Arg Gln Val Val Val Ala Asp Val His Ala
    1730                1735                1740

GTC CAA GAG CCT GCC CCT GTT CCA CCG CCA AGG CTA AAG AAG ATG GCC        5339
Val Gln Glu Pro Ala Pro Val Pro Pro Pro Arg Leu Lys Lys Met Ala
1745                1750                1755                1760

CGC CTG GCA GCG GCA AGA ATG CAG GAA GAG CCA ACT CCA CCG GCA AGC        5387
Arg Leu Ala Ala Ala Arg Met Gln Glu Glu Pro Thr Pro Pro Ala Ser
            1765                1770                1775

ACC AGC TCT GCG GAC GAG TCC CTT CAC CTT TCT TTT GAT GGG GTA TCT        5435
Thr Ser Ser Ala Asp Glu Ser Leu His Leu Ser Phe Asp Gly Val Ser
                1780                1785                1790

ATA TCC TTC GGA TCC CTT TTC GAC GGA GAG ATG GCC CGC TTG GCA GCG        5483
Ile Ser Phe Gly Ser Leu Phe Asp Gly Glu Met Ala Arg Leu Ala Ala
        1795                1800                1805

GCA CAA CCC CCG GCA AGT ACA TGC CCT ACG GAT GTG CCT ATG TCT TTC        5531
Ala Gln Pro Pro Ala Ser Thr Cys Pro Thr Asp Val Pro Met Ser Phe
    1810                1815                1820

GGA TCG TTT TCC GAC GGA GAG ATT GAG GAG TTG AGC CGC AGA GTA ACC        5579
Gly Ser Phe Ser Asp Gly Glu Ile Glu Glu Leu Ser Arg Arg Val Thr
1825                1830                1835                1840

GAG TCG GAG CCC GTC CTG TTT GGG TCA TTT GAA CCG GGC GAA GTG AAC        5627
Glu Ser Glu Pro Val Leu Phe Gly Ser Phe Glu Pro Gly Glu Val Asn
            1845                1850                1855

TCA ATT ATA TCG TCC CGA TCA GCC GTA TCT TTT CCA CCA CGC AAG CAG        5675
Ser Ile Ile Ser Ser Arg Ser Ala Val Ser Phe Pro Pro Arg Lys Gln
                1860                1865                1870

AGA CGT AGA CGC AGG AGC AGG AGG ACC GAA TAC TGT CTA ACC GGG GTA        5723
Arg Arg Arg Arg Arg Ser Arg Arg Thr Glu Tyr Cys Leu Thr Gly Val
        1875                1880                1885

GGT GGG TAC ATA TTT TCG ACG GAC ACA GGC CCT GGG CAC TTG CAA AAG        5771
Gly Gly Tyr Ile Phe Ser Thr Asp Thr Gly Pro Gly His Leu Gln Lys
    1890                1895                1900

AAG TCC GTT CTG CAG AAC CAG CTT ACA GAA CCG ACC TTG GAG CGC AAT        5819
Lys Ser Val Leu Gln Asn Gln Leu Thr Glu Pro Thr Leu Glu Arg Asn
1905                1910                1915                1920
```

```
GTT CTG GAA AGA ATC TAC GCC CCG GTG CTC GAC ACG TCG AAA GAG GAA    5867
Val Leu Glu Arg Ile Tyr Ala Pro Val Leu Asp Thr Ser Lys Glu Glu
            1925                1930                1935

CAG CTC AAA CTC AGG TAC CAG ATG ATG CCC ACC GAA GCC AAC AAA AGC    5915
Gln Leu Lys Leu Arg Tyr Gln Met Met Pro Thr Glu Ala Asn Lys Ser
            1940                1945                1950

AGG TAC CAG TCT CGA AAA GTA GAA AAC CAG AAA GCC ATA ACC ACT GAG    5963
Arg Tyr Gln Ser Arg Lys Val Glu Asn Gln Lys Ala Ile Thr Thr Glu
            1955                1960                1965

CGA CTG CTT TCA GGG CTA CGA CTG TAT AAC TCT GCC ACA GAT CAG CCA    6011
Arg Leu Leu Ser Gly Leu Arg Leu Tyr Asn Ser Ala Thr Asp Gln Pro
            1970                1975                1980

GAA TGC TAT AAG ATC ACC TAC CCG AAA CCA TCG TAT TCC AGC AGT GTA    6059
Glu Cys Tyr Lys Ile Thr Tyr Pro Lys Pro Ser Tyr Ser Ser Ser Val
1985                1990                1995                2000

CCA GCG AAC TAC TCT GAC CCA AAG TTT GCT GTA GCT GTT TGT AAC AAC    6107
Pro Ala Asn Tyr Ser Asp Pro Lys Phe Ala Val Ala Val Cys Asn Asn
                2005                2010                2015

TAT CTG CAT GAG AAT TAC CCG ACG GTA GCA TCT TAT CAG ATC ACC GAC    6155
Tyr Leu His Glu Asn Tyr Pro Thr Val Ala Ser Tyr Gln Ile Thr Asp
            2020                2025                2030

GAG TAC GAT GCT TAC TTG GAT ATG GTA GAC GGG ACA GTC GCT TGC CTA    6203
Glu Tyr Asp Ala Tyr Leu Asp Met Val Asp Gly Thr Val Ala Cys Leu
            2035                2040                2045

GAT ACT GCA ACT TTT TGC CCC GCC AAG CTT AGA AGT TAC CCG AAA AGA    6251
Asp Thr Ala Thr Phe Cys Pro Ala Lys Leu Arg Ser Tyr Pro Lys Arg
            2050                2055                2060

CAC GAG TAT AGA GCC CCA AAC ATC CGC AGT GCG GTT CCA TCA GCG ATG    6299
His Glu Tyr Arg Ala Pro Asn Ile Arg Ser Ala Val Pro Ser Ala Met
2065                2070                2075                2080

CAG AAC ACG TTG CAA AAC GTG CTC ATT GCC GCG ACT AAA AGA AAC TGC    6347
Gln Asn Thr Leu Gln Asn Val Leu Ile Ala Ala Thr Lys Arg Asn Cys
                2085                2090                2095

AAC GTC ACA CAA ATG CGT GAA CTG CCA ACA CTG GAC TCA GCG ACA TTC    6395
Asn Val Thr Gln Met Arg Glu Leu Pro Thr Leu Asp Ser Ala Thr Phe
            2100                2105                2110

AAC GTT GAA TGC TTT CGA AAA TAT GCA TGC AAT GAC GAG TAT TGG GAG    6443
Asn Val Glu Cys Phe Arg Lys Tyr Ala Cys Asn Asp Glu Tyr Trp Glu
            2115                2120                2125

GAG TTT GCC CGA AAG CCA ATT AGG ATC ACT ACT GAG TTC GTT ACC GCA    6491
Glu Phe Ala Arg Lys Pro Ile Arg Ile Thr Thr Glu Phe Val Thr Ala
            2130                2135                2140

TAC GTG GCC AGA CTG AAA GGC CCT AAG GCC GCC GCA CTG TTC GCA AAG    6539
Tyr Val Ala Arg Leu Lys Gly Pro Lys Ala Ala Ala Leu Phe Ala Lys
2145                2150                2155                2160

ACG CAT AAT TTG GTC CCA TTG CAA GAA GTG CCT ATG GAT AGA TTC GTC    6587
Thr His Asn Leu Val Pro Leu Gln Glu Val Pro Met Asp Arg Phe Val
            2165                2170                2175

ATG GAC ATG AAA AGA GAC GTG AAA GTT ACA CCT GGC ACG AAA CAC ACA    6635
Met Asp Met Lys Arg Asp Val Lys Val Thr Pro Gly Thr Lys His Thr
            2180                2185                2190

GAA GAA AGA CCG AAA GTA CAA GTG ATA CAA GCC GCA GAA CCC CTG GCG    6683
Glu Glu Arg Pro Lys Val Gln Val Ile Gln Ala Ala Glu Pro Leu Ala
            2195                2200                2205

ACC GCT TAC CTA TGC GGG ATC CAC CGG GAG TTA GTG CGC AGG CTT ACA    6731
Thr Ala Tyr Leu Cys Gly Ile His Arg Glu Leu Val Arg Arg Leu Thr
            2210                2215                2220

GCC GTT TTG CTA CCC AAC ATT CAC ACG CTC TTT GAC ATG TCG GCG GAG    6779
Ala Val Leu Leu Pro Asn Ile His Thr Leu Phe Asp Met Ser Ala Glu
2225                2230                2235                2240
```

```
                                                           -continued

GAC TTT GAT GCA ATC ATA GCA GAA CAC TTC AAG CAA GGT GAC CCG GTA     6827
Asp Phe Asp Ala Ile Ile Ala Glu His Phe Lys Gln Gly Asp Pro Val
                 2245                2250                2255

CTG GAG ACG GAT ATC GCC TCG TTC GAC AAA AGC CAA GAC GAC GCT ATG     6875
Leu Glu Thr Asp Ile Ala Ser Phe Asp Lys Ser Gln Asp Asp Ala Met
                 2260                2265                2270

GCG TTA ACC GGC CTG ATG ATC TTG GAA GAC CTG GGT GTG GAC CAA CCA     6923
Ala Leu Thr Gly Leu Met Ile Leu Glu Asp Leu Gly Val Asp Gln Pro
                 2275                2280                2285

CTA CTC GAC TTG ATC GAG TGC GCC TTT GGA GAA ATA TCA TCC ACC CAT     6971
Leu Leu Asp Leu Ile Glu Cys Ala Phe Gly Glu Ile Ser Ser Thr His
                 2290                2295                2300

CTG CCC ACG GGT ACC CGT TTC AAA TTC GGG GCG ATG ATG AAA TCC GGA     7019
Leu Pro Thr Gly Thr Arg Phe Lys Phe Gly Ala Met Met Lys Ser Gly
  2305                2310                2315                2320

ATG TTC CTC ACG CTC TTT GTC AAC ACA GTT CTG AAT GTC GTT ATC GCC     7067
Met Phe Leu Thr Leu Phe Val Asn Thr Val Leu Asn Val Val Ile Ala
                 2325                2330                2335

AGC AGA GTA TTG GAG GAG CGG CTT AAA ACG TCC AAA TGT GCA GCA TTT     7115
Ser Arg Val Leu Glu Glu Arg Leu Lys Thr Ser Lys Cys Ala Ala Phe
                 2340                2345                2350

ATC GGC GAC GAC AAC ATT ATA CAC GGA GTA GTA TCT GAC AAA GAA ATG     7163
Ile Gly Asp Asp Asn Ile Ile His Gly Val Val Ser Asp Lys Glu Met
                 2355                2360                2365

GCT GAG AGG TGT GCC ACC TGG CTC AAC ATG GAG GTT AAG ATC ATT GAC     7211
Ala Glu Arg Cys Ala Thr Trp Leu Asn Met Glu Val Lys Ile Ile Asp
                 2370                2375                2380

GCA GTC ATC GGC GAG AGA CCA CCT TAC TTC TGC GGT GGA TTC ATC TTG     7259
Ala Val Ile Gly Glu Arg Pro Pro Tyr Phe Cys Gly Gly Phe Ile Leu
2385                2390                2395                2400

CAA GAT TCG GTT ACC TCC ACA GCG TGT CGC GTG GCG GAC CCC TTG AAA     7307
Gln Asp Ser Val Thr Ser Thr Ala Cys Arg Val Ala Asp Pro Leu Lys
                 2405                2410                2415

AGG CTG TTT AAG TTG GGT AAA CCG CTC CCA GCC GAC GAT GAG CAA GAC     7355
Arg Leu Phe Lys Leu Gly Lys Pro Leu Pro Ala Asp Asp Glu Gln Asp
                 2420                2425                2430

GAA GAC AGA AGA CGC GCT CTG CTA GAT GAA ACA AAG GCG TGG TTT AGA     7403
Glu Asp Arg Arg Arg Ala Leu Leu Asp Glu Thr Lys Ala Trp Phe Arg
                 2435                2440                2445

GTA GGT ATA ACA GAC ACC TTA GCA GTG GCC GTG GCA ACT CGG TAT GAG     7451
Val Gly Ile Thr Asp Thr Leu Ala Val Ala Val Ala Thr Arg Tyr Glu
                 2450                2455                2460

GTA GAC AAC ATC ACA CCT GTC CTG CTG GCA TTG AGA ACT TTT GCC CAG     7499
Val Asp Asn Ile Thr Pro Val Leu Leu Ala Leu Arg Thr Phe Ala Gln
2465                2470                2475                2480

AGC AAA AGA GCA TTT CAA GCC ATC AGA GGG GAA ATA AAG CAT CTC TAC     7547
Ser Lys Arg Ala Phe Gln Ala Ile Arg Gly Glu Ile Lys His Leu Tyr
                 2485                2490                2495

GGT GGT CCT AAA TAGTCAGCAT AGTACATTTC ATCTGACTAA TACCACAACA         7599
Gly Gly Pro Lys
             2500

CCACCACC ATG AAT AGA GGA TTC TTT AAC ATG CTC GGC CGC CGC CCC TTC    7649
         Met Asn Arg Gly Phe Phe Asn Met Leu Gly Arg Arg Pro Phe
           1               5                    10

CCA GCC CCC ACT GCC ATG TGG AGG CCG CGG AGA AGG AGG CAG GCG GCC     7697
Pro Ala Pro Thr Ala Met Trp Arg Pro Arg Arg Arg Arg Gln Ala Ala
 15                  20                  25                  30

CCG ATG CCT GCC CGC AAT GGG CTG GCT TCC CAA ATC CAG CAA CTG ACC     7745
Pro Met Pro Ala Arg Asn Gly Leu Ala Ser Gln Ile Gln Gln Leu Thr
```

```
                    35                40                45
ACA GCC GTC AGT GCC CTA GTC ATT GGA CAG GCA ACT AGA CCT CAA ACC      7793
Thr Ala Val Ser Ala Leu Val Ile Gly Gln Ala Thr Arg Pro Gln Thr
                50                55                60

CCA CGC CCA CGC CCG CCG CCG CGC CAG AAG AAG CAG GCG CCA AAG CAA      7841
Pro Arg Pro Arg Pro Pro Pro Arg Gln Lys Lys Gln Ala Pro Lys Gln
            65                70                75

CCA CCG AAG CCG AAG AAA CCA AAA ACA CAG GAG AAG AAG AAG AAG CAA      7889
Pro Pro Lys Pro Lys Lys Pro Lys Thr Gln Glu Lys Lys Lys Lys Gln
        80                85                90

CCT GCA AAA CCC AAA CCC GGA AAG AGA CAG CGT ATG GCA CTT AAG TTG      7937
Pro Ala Lys Pro Lys Pro Gly Lys Arg Gln Arg Met Ala Leu Lys Leu
 95               100               105               110

GAG GCC GAC AGA CTG TTC GAC GTC AAA AAT GAG GAC GGA GAT GTC ATC      7985
Glu Ala Asp Arg Leu Phe Asp Val Lys Asn Glu Asp Gly Asp Val Ile
                115               120               125

GGG CAC GCA CTG GCC ATG GAA GGA AAG GTA ATG AAA CCA CTC CAC GTG      8033
Gly His Ala Leu Ala Met Glu Gly Lys Val Met Lys Pro Leu His Val
            130               135               140

AAA GGA ACT ATT GAC CAC CCT GTG CTA TCA AAG CTC AAA TTC ACC AAG      8081
Lys Gly Thr Ile Asp His Pro Val Leu Ser Lys Leu Lys Phe Thr Lys
        145               150               155

TCG TCA GCA TAC GAC ATG GAG TTC GCA CAG TTG CCG GTC AAC ATG AGA      8129
Ser Ser Ala Tyr Asp Met Glu Phe Ala Gln Leu Pro Val Asn Met Arg
    160               165               170

AGT GAG GCG TTC ACC TAC ACC AGT GAA CAC CCT GAA GGG TTC TAC AAC      8177
Ser Glu Ala Phe Thr Tyr Thr Ser Glu His Pro Glu Gly Phe Tyr Asn
175               180               185               190

TGG CAC CAC GGA GCG GTG CAG TAT AGT GGA GGC AGA TTT ACC ATC CCC      8225
Trp His His Gly Ala Val Gln Tyr Ser Gly Gly Arg Phe Thr Ile Pro
                195               200               205

CGC GGA GTA GGA GGC AGA GGA GAC AGT GGT CGT CCG ATT ATG GAT AAC      8273
Arg Gly Val Gly Gly Arg Gly Asp Ser Gly Arg Pro Ile Met Asp Asn
            210               215               220

TCA GGC CGG GTT GTC GCG ATA GTC CTC GGA GGG GCT GAT GAG GGA ACA      8321
Ser Gly Arg Val Val Ala Ile Val Leu Gly Gly Ala Asp Glu Gly Thr
        225               230               235

AGA ACC GCC CTT TCG GTC GTC ACC TGG AAT AGC AAA GGG AAG ACA ATC      8369
Arg Thr Ala Leu Ser Val Val Thr Trp Asn Ser Lys Gly Lys Thr Ile
    240               245               250

AAG ACA ACC CCG GAA GGG ACA GAA GAG TGG TCT GCT GCA CCA CTG GTC      8417
Lys Thr Thr Pro Glu Gly Thr Glu Glu Trp Ser Ala Ala Pro Leu Val
255               260               265               270

ACG GCC ATG TGC TTG CTT GGA AAC GTG AGC TTC CCA TGC AAT CGC CCG      8465
Thr Ala Met Cys Leu Leu Gly Asn Val Ser Phe Pro Cys Asn Arg Pro
                275               280               285

CCC ACA TGC TAC ACC CGC GAA CCA TCC AGA GCT CTC GAC ATC CTC GAA      8513
Pro Thr Cys Tyr Thr Arg Glu Pro Ser Arg Ala Leu Asp Ile Leu Glu
            290               295               300

GAG AAC GTG AAC CAC GAG GCC TAC GAC ACC CTG CTC AAC GCC ATA TTG      8561
Glu Asn Val Asn His Glu Ala Tyr Asp Thr Leu Leu Asn Ala Ile Leu
        305               310               315

CGG TGC GGA TCG TCC GGC AGA AGT AAA AGA AGC GTC ACT GAC GAC TTT      8609
Arg Cys Gly Ser Ser Gly Arg Ser Lys Arg Ser Val Thr Asp Asp Phe
    320               325               330

ACC TTG ACC AGC CCG TAC TTG GGC ACA TGC TCG TAC TGT CAC CAT ACT      8657
Thr Leu Thr Ser Pro Tyr Leu Gly Thr Cys Ser Tyr Cys His His Thr
335               340               345               350

GAA CCG TGC TTT AGC CCG ATT AAG ATC GAG CAG GTC TGG GAT GAA GCG      8705
```

```
                                        -continued

Glu Pro Cys Phe Ser Pro Ile Lys Ile Glu Gln Val Trp Asp Glu Ala
            355                 360                 365

GAC GAC AAC ACC ATA CGC ATA CAG ACT TCC GCC CAG TTT GGA TAC GAC      8753
Asp Asp Asn Thr Ile Arg Ile Gln Thr Ser Ala Gln Phe Gly Tyr Asp
                370                 375                 380

CAA AGC GGA GCA GCA AGC TCA AAT AAG TAC CGC TAC ATG TCG CTC GAG      8801
Gln Ser Gly Ala Ala Ser Ser Asn Lys Tyr Arg Tyr Met Ser Leu Glu
            385                 390                 395

CAG GAT CAT ACT GTC AAA GAA GGC ACC ATG GAT GAC ATC AAG ATC AGC      8849
Gln Asp His Thr Val Lys Glu Gly Thr Met Asp Asp Ile Lys Ile Ser
        400                 405                 410

ACC TCA GGA CCG TGT AGA AGG CTT AGC TAC AAA GGA TAC TTT CTC CTC      8897
Thr Ser Gly Pro Cys Arg Arg Leu Ser Tyr Lys Gly Tyr Phe Leu Leu
415                 420                 425                 430

GCG AAG TGT CCT CCA GGG GAC AGC GTA ACG GTT AGC ATA GCG AGT AGC      8945
Ala Lys Cys Pro Pro Gly Asp Ser Val Thr Val Ser Ile Ala Ser Ser
                435                 440                 445

AAC TCA GCA ACG TCA TGC ACA ATG GCC CGC AAG ATA AAA CCA AAA TTC      8993
Asn Ser Ala Thr Ser Cys Thr Met Ala Arg Lys Ile Lys Pro Lys Phe
            450                 455                 460

GTG GGA CGG GAA AAA TAT GAC CTA CCT CCC GTT CAC GGT AAG AAG ATT      9041
Val Gly Arg Glu Lys Tyr Asp Leu Pro Pro Val His Gly Lys Lys Ile
        465                 470                 475

CCT TGC ACA GTG TAC GAC CGT CTG AAA GAA ACA ACC GCC GGC TAC ATC      9089
Pro Cys Thr Val Tyr Asp Arg Leu Lys Glu Thr Thr Ala Gly Tyr Ile
        480                 485                 490

ACT ATG CAC AGG CCG GGA CCG CAT GCC TAT ACA TCC TAT CTG GAG GAA      9137
Thr Met His Arg Pro Gly Pro His Ala Tyr Thr Ser Tyr Leu Glu Glu
495                 500                 505                 510

TCA TCA GGG AAA GTT TAC GCG AAG CCA CCA TCC GGG AAG AAC ATT ACG      9185
Ser Ser Gly Lys Val Tyr Ala Lys Pro Pro Ser Gly Lys Asn Ile Thr
                515                 520                 525

TAC GAG TGC AAG TGC GGC GAT TAC AAG ACC GGA ACC GTT ACG ACC CGT      9233
Tyr Glu Cys Lys Cys Gly Asp Tyr Lys Thr Gly Thr Val Thr Thr Arg
            530                 535                 540

ACC GAA ATC ACG GGC TGC ACC GCC ATC AAG CAG TGC GTC GCC TAT AAG      9281
Thr Glu Ile Thr Gly Cys Thr Ala Ile Lys Gln Cys Val Ala Tyr Lys
        545                 550                 555

AGC GAC CAA ACG AAG TGG GTC TTC AAC TCG CCG GAC TCG ATC AGA CAC      9329
Ser Asp Gln Thr Lys Trp Val Phe Asn Ser Pro Asp Ser Ile Arg His
        560                 565                 570

GCC GAC CAC ACG GCC CAA GGG AAA TTG CAT TTG CCT TTC AAG CTG ATC      9377
Ala Asp His Thr Ala Gln Gly Lys Leu His Leu Pro Phe Lys Leu Ile
575                 580                 585                 590

CCG AGT ACC TGC ATG GTC CCT GTT GCC CAC GCG CCG AAC GTA GTA CAC      9425
Pro Ser Thr Cys Met Val Pro Val Ala His Ala Pro Asn Val Val His
                595                 600                 605

GGC TTT AAA CAC ATC AGC CTC CAA TTA GAC ACA GAC CAT CTG ACA TTG      9473
Gly Phe Lys His Ile Ser Leu Gln Leu Asp Thr Asp His Leu Thr Leu
            610                 615                 620

CTC ACC ACC AGG AGA CTA GGG GCA AAC CCG GAA CCA ACC ACT GAA TGG      9521
Leu Thr Thr Arg Arg Leu Gly Ala Asn Pro Glu Pro Thr Thr Glu Trp
        625                 630                 635

ATC ATC GGA AAC ACG GTT AGA AAC TTC ACC GTC GAC CGA GAT GGC CTG      9569
Ile Ile Gly Asn Thr Val Arg Asn Phe Thr Val Asp Arg Asp Gly Leu
        640                 645                 650

GAA TAC ATA TGG GGC AAT CAC GAA CCA GTA AGG GTC TAT GCC CAA GAG      9617
Glu Tyr Ile Trp Gly Asn His Glu Pro Val Arg Val Tyr Ala Gln Glu
655                 660                 665                 670
```

```
TCT GCA CCA GGA GAC CCT CAC GGA TGG CCA CAC GAA ATA GTA CAG CAT         9665
Ser Ala Pro Gly Asp Pro His Gly Trp Pro His Glu Ile Val Gln His
                675                 680                 685

TAC TAT CAT CGC CAT CCT GTG TAC ACC ATC TTA GCC GTC GCA TCA GCT         9713
Tyr Tyr His Arg His Pro Val Tyr Thr Ile Leu Ala Val Ala Ser Ala
        690                 695                 700

GCT GTG GCG ATG ATG ATT GGC GTA ACT GTT GCA GCA TTA TGT GCC TGT         9761
Ala Val Ala Met Met Ile Gly Val Thr Val Ala Ala Leu Cys Ala Cys
705                 710                 715

AAA GCG CGC CGT GAG TGC CTG ACG CCA TAT GCC CTG GCC CCA AAT GCC         9809
Lys Ala Arg Arg Glu Cys Leu Thr Pro Tyr Ala Leu Ala Pro Asn Ala
            720                 725                 730

GTG ATT CCA ACT TCG CTG GCA CTT TTG TGC TGT GTT AGG TCG GCT AAT         9857
Val Ile Pro Thr Ser Leu Ala Leu Leu Cys Cys Val Arg Ser Ala Asn
735                 740                 745                 750

GCT GAA ACA TTC ACC GAG ACC ATG AGT TAC TTA TGG TCG AAC AGC CAG         9905
Ala Glu Thr Phe Thr Glu Thr Met Ser Tyr Leu Trp Ser Asn Ser Gln
                755                 760                 765

CCG TTC TTC TGG GTC CAG CTG TGT ATA CCT CTG GCC GCT GTC GTC GTT         9953
Pro Phe Phe Trp Val Gln Leu Cys Ile Pro Leu Ala Ala Val Val Val
        770                 775                 780

CTA ATG CGC TGT TGC TCA TGC TGC CTG CCT TTT TTA GTG GTT GCC GGC        10001
Leu Met Arg Cys Cys Ser Cys Cys Leu Pro Phe Leu Val Val Ala Gly
785                 790                 795

GCC TAC CTG GCG AAG GTA GAC GCC TAC GAA CAT GCG ACC ACT GTT CCA        10049
Ala Tyr Leu Ala Lys Val Asp Ala Tyr Glu His Ala Thr Thr Val Pro
            800                 805                 810

AAT GTG CCA CAG ATA CCG TAT AAG GCA CTT GTT GAA AGG GCA GGG TAC        10097
Asn Val Pro Gln Ile Pro Tyr Lys Ala Leu Val Glu Arg Ala Gly Tyr
815                 820                 825                 830

GCC CCG CTC AAT TTG GAG ATT ACT GTC ATG TCC TCG GAG GTT TTG CCT        10145
Ala Pro Leu Asn Leu Glu Ile Thr Val Met Ser Ser Glu Val Leu Pro
                835                 840                 845

TCC ACC AAC CAA GAG TAC ATT ACC TGC AAA TTC ACC ACT GTG GTC CCC        10193
Ser Thr Asn Gln Glu Tyr Ile Thr Cys Lys Phe Thr Thr Val Val Pro
        850                 855                 860

TCC CCT AAA GTC AGA TGC TGC GGC TCC TTG GAA TGT CAG CCC GCC GCT        10241
Ser Pro Lys Val Arg Cys Cys Gly Ser Leu Glu Cys Gln Pro Ala Ala
865                 870                 875

CAC GCA GAC TAT ACC TGC AAG GTC TTT GGA GGG GTG TAC CCC TTC ATG        10289
His Ala Asp Tyr Thr Cys Lys Val Phe Gly Gly Val Tyr Pro Phe Met
            880                 885                 890

TGG GGA GGA GCA CAA TGT TTT TGC GAC AGT GAG AAC AGC CAG ATG AGT        10337
Trp Gly Gly Ala Gln Cys Phe Cys Asp Ser Glu Asn Ser Gln Met Ser
895                 900                 905                 910

GAG GCG TAC GTC GAA TTG TCA GTA GAT TGC GCG ACT GAC CAC GCG CAG        10385
Glu Ala Tyr Val Glu Leu Ser Val Asp Cys Ala Thr Asp His Ala Gln
                915                 920                 925

GCG ATT AAG GTG CAT ACT GCC GCG ATG AAA GTA GGA CTG CGT ATA GTG        10433
Ala Ile Lys Val His Thr Ala Ala Met Lys Val Gly Leu Arg Ile Val
        930                 935                 940

TAC GGG AAC ACT ACC AGT TTC CTA GAT GTG TAC GTG AAC GGA GTC ACA        10481
Tyr Gly Asn Thr Thr Ser Phe Leu Asp Val Tyr Val Asn Gly Val Thr
945                 950                 955

CCA GGA ACG TCT AAA GAC CTG AAA GTC ATA GCT GGA CCA ATT TCA GCA        10529
Pro Gly Thr Ser Lys Asp Leu Lys Val Ile Ala Gly Pro Ile Ser Ala
            960                 965                 970

TTG TTT ACA CCA TTC GAT CAC AAG GTC GTT ATC AAT CGC GGC CTG GTG        10577
Leu Phe Thr Pro Phe Asp His Lys Val Val Ile Asn Arg Gly Leu Val
975                 980                 985                 990
```

```
                                                                              -continued TAC AAC TAT GAC TTT CCG GAA TAC GGA GCG ATG AAA CCA GGA GCG TTT             10625
Tyr Asn Tyr Asp Phe Pro Glu Tyr Gly Ala Met Lys Pro Gly Ala Phe
                995                 1000                1005

GGA GAC ATT CAA GCT ACC TCC TTG ACT AGC AAA GAC CTC ATC GCC AGC             10673
Gly Asp Ile Gln Ala Thr Ser Leu Thr Ser Lys Asp Leu Ile Ala Ser
            1010                1015                1020

ACA GAC ATT AGG CTA CTC AAG CCT TCC GCC AAG AAC GTG CAT GTC CCG             10721
Thr Asp Ile Arg Leu Leu Lys Pro Ser Ala Lys Asn Val His Val Pro
        1025                1030                1035

TAC ACG CAG GCC GCA TCT GGA TTC GAG ATG TGG AAA AAC AAC TCA GGC             10769
Tyr Thr Gln Ala Ala Ser Gly Phe Glu Met Trp Lys Asn Asn Ser Gly
    1040                1045                1050

CGC CCA CTG CAG GAA ACC GCC CCT TTT GGG TGC AAG ATT GCA GTC AAT             10817
Arg Pro Leu Gln Glu Thr Ala Pro Phe Gly Cys Lys Ile Ala Val Asn
1055                1060                1065                1070

CCG CTT CGA GCG GTG GAC TGC TCA TAC GGG AAC ATT CCC ATT TCT ATT             10865
Pro Leu Arg Ala Val Asp Cys Ser Tyr Gly Asn Ile Pro Ile Ser Ile
                1075                1080                1085

GAC ATC CCG AAC GCT GCC TTT ATC AGG ACA TCA GAT GCA CCA CTG GTC             10913
Asp Ile Pro Asn Ala Ala Phe Ile Arg Thr Ser Asp Ala Pro Leu Val
            1090                1095                1100

TCA ACA GTC AAA TGT GAT GTC AGT GAG TGC ACT TAT TCA GCG GAC TTC             10961
Ser Thr Val Lys Cys Asp Val Ser Glu Cys Thr Tyr Ser Ala Asp Phe
        1105                1110                1115

GGA GGG ATG GCT ACC CTG CAG TAT GTA TCC GAC CGC GAA GGA CAA TGC             11009
Gly Gly Met Ala Thr Leu Gln Tyr Val Ser Asp Arg Glu Gly Gln Cys
    1120                1125                1130

CCT GTA CAT TCG CAT TCG AGC ACA GCA ACC CTC CAA GAG TCG ACA GTT             11057
Pro Val His Ser His Ser Ser Thr Ala Thr Leu Gln Glu Ser Thr Val
1135                1140                1145                1150

CAT GTC CTG GAG AAA GGA GCG GTG ACA GTA CAC TTC AGC ACC GCG AGC             11105
His Val Leu Glu Lys Gly Ala Val Thr Val His Phe Ser Thr Ala Ser
                1155                1160                1165

CCA CAG GCG AAC TTC ATT GTA TCG CTG TGT GGT AAG AAG ACA ACA TGC             11153
Pro Gln Ala Asn Phe Ile Val Ser Leu Cys Gly Lys Lys Thr Thr Cys
            1170                1175                1180

AAT GCA GAA TGC AAA CCA CCA GCT GAT CAT ATC GTG AGC ACC CCG CAC             11201
Asn Ala Glu Cys Lys Pro Pro Ala Asp His Ile Val Ser Thr Pro His
        1185                1190                1195

AAA AAT GAC CAA GAA TTC CAA GCC GCC ATC TCA AAA ACT TCA TGG AGT             11249
Lys Asn Asp Gln Glu Phe Gln Ala Ala Ile Ser Lys Thr Ser Trp Ser
    1200                1205                1210

TGG CTG TTT GCC CTT TTC GGC GGC GCC TCG TCG CTA TTA ATT ATA GGA             11297
Trp Leu Phe Ala Leu Phe Gly Gly Ala Ser Ser Leu Leu Ile Ile Gly
1215                1220                1225                1230

CTT ATG ATT TTT GCT TGC AGC ATG ATG CTG ACT AGC ACA CGA AGA                 11342
Leu Met Ile Phe Ala Cys Ser Met Met Leu Thr Ser Thr Arg Arg
                1235                1240                1245

TGACCGCTAC GCCCCAATGA CCCGACCAGC AAAACTCGAT GTACTTCCGA GGAACTGATG           11402

TGCATAATGC ATCAGGCTGG TATATTAGAT CCCCGCTTAC CGCGGGCAAT ATAGCAACAC           11462

CAAAACTCGA CGTATTTCCG AGGAAGCGCA GTGCATAATG CTGCGCAGTG TTGCCAAATA           11522

ATCACTATAT TAACCATTTA TTCAGCGGAC GCCAAAACTC AATGTATTTC TGAGGAAGCA           11582

TGGTGCATAA TGCCATGCAG CGTCTGCATA ACTTTTTATT ATTTCTTTTA TTAATCAACA           11642

AAATTTTGTT TTTAACATTT C                                                     11663

(2) INFORMATION FOR SEQ ID NO:2:
```

(i) SEQUENCE CHARACTERISTICS:
    (A) LENGTH: 2500 amino acids
    (B) TYPE: amino acid
    (D) TOPOLOGY: linear (ii) MOLECULE TYPE: protein (xi) SEQUENCE DESCRIPTION: SEQ ID NO:2:

```
Met Glu Lys Pro Val Val Asn Val Asp Val Asp Pro Gln Ser Pro Phe
 1               5                  10                  15

Val Val Gln Leu Gln Lys Ser Phe Pro Gln Phe Glu Val Val Ala Gln
                20                  25                  30

Gln Val Thr Pro Asn Asp His Ala Asn Ala Arg Ala Phe Ser His Leu
            35                  40                  45

Ala Ser Lys Leu Ile Glu Leu Glu Val Pro Thr Thr Ala Thr Ile Leu
     50                  55                  60

Asp Ile Gly Ser Ala Pro Ala Arg Arg Met Phe Ser Glu His Gln Tyr
 65                  70                  75                  80

His Cys Val Cys Pro Met Arg Ser Pro Glu Asp Pro Asp Arg Met Met
                 85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140

Thr Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
            180                 185                 190

Tyr Pro Ala Tyr Asn Thr Asn Trp Ala Asp Glu Lys Val Leu Glu Ala
        195                 200                 205

Arg Asn Ile Gly Leu Cys Ser Thr Lys Leu Ser Glu Gly Arg Thr Gly
    210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Lys Gly Lys Gln Ser
            260                 265                 270

Tyr Thr Cys Arg Cys Asp Thr Val Val Ser Cys Glu Gly Tyr Val Val
        275                 280                 285

Lys Lys Ile Thr Ile Ser Pro Gly Ile Thr Gly Glu Thr Val Gly Tyr
    290                 295                 300

Ala Val Thr Asn Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                325                 330                 335

Ala Thr Ile Cys Asp Gln Met Thr Gly Ile Met Ala Thr Asp Ile Ser
            340                 345                 350

Pro Asp Asp Ala Gln Lys Leu Leu Val Gly Leu Asn Gln Arg Ile Val
        355                 360                 365
```

```
-continued

Ile Asn Gly Lys Thr Asn Arg Asn Thr Asn Thr Met Gln Asn Tyr Leu
    370                 375                 380

Leu Pro Ile Ile Ala Gln Gly Phe Ser Lys Trp Ala Lys Glu Arg Lys
385                 390                 395                 400

Glu Asp Leu Asp Asn Glu Lys Met Leu Gly Thr Arg Glu Arg Lys Leu
                405                 410                 415

Thr Tyr Gly Cys Leu Trp Ala Phe Arg Thr Lys Val His Ser Phe
                420                 425                 430

Tyr Arg Pro Pro Gly Thr Gln Thr Ile Val Lys Val Pro Ala Ser Phe
        435                 440                 445

Ser Ala Phe Pro Met Ser Ser Val Trp Thr Thr Ser Leu Pro Met Ser
    450                 455                 460

Leu Arg Gln Lys Met Lys Leu Ala Leu Gln Pro Lys Lys Glu Glu Lys
465                 470                 475                 480

Leu Leu Gln Val Pro Glu Glu Leu Val Met Glu Ala Lys Ala Ala Phe
                485                 490                 495

Glu Asp Ala Gln Glu Glu Ser Arg Ala Glu Lys Leu Arg Glu Ala Leu
                500                 505                 510

Pro Pro Leu Val Ala Asp Lys Gly Ile Glu Ala Ala Glu Val Val
        515                 520                 525

Cys Glu Val Glu Gly Leu Gln Ala Asp Thr Gly Ala Ala Leu Val Glu
    530                 535                 540

Thr Pro Arg Gly His Val Arg Ile Ile Pro Gln Ala Asn Asp Arg Met
545                 550                 555                 560

Ile Gly Gln Tyr Ile Val Val Ser Pro Ile Ser Val Leu Lys Asn Ala
                565                 570                 575

Lys Leu Ala Pro Ala His Pro Leu Ala Asp Gln Val Lys Ile Ile Thr
                580                 585                 590

His Ser Gly Arg Ser Gly Arg Tyr Ala Val Glu Pro Tyr Asp Ala Lys
        595                 600                 605

Val Leu Met Pro Ala Gly Ser Ala Val Pro Trp Pro Glu Phe Leu Ala
    610                 615                 620

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
                645                 650                 655

Glu Glu Gln Tyr Lys Val Thr Lys Ala Glu Leu Ala Glu Thr Glu Tyr
                660                 665                 670

Val Phe Asp Val Asp Lys Lys Arg Cys Val Lys Lys Glu Glu Ala Ser
                675                 680                 685

Gly Leu Val Leu Ser Gly Glu Leu Thr Asn Pro Pro Tyr His Glu Leu
    690                 695                 700

Ala Leu Glu Gly Leu Lys Thr Arg Pro Ala Val Pro Tyr Lys Val Glu
705                 710                 715                 720

Thr Ile Gly Val Ile Gly Thr Pro Gly Ser Gly Lys Ser Ala Ile Ile
                725                 730                 735

Lys Ser Thr Val Thr Ala Arg Asp Leu Val Thr Ser Gly Lys Lys Glu
                740                 745                 750

Asn Cys Arg Glu Ile Glu Ala Asp Val Leu Arg Leu Arg Gly Met Gln
        755                 760                 765

Ile Thr Ser Lys Thr Val Asp Ser Val Met Leu Asn Gly Cys His Lys
    770                 775                 780

Ala Val Glu Val Leu Tyr Val Asp Glu Ala Phe Arg Cys His Ala Gly
```

-continued

```
            785                 790                 795                 800
Ala Leu Leu Ala Leu Ile Ala Ile Val Arg Pro Arg Lys Lys Val Val
                    805                 810                 815
Leu Cys Gly Asp Pro Lys Gln Cys Gly Phe Phe Asn Met Met Gln Leu
                820                 825                 830
Lys Val His Phe Asn His Pro Glu Lys Asp Ile Cys Thr Lys Thr Phe
                835                 840                 845
Tyr Lys Phe Ile Ser Arg Arg Cys Thr Gln Pro Val Thr Ala Ile Val
            850                 855                 860
Ser Thr Leu His Tyr Asp Gly Lys Met Lys Thr Thr Asn Pro Cys Lys
865                 870                 875                 880
Lys Asn Ile Glu Ile Asp Ile Thr Gly Ala Thr Lys Pro Lys Pro Gly
                885                 890                 895
Asp Ile Ile Leu Thr Cys Phe Arg Gly Trp Val Lys Gln Leu Gln Ile
                900                 905                 910
Asp Tyr Pro Gly His Glu Val Met Thr Ala Ala Ser Gln Gly Leu
            915                 920                 925
Thr Arg Lys Gly Val Tyr Ala Val Arg Gln Lys Val Asn Glu Asn Pro
            930                 935                 940
Leu Tyr Ala Ile Thr Ser Glu His Val Asn Val Leu Leu Thr Arg Thr
945                 950                 955                 960
Glu Asp Arg Leu Val Trp Lys Thr Leu Gln Gly Asp Pro Trp Ile Lys
                965                 970                 975
Gln Leu Thr Asn Val Pro Lys Gly Asn Phe Gln Ala Thr Ile Glu Asp
                980                 985                 990
Trp Glu Ala Glu His Lys Gly Ile Ile Ala Ala Ile Asn Ser Pro Ala
                995                 1000                1005
Pro Arg Thr Asn Pro Phe Ser Cys Lys Thr Asn Val Cys Trp Ala Lys
            1010                1015                1020
Ala Leu Glu Pro Ile Leu Ala Thr Ala Gly Ile Val Leu Thr Gly Cys
1025                1030                1035                1040
Gln Trp Ser Glu Leu Phe Pro Gln Phe Ala Asp Lys Pro His Ser
                1045                1050                1055
Ala Ile Tyr Ala Leu Asp Val Ile Cys Ile Lys Phe Phe Gly Met Asp
            1060                1065                1070
Leu Thr Ser Gly Leu Phe Ser Lys Gln Ser Ile Pro Leu Thr Tyr His
            1075                1080                1085
Pro Ala Asp Ser Ala Arg Pro Val Ala His Trp Asp Asn Ser Pro Gly
            1090                1095                1100
Thr Arg Lys Tyr Gly Tyr Asp His Ala Val Ala Ala Glu Leu Ser Arg
1105                1110                1115                1120
Arg Phe Pro Val Phe Gln Leu Ala Gly Lys Gly Thr Gln Leu Asp Leu
                1125                1130                1135
Gln Thr Gly Arg Thr Arg Val Ile Ser Ala Gln His Asn Leu Val Pro
                1140                1145                1150
Val Asn Arg Asn Leu Pro His Ala Leu Val Pro Glu His Lys Glu Lys
                1155                1160                1165
Gln Pro Gly Pro Val Glu Lys Phe Leu Ser Gln Phe Lys His His Ser
            1170                1175                1180
Val Leu Val Ile Ser Glu Lys Lys Ile Glu Ala Pro His Lys Arg Ile
1185                1190                1195                1200
Glu Trp Ile Ala Pro Ile Gly Ile Ala Gly Ala Asp Lys Asn Tyr Asn
                1205                1210                1215
```

-continued

```
Leu Ala Phe Gly Phe Pro Pro Gln Ala Arg Tyr Asp Leu Val Phe Ile
            1220            1225                1230
Asn Ile Gly Thr Lys Tyr Arg Asn His His Phe Gln Gln Cys Glu Asp
            1235            1240                1245
His Ala Ala Thr Leu Lys Thr Leu Ser Arg Ser Ala Leu Asn Cys Leu
    1250            1255                1260
Asn Pro Gly Gly Thr Leu Val Val Lys Ser Tyr Gly Tyr Ala Asp Arg
1265            1270            1275                1280
Asn Ser Glu Asp Val Val Thr Ala Leu Ala Arg Lys Phe Val Arg Val
            1285            1290                1295
Ser Ala Ala Arg Pro Glu Cys Val Ser Ser Asn Thr Glu Met Tyr Leu
            1300            1305                1310
Ile Phe Arg Gln Leu Asp Asn Ser Arg Thr Arg Gln Phe Thr Pro His
            1315            1320                1325
His Leu Asn Cys Val Ile Ser Ser Val Tyr Gly Thr Arg Asp Gly
            1330            1335                1340
Val Gly Ala Ala Pro Ser Tyr Arg Thr Lys Arg Glu Asn Ile Ala Asp
1345            1350            1355                1360
Cys Gln Glu Glu Ala Val Val Asn Ala Ala Asn Pro Leu Gly Arg Pro
            1365            1370                1375
Gly Glu Gly Val Cys Arg Ala Ile Tyr Lys Arg Trp Pro Asn Ser Phe
            1380            1385                1390
Thr Asp Ser Ala Thr Glu Thr Gly Thr Ala Lys Leu Thr Val Cys Gln
            1395            1400                1405
Gly Lys Lys Val Ile His Ala Val Gly Pro Asp Phe Arg Lys His Pro
    1410            1415                1420
Glu Ala Glu Ala Leu Lys Leu Leu Gln Asn Ala Tyr His Ala Val Ala
1425            1430            1435                1440
Asp Leu Val Asn Glu His Asn Ile Lys Ser Val Ala Ile Pro Leu Leu
            1445            1450                1455
Ser Thr Gly Ile Tyr Ala Ala Gly Lys Asp Arg Leu Glu Val Ser Leu
            1460            1465                1470
Asn Cys Leu Thr Thr Ala Leu Asp Arg Thr Asp Ala Asp Val Thr Ile
    1475            1480                1485
Tyr Cys Leu Asp Lys Lys Trp Lys Glu Arg Ile Asp Ala Val Leu Gln
    1490            1495                1500
Leu Lys Glu Ser Val Thr Glu Leu Lys Asp Glu Asp Met Glu Ile Asp
1505            1510            1515                1520
Asp Glu Leu Val Trp Ile His Pro Asp Ser Cys Leu Lys Gly Arg Lys
            1525            1530                1535
Gly Phe Ser Thr Thr Lys Gly Lys Leu Tyr Ser Tyr Phe Glu Gly Thr
            1540            1545                1550
Lys Phe His Gln Ala Ala Lys Asp Met Ala Glu Ile Lys Val Leu Phe
    1555            1560                1565
Pro Asn Asp Gln Glu Ser Asn Glu Gln Leu Cys Ala Tyr Ile Leu Gly
    1570            1575                1580
Glu Thr Met Glu Ala Ile Arg Glu Lys Cys Pro Val Asp His Asn Pro
1585            1590            1595                1600
Ser Ser Ser Pro Pro Lys Thr Leu Pro Cys Leu Cys Met Tyr Ala Met
            1605            1610                1615
Thr Pro Glu Arg Val His Arg Leu Arg Ser Asn Asn Val Lys Glu Val
            1620            1625                1630
```

-continued

```
Thr Val Cys Ser Ser Thr Pro Leu Pro Lys Tyr Lys Ile Lys Asn Val
        1635                1640                1645

Gln Lys Val Gln Cys Thr Lys Val Val Leu Phe Asn Pro His Thr Pro
    1650                1655                1660

Ala Phe Val Pro Ala Arg Lys Tyr Ile Glu Ala Pro Glu Gln Pro Ala
1665                1670                1675                1680

Ala Pro Pro Ala Gln Ala Glu Glu Ala Pro Gly Val Val Ala Thr Pro
            1685                1690                1695

Thr Pro Pro Ala Ala Asp Asn Thr Ser Leu Asp Val Thr Asp Ile Ser
            1700                1705                1710

Leu Asp Met Glu Asp Ser Ser Glu Gly Ser Leu Phe Ser Ser Phe Ser
        1715                1720                1725

Gly Ser Asp Asn Tyr Arg Arg Gln Val Val Val Ala Asp Val His Ala
        1730                1735                1740

Val Gln Glu Pro Ala Pro Val Pro Pro Arg Leu Lys Lys Met Ala
1745                1750                1755                1760

Arg Leu Ala Ala Ala Arg Met Gln Glu Pro Thr Pro Pro Ala Ser
                1765                1770                1775

Thr Ser Ser Ala Asp Glu Ser Leu His Leu Ser Phe Asp Gly Val Ser
            1780                1785                1790

Ile Ser Phe Gly Ser Leu Phe Asp Gly Glu Met Ala Arg Leu Ala Ala
        1795                1800                1805

Ala Gln Pro Pro Ala Ser Thr Cys Pro Thr Asp Val Pro Met Ser Phe
    1810                1815                1820

Gly Ser Phe Ser Asp Gly Glu Ile Glu Glu Leu Ser Arg Arg Val Thr
1825                1830                1835                1840

Glu Ser Glu Pro Val Leu Phe Gly Ser Phe Glu Pro Gly Glu Val Asn
                1845                1850                1855

Ser Ile Ile Ser Ser Arg Ser Ala Val Ser Phe Pro Pro Arg Lys Gln
            1860                1865                1870

Arg Arg Arg Arg Arg Ser Arg Arg Thr Glu Tyr Cys Leu Thr Gly Val
        1875                1880                1885

Gly Gly Tyr Ile Phe Ser Thr Asp Thr Gly Pro Gly His Leu Gln Lys
    1890                1895                1900

Lys Ser Val Leu Gln Asn Gln Leu Thr Glu Pro Thr Leu Glu Arg Asn
1905                1910                1915                1920

Val Leu Glu Arg Ile Tyr Ala Pro Val Leu Asp Thr Ser Lys Glu Glu
            1925                1930                1935

Gln Leu Lys Leu Arg Tyr Gln Met Met Pro Thr Glu Ala Asn Lys Ser
        1940                1945                1950

Arg Tyr Gln Ser Arg Lys Val Glu Asn Gln Lys Ala Ile Thr Thr Glu
    1955                1960                1965

Arg Leu Leu Ser Gly Leu Arg Leu Tyr Asn Ser Ala Thr Asp Gln Pro
    1970                1975                1980

Glu Cys Tyr Lys Ile Thr Tyr Pro Lys Pro Ser Tyr Ser Ser Ser Val
1985                1990                1995                2000

Pro Ala Asn Tyr Ser Asp Pro Lys Phe Ala Val Ala Val Cys Asn Asn
            2005                2010                2015

Tyr Leu His Glu Asn Tyr Pro Thr Val Ala Ser Tyr Gln Ile Thr Asp
        2020                2025                2030

Glu Tyr Asp Ala Tyr Leu Asp Met Val Asp Gly Thr Val Ala Cys Leu
        2035                2040                2045

Asp Thr Ala Thr Phe Cys Pro Ala Lys Leu Arg Ser Tyr Pro Lys Arg
```

-continued

```
            2050                2055                2060
His Glu Tyr Arg Ala Pro Asn Ile Arg Ser Ala Val Pro Ser Ala Met
2065                2070                2075                2080

Gln Asn Thr Leu Gln Asn Val Leu Ile Ala Ala Thr Lys Arg Asn Cys
            2085                2090                2095

Asn Val Thr Gln Met Arg Glu Leu Pro Thr Leu Asp Ser Ala Thr Phe
            2100                2105                2110

Asn Val Glu Cys Phe Arg Lys Tyr Ala Cys Asn Asp Glu Tyr Trp Glu
            2115                2120                2125

Glu Phe Ala Arg Lys Pro Ile Arg Ile Thr Thr Glu Phe Val Thr Ala
            2130                2135                2140

Tyr Val Ala Arg Leu Lys Gly Pro Lys Ala Ala Ala Leu Phe Ala Lys
2145                2150                2155                2160

Thr His Asn Leu Val Pro Leu Gln Glu Val Pro Met Asp Arg Phe Val
            2165                2170                2175

Met Asp Met Lys Arg Asp Val Lys Val Thr Pro Gly Thr Lys His Thr
            2180                2185                2190

Glu Glu Arg Pro Lys Val Gln Val Ile Gln Ala Ala Glu Pro Leu Ala
            2195                2200                2205

Thr Ala Tyr Leu Cys Gly Ile His Arg Glu Leu Val Arg Arg Leu Thr
            2210                2215                2220

Ala Val Leu Leu Pro Asn Ile His Thr Leu Phe Asp Met Ser Ala Glu
2225                2230                2235                2240

Asp Phe Asp Ala Ile Ile Ala Glu His Phe Lys Gln Gly Asp Pro Val
                2245                2250                2255

Leu Glu Thr Asp Ile Ala Ser Phe Asp Lys Ser Gln Asp Ala Met
            2260                2265                2270

Ala Leu Thr Gly Leu Met Ile Leu Glu Asp Leu Gly Val Asp Gln Pro
            2275                2280                2285

Leu Leu Asp Leu Ile Glu Cys Ala Phe Gly Glu Ile Ser Ser Thr His
            2290                2295                2300

Leu Pro Thr Gly Thr Arg Phe Lys Phe Gly Ala Met Met Lys Ser Gly
2305                2310                2315                2320

Met Phe Leu Thr Leu Phe Val Asn Thr Val Leu Asn Val Val Ile Ala
            2325                2330                2335

Ser Arg Val Leu Glu Glu Arg Leu Lys Thr Ser Lys Cys Ala Ala Phe
            2340                2345                2350

Ile Gly Asp Asp Asn Ile Ile His Gly Val Val Ser Asp Lys Glu Met
            2355                2360                2365

Ala Glu Arg Cys Ala Thr Trp Leu Asn Met Glu Val Lys Ile Ile Asp
            2370                2375                2380

Ala Val Ile Gly Glu Arg Pro Pro Tyr Phe Cys Gly Gly Phe Ile Leu
2385                2390                2395                2400

Gln Asp Ser Val Thr Ser Thr Ala Cys Arg Val Ala Asp Pro Leu Lys
            2405                2410                2415

Arg Leu Phe Lys Leu Gly Lys Pro Leu Pro Ala Asp Asp Glu Gln Asp
            2420                2425                2430

Glu Asp Arg Arg Arg Ala Leu Leu Asp Glu Thr Lys Ala Trp Phe Arg
            2435                2440                2445

Val Gly Ile Thr Asp Thr Leu Ala Val Ala Val Ala Thr Arg Tyr Glu
            2450                2455                2460

Val Asp Asn Ile Thr Pro Val Leu Leu Ala Leu Arg Thr Phe Ala Gln
2465                2470                2475                2480
```

```
Ser Lys Arg Ala Phe Gln Ala Ile Arg Gly Glu Ile Lys His Leu Tyr
                2485                2490                2495

Gly Gly Pro Lys
        2500

(2) INFORMATION FOR SEQ ID NO:3:

(i) SEQUENCE CHARACTERISTICS:
        (A) LENGTH: 1245 amino acids
        (B) TYPE: amino acid
        (D) TOPOLOGY: linear (ii) MOLECULE TYPE: protein (xi) SEQUENCE DESCRIPTION: SEQ ID NO:3:

Met Asn Arg Gly Phe Phe Asn Met Leu Gly Arg Arg Pro Phe Pro Ala
 1               5                  10                  15

Pro Thr Ala Met Trp Arg Pro Arg Arg Arg Gln Ala Ala Pro Met
            20                  25                  30

Pro Ala Arg Asn Gly Leu Ala Ser Gln Ile Gln Gln Leu Thr Thr Ala
            35                  40                  45

Val Ser Ala Leu Val Ile Gly Gln Ala Thr Arg Pro Gln Thr Pro Arg
 50                  55                  60

Pro Arg Pro Pro Pro Arg Gln Lys Lys Gln Ala Pro Lys Gln Pro Pro
 65                  70                  75                  80

Lys Pro Lys Lys Pro Lys Thr Gln Glu Lys Lys Lys Gln Pro Ala
            85                  90                  95

Lys Pro Lys Pro Gly Lys Arg Gln Arg Met Ala Leu Lys Leu Glu Ala
            100                 105                 110

Asp Arg Leu Phe Asp Val Lys Asn Glu Asp Gly Asp Val Ile Gly His
            115                 120                 125

Ala Leu Ala Met Glu Gly Lys Val Met Lys Pro Leu His Val Lys Gly
            130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
            165                 170                 175

Ala Phe Thr Tyr Thr Ser Glu His Pro Glu Gly Phe Tyr Asn Trp His
            180                 185                 190

His Gly Ala Val Gln Tyr Ser Gly Gly Arg Phe Thr Ile Pro Arg Gly
            195                 200                 205

Val Gly Gly Arg Gly Asp Ser Gly Arg Pro Ile Met Asp Asn Ser Gly
            210                 215                 220

Arg Val Val Ala Ile Val Leu Gly Gly Ala Asp Glu Gly Thr Arg Thr
225                 230                 235                 240

Ala Leu Ser Val Thr Trp Asn Ser Lys Gly Lys Thr Ile Lys Thr
            245                 250                 255

Thr Pro Glu Gly Thr Glu Glu Trp Ser Ala Ala Pro Leu Val Thr Ala
            260                 265                 270

Met Cys Leu Leu Gly Asn Val Ser Phe Pro Cys Asn Arg Pro Pro Thr
            275                 280                 285

Cys Tyr Thr Arg Glu Pro Ser Arg Ala Leu Asp Ile Leu Glu Glu Asn
            290                 295                 300

Val Asn His Glu Ala Tyr Asp Thr Leu Leu Asn Ala Ile Leu Arg Cys
305                 310                 315                 320
```

-continued

```
Gly Ser Ser Gly Arg Ser Lys Arg Ser Val Thr Asp Asp Phe Thr Leu
            325                 330                 335

Thr Ser Pro Tyr Leu Gly Thr Cys Ser Tyr Cys His His Thr Glu Pro
            340                 345                 350

Cys Phe Ser Pro Ile Lys Ile Glu Gln Val Trp Asp Glu Ala Asp Asp
            355                 360                 365

Asn Thr Ile Arg Ile Gln Thr Ser Ala Gln Phe Gly Tyr Asp Gln Ser
            370                 375                 380

Gly Ala Ala Ser Ser Asn Lys Tyr Arg Tyr Met Ser Leu Glu Gln Asp
385                 390                 395                 400

His Thr Val Lys Glu Gly Thr Met Asp Asp Ile Lys Ile Ser Thr Ser
            405                 410                 415

Gly Pro Cys Arg Arg Leu Ser Tyr Lys Gly Tyr Phe Leu Leu Ala Lys
            420                 425                 430

Cys Pro Pro Gly Asp Ser Val Thr Val Ser Ile Ala Ser Ser Asn Ser
            435                 440                 445

Ala Thr Ser Cys Thr Met Ala Arg Lys Ile Lys Pro Lys Phe Val Gly
            450                 455                 460

Arg Glu Lys Tyr Asp Leu Pro Pro Val His Gly Lys Lys Ile Pro Cys
465                 470                 475                 480

Thr Val Tyr Asp Arg Leu Lys Glu Thr Thr Ala Gly Tyr Ile Thr Met
            485                 490                 495

His Arg Pro Gly Pro His Ala Tyr Thr Ser Tyr Leu Glu Glu Ser Ser
            500                 505                 510

Gly Lys Val Tyr Ala Lys Pro Pro Ser Gly Lys Asn Ile Thr Tyr Glu
            515                 520                 525

Cys Lys Cys Gly Asp Tyr Lys Thr Gly Thr Val Thr Thr Arg Thr Glu
            530                 535                 540

Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Ser Ile Arg His Ala Asp
            565                 570                 575

His Thr Ala Gln Gly Lys Leu His Leu Pro Phe Lys Leu Ile Pro Ser
            580                 585                 590

Thr Cys Met Val Pro Val Ala His Ala Pro Asn Val Val His Gly Phe
            595                 600                 605

Lys His Ile Ser Leu Gln Leu Asp Thr Asp His Leu Thr Leu Leu Thr
            610                 615                 620

Thr Arg Arg Leu Gly Ala Asn Pro Glu Pro Thr Thr Glu Trp Ile Ile
625                 630                 635                 640

Gly Asn Thr Val Arg Asn Phe Thr Val Asp Arg Asp Gly Leu Glu Tyr
            645                 650                 655

Ile Trp Gly Asn His Glu Pro Val Arg Val Tyr Ala Gln Glu Ser Ala
            660                 665                 670

Pro Gly Asp Pro His Gly Trp Pro His Glu Ile Val Gln His Tyr Tyr
            675                 680                 685

His Arg His Pro Val Tyr Thr Ile Leu Ala Val Ala Ser Ala Ala Val
            690                 695                 700

Ala Met Met Ile Gly Val Thr Val Ala Ala Leu Cys Ala Cys Lys Ala
705                 710                 715                 720

Arg Arg Glu Cys Leu Thr Pro Tyr Ala Leu Ala Pro Asn Ala Val Ile
            725                 730                 735

Pro Thr Ser Leu Ala Leu Leu Cys Cys Val Arg Ser Ala Asn Ala Glu
```

```
                    740             745             750
Thr Phe Thr Glu Thr Met Ser Tyr Leu Trp Ser Asn Ser Gln Pro Phe
                755             760             765
Phe Trp Val Gln Leu Cys Ile Pro Leu Ala Ala Val Val Leu Met
770             775             780
Arg Cys Ser Cys Cys Leu Pro Phe Leu Val Val Ala Gly Ala Tyr
785             790             795             800
Leu Ala Lys Val Asp Ala Tyr Glu His Ala Thr Thr Val Pro Asn Val
                805             810             815
Pro Gln Ile Pro Tyr Lys Ala Leu Val Glu Arg Ala Gly Tyr Ala Pro
                820             825             830
Leu Asn Leu Glu Ile Thr Val Met Ser Ser Glu Val Leu Pro Ser Thr
                835             840             845
Asn Gln Glu Tyr Ile Thr Cys Lys Phe Thr Thr Val Pro Ser Pro
                850             855             860
Lys Val Arg Cys Cys Gly Ser Leu Glu Cys Gln Pro Ala Ala His Ala
865             870             875             880
Asp Tyr Thr Cys Lys Val Phe Gly Gly Val Tyr Pro Phe Met Trp Gly
                885             890             895
Gly Ala Gln Cys Phe Cys Asp Ser Glu Asn Ser Gln Met Ser Glu Ala
                900             905             910
Tyr Val Glu Leu Ser Val Asp Cys Ala Thr Asp His Ala Gln Ala Ile
                915             920             925
Lys Val His Thr Ala Ala Met Lys Val Gly Leu Arg Ile Val Tyr Gly
                930             935             940
Asn Thr Thr Ser Phe Leu Asp Val Tyr Val Asn Gly Val Thr Pro Gly
945             950             955             960
Thr Ser Lys Asp Leu Lys Val Ile Ala Gly Pro Ile Ser Ala Leu Phe
                965             970             975
Thr Pro Phe Asp His Lys Val Val Ile Asn Arg Gly Leu Val Tyr Asn
                980             985             990
Tyr Asp Phe Pro Glu Tyr Gly Ala Met Lys Pro Gly Ala Phe Gly Asp
                995             1000            1005
Ile Gln Ala Thr Ser Leu Thr Ser Lys Asp Leu Ile Ala Ser Thr Asp
                1010            1015            1020
Ile Arg Leu Leu Lys Pro Ser Ala Lys Asn Val His Val Pro Tyr Thr
1025            1030            1035            1040
Gln Ala Ala Ser Gly Phe Glu Met Trp Lys Asn Asn Ser Gly Arg Pro
                1045            1050            1055
Leu Gln Glu Thr Ala Pro Phe Gly Cys Lys Ile Ala Val Asn Pro Leu
                1060            1065            1070
Arg Ala Val Asp Cys Ser Tyr Gly Asn Ile Pro Ile Ser Ile Asp Ile
                1075            1080            1085
Pro Asn Ala Ala Phe Ile Arg Thr Ser Asp Ala Pro Leu Val Ser Thr
                1090            1095            1100
Val Lys Cys Asp Val Ser Glu Cys Thr Tyr Ser Ala Asp Phe Gly Gly
1105            1110            1115            1120
Met Ala Thr Leu Gln Tyr Val Ser Asp Arg Glu Gly Gln Cys Pro Val
                1125            1130            1135
His Ser His Ser Ser Thr Ala Thr Leu Gln Glu Ser Thr Val His Val
                1140            1145            1150
Leu Glu Lys Gly Ala Val Thr Val His Phe Ser Thr Ala Ser Pro Gln
                1155            1160            1165
```

```
Ala Asn Phe Ile Val Ser Leu Cys Gly Lys Lys Thr Thr Cys Asn Ala
    1170            1175            1180

Glu Cys Lys Pro Pro Ala Asp His Ile Val Ser Thr Pro His Lys Asn
1185            1190            1195            1200

Asp Gln Glu Phe Gln Ala Ala Ile Ser Lys Thr Ser Trp Ser Trp Leu
            1205            1210            1215

Phe Ala Leu Phe Gly Gly Ala Ser Ser Leu Leu Ile Ile Gly Leu Met
            1220            1225            1230

Ile Phe Ala Cys Ser Met Met Leu Thr Ser Thr Arg Arg
        1235            1240            1245

(2) INFORMATION FOR SEQ ID NO:4:

(i) SEQUENCE CHARACTERISTICS:
        (A) LENGTH: 11717 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

NTTGNCGGCG TAGTATACAC TATTGAATCA AACAGCCGAC CAATTGCACT ACCATCACA         59

ATG GAG AAG CCA GTA GTT AAC GTA GAC GTA GAC CCG CAG AGT CCG TTT        107

GTC GTG CAA CTG CAA AAG AGC TTC CCG CAA TTT GAG GTA GTA GCA CAG        155

CAG GTC ACT CCA AAT GAC CAT GCT AAT GCC AGA GCA TTT TCG CAT CTG        203

GCC AGT AAA CTA ATC GAG CTG GAG GTT CCT ACC ACA GCG ACG ATT TTG        251

GAC ATA GGC AGC GCA CCG GCT CGT AGA ATG TTT TCC GAG CAC CAG TAC        299

CAT TGC GTT TGC CCC ATG CGT AGT CCA GAA GAC CCG GAC CGC ATG ATG        347

AAA TAT GCC AGC AAA CTG GCG GAA AAA GCA TGC AAG ATT ACG AAT AAG        395

AAC TTG CAT GAG AAG ATC AAG GAC CTC CGG ACC GTA CTT GAT ACA CCG        443

GAT GCT GAA ACG CCA TCA CTC TGC TTC CAC AAC GAT GTT ACC TGC AAC        491

ACG CGT GCC GAG TAC TCC GTC ATG CAG GAC GTG TAC ATC AAC GCT CCC        539

GGA ACT ATT TAC CAT CAG GCT ATG AAA GGC GTG CGG ACC CTG TAC TGG        587

ATT GGC TTC GAT ACC ACC CAG TTC ATG TTC TCG GCT ATG GCA GGT TCG        635

TAC CCT GCG TAC AAC ACC AAC TGG GCC GAC GAA AAA GTC CTC GAA GCG        683

CGT AAC ATC GGA CTC TGC AGC ACA AAG CTG AGT GAA GGC AGG ACA GGA        731

AAG TTG TCG ATA ATG AGG AAG AAG GAG TTG AAG CCC GGG TCA CGG GTT        779

TAT TTC TCC GTT GGA TCG ACA CTT TAC CCA GAA CAC AGA GCC AGC TTG        827

CAG AGC TGG CAT CTT CCA TCG GTG TTC CAC CTG AAA GGA AAG CAG TCG        875

TAC ACT TGC CGC TGT GAT ACA GTG GTG AGC TGC GAA GGC TAC GTA GTG        923

AAG AAA ATC ACC ATC AGT CCC GGG ATC ACG GGA GAA ACC GTG GGA TAC        971

GCG GTT ACA AAC AAT AGC GAG GGC TTC TTG CTA TGC AAA GTT ACC GAT       1019

ACA GTA AAA GGA GAA CGG GTA TCG TTC CCC GTG TGC ACG TAT ATC CCG       1067

GCC ACC ATA TGC GAT CAG ATG ACC GGC ATA ATG GCC ACG GAT ATC TCA       1115

CCT GAC GAT GCA CAA AAA CTT CTG GTT GGG CTC AAC CAG CGA ATC GTC       1163

ATT AAC GGT AAG ACT AAC AGG AAC ACC AAT ACC ATG CAA AAT TAC CTT       1211
```

-continued

```
CTG CCA ATC ATT GCA CAA GGG TTC AGC AAA TGG GCC AAG GAG CGC AAA      1259
GAA GAC CTT GAC AAT GAA AAA ATG CTG GGT ACC AGA GAG CGC AAG CTT      1307
ACA TAT GGC TGC TTG TGG GCG TTT CGC ACT AAG AAA GTG CAC TCG TTC      1355
TAT CGC CCA CCT GGA ACG CAG ACC ATC GTA AAA GTC CCA GCC TCT TTT      1403
AGC GCT TTC CCC ATG TCA TCC GTA TGG ACT ACC TCT TTG CCC ATG TCG      1451
CTG AGG CAG AAG ATA AAA TTG CAT TTA CAA CCA AAG AAG GAG GAA AAA      1499
CTG CTG CAA GTC CCG GAG GAA TTA GTC ATG GAG GCC AAG GCT GCT TTC      1547
GAG GAT GCT CAG GAG GAA TCC AGA GCG GAG AAG CTC CGA GAA GCA CTC      1595
CCA CCA TTA GTG GCA GAC AAA GGT ATC GAG GCA GCC GCG GAA GTT GTC      1643
TGC GAA GTG GAG GGG CTC CAG GCG GAC ATC GGA GCA GCA CTC GTC GAA      1691
ACC CCG CGC GGT CAT GTA AGG ATA ATA CCA CAA GCA AAT GAC CGT ATG      1739
ATC GGA CAG TAC ATC GTT GTC TCG CCA ACC TCT GTG CTG AAG AAC GCT      1787
AAA CTC GCA CCA GCA CAC CCG CTA GCA GAC CAG GTT AAG ATC ATA ACG      1835
CAC TCC GGA AGA TCA GGA AGG TAT GCA GTC GAA CCA TAC GAC GCT AAA      1883
GTA CTG ATG CCA GCA GGA AGT GCC GTA CCA TGG CCA GAA TTC TTA GCA      1931
CTG AGT GAG AGC GCC ACG CTA GTG TAC AAC GAA AGA GAG TTT GTG AAC      1979
CGC AAG CTG TAC CAT ATT GCC ATG CAC GGT CCC GCT AAG AAT ACA GAA      2027
GAG GAG CAG TAC AAG GTT ACA AAG GCA GAG CTC GCA GAA ACA GAG TAC      2075
GTG TTT GAC GTG GAC AAG AAG CGA TGC GTC AAG AAG GAA GAA GCC TCA      2123
GGA CTT GTC CTC TCG GGA GAA CTG ACC AAC CCG CCC TAT CAC GAA CTA      2171
GCT CTT GAG GGA CTG AAG ACT CGA CCC GTG GTC CCG TAC AAG GTT GAA      2219
ACA ATA GGA GTG ATA GGC GCA CCA GGA TCG GGC AAG TCG GCT ATC ATC      2267
AAG TCA ACT GTC ACG GCA CGT GAT CTT GTT ACC AGC GGA AAG AAA GAA      2315
AAC TGC CGC GAA ATT CAG GCC GAT GTG CTA CGG CTG AGG GGC ATG CAG      2363
ATC ACG TCG AAG ACA GTG GAT TCG GTT ATG CTC AAC GGA TGC CGC AAA      2411
GCC GTA GAA GTG CTG TAT GTT GAC GAA GCG TTC GCG TGC CAC GCA GGA      2459
GCA CTA CTT GCC TTG ATT GCA ATC GTC AGA CCC CGT CAT AAG GTA GTG      2507
CTA TGC GGA GAC CCT AAG CAA TGC GGA TTC TTC AAC ATG ATG CAA CTA      2555
AAG GTA TAT TTC AAC CAC CCG GAA AAA GAC ATA TGT ACC AAG ACA TTC      2603
TAC AAG TTT ATC TCC CGA CGT TGC ACA CAG CCA GTC ACG GCT ATT GTA      2651
TCG ACA CTG CAT TAC GAT GGA AAA ATG AAA ACC ACA AAC CCG TGC AAG      2699
AAG AAC ATC GAA ATC GAC ATT ACA GGG GCC ACG AAG CCG AAG CCA GGG      2747
GAC ATC ATC CTG ACA TGC TTC CGC GGG TGG GTT AAG CAA CTG CAA ATC      2795
GAC TAT CCC GGA CAT GAG GTA ATG ACA GCC GCG GCC TCA CAA GGG CTA      2843
ACC AGA AAA GGA GTA TAT GCC GTC CGG CAA AAA GTC AAT GAA AAC CCG      2891
CTG TAC GCG ATC ACA TCA GAG CAT GTG AAC GTG CTG CTC ACC CGC ACT      2939
GAG GAC AGG CTA GTA TGG AAA ACT TTA CAG GGC GAC CCA TGG ATT AAG      2987
CAG CTC ACT AAC GTA CCA AAA GGA AAT TTT CAA GCC ACC ATC GAG GAC      3035
TGG GAA GCT GAA CAC AAG GGA ATA ATT GCT GCG ATA AAC AGT CCC GCT      3083
CCC CGT ACC AAT CCG TTC AGC TGC AAG ACT AAC GTT TGC TGG GCG AAA      3131
```

-continued

```
CGA CTG GAA CCG ATA CTG GCC ACG GCC GGT ATC GTA CTT ACC GGT TGC    3179
CAG TGG AGC GAG CTG TTC CCA CAG TTT GCA GAT GAC AAA CCA CAC TCG    3227
GCC ATC TAC GCC CTG GAC GTA ATC TGC ATT AAG TTT TTC GGC ATG GAC    3275
TTG ACA AGC GGA CTG TTT TCC AAA CAG AGC ATC CCG TTA ACG TAC CAT    3323
CCT GCC GAT TCA GCG AGG CCA GTA GCT CAT TGG GAC AAC AGC CCA GGA    3371
ACC CGC AAG TAT GGG TAC GAT CAC GCC GTT GCC GCC GAA CTC TCC CGT    3419
AGA TTT CCG GTG TTC CAG CTA GCT GGG AAA GGC ACA CAG CTT GAT TTG    3467
CAG ACG GGC AGA ACT AGA GTT ATC TCC GCA CAG CAT AAC TTG GTC CCA    3515
GTG AAC CGC AAT CTC CCG CAC GCC TTA GTC CCC GAG CAC AAG GAG AAA    3563
CAA CCC GGC CCG GTC AAA AAA TTC TTG AGC AGT TCA AAA CAC CAC TCC    3611
GTA CTT GTG GTC TCA GAG GAA AAA ATT GAA GCT CCC CAC AAG AGA ATC    3659
GAA TGG ATC GCC CCG ATT GGC ATA GCC GGC GCT GAT AAG AAC TAC AAC    3707
CTG GCT TTC GGG TTT CCG CCG CAG GCA CGG TAC GAC CTG GTG TTT ATC    3755
AAT ATT GGA ACT AAA TAC AGA AAC CAT CAC TTT CAG CAG TGC GAA GAC    3803
CAT GCG GCG ACC TTG AAA ACC CTC TCG CGT TCG GCC CTG AAC TGC CTT    3851
AAC CCC GGA GGC ACC CTC GTG GTG AAG TCC TAC GGT TAC GCC GAC CGC    3899
AAT AGT GAG GAC GTA GTC ACC GCT CTT GCC AGA AAA TTT GTC AGA GTG    3947
TCT GCA GCG AGG CCA GAG TGC GTC TCA AGC AAT ACA GAA ATG TAC CTG    3995
ATC TTC CGA CAA CTA GAC AAC AGC CGC ACA CGA CAA TTC ACC CCG CAT    4043
CAT CTG AAT TGT GTG ATT TCG TCC GTG TAC GAG GGT ACA AGA GAC GGA    4091
GTT GGA GCC GCA CCG TCA TAC CGC ACT AAA AGG GAG AAC ATT GCT GAT    4139
TGT CAA GAG GAA GCA GTT GTC AAT GCA GCC AAT CCG CTG GGC AGA CCA    4187
GGC GAA GGA GTC TGC CGT GCC ATC TAT AAA CGT TGG CCG AAC AGT TTC    4235
ACC GAT TCA GCC ACA GAG ACC GGC ACC GCA AAA CTG ACT GTG TGC CAA    4283
GGA AAG AAA GTG ATC CAC GCG GTT GGC CCT GAT TTC CGG AAA CAC CCA    4331
GAG GCA GAA GCC CTG AAA TTG CTG CAA AAC GCC TAC CAT GCA GTG GCA    4379
GAC TTA GTA AAT GAA CAT AAT ATC AAG TCT GTC GCC ATC CCA CTG CTA    4427
TCT ACA GGC ATT TAC GCA GCC GGA AAA GAC CGC CTT GAA GTA TCA CTT    4475
AAC TGC TTG ACA ACC GCG CTA GAT AGA ACT GAT GCG GAC GTA ACC ATC    4523
TAC TGC CTG GAT AAG AAG TGG AAG GAA AGA ATC GAC GCG GTG CTC CAA    4571
CTT AAG GAG TCT GTA ATA GAG CTG AAG GAT GAG GAT ATG GAG ATC GAC    4619
GAC GAG TTA GTA TGG ATC CAT CCG GAC AGT TGC CTG AAG GGA AGA AAG    4667
GGA TTC AGT ACT ACA AAA GGA AAG TTG TAT TCG TAC TTT GAA GGC ACC    4715
AAA TTC CAT CAA GCA GCA AAA GAT ATG GCG GAG ATA AAG GTC CTG TTC    4763
CCA AAT GAC CAG GAA AGC AAC GAG CAA CTG TGT GCC TAC ATA TTG GGG    4811
GAG ACC ATG GAA GCA ATC CGC GAA AAA TGC CCG GTC GAC CAC AAC CCG    4859
TCG TCT AGC CCG CCA AAA ACG CTG CCG TGC CTC TGC ATG TAT GCC ATG    4907
ACG CCA GAA AGG GTC CAC AGA CTC AGA AGC AAC AAC GTC AAA GAA GTT    4955
ACA GTA TGC TCC TCC ACC CCC TTC CCA AAG TAC AAA ATC AAG AAC GTT    5003
```

```
CAG AAG GTT CAG TGC ACA AAA GTA GTC CTG TTT AAC CCG CAT ACC CCT       5051

GCA TTC GTT CCC GCC CGT AAG TAC ATA GAA GCG CCA GAA CAG CCT GCA       5099

GCT CCG CCT GCA CAG GCC GAG GAG GCC CCC GAA GTT GCA GCA ACA CCA       5147

ACA CCA CCT GCA GCT GAT AAC ACC TCG CTT GAT GTC ACG GAC ATC TCA       5195

CTG GAC ATG GAA GAC AGT AGC GAA GGC TCA CTC TTT TCG AGC TTT AGC       5243

GGA TCG GAC AAC TCT ATT ACT AGT ATG GAC AGT TGG TCG TCA GGA CCT       5291

AGT TCA CTA GAG ATA GTA GAC CGA AGG CAG GTG GTG GTG GCT GAC GTC       5339

CAT GCC GTC CAA GAG CCT GCC CCT GTT CCA CCG CCA AGG CTA AAG AAG       5387

ATG GCC CGC CTG GCA GCG GCA AGA ATG CAG GAA GAG CCA ACT CCA CCG       5435

GCA AGC ACC AGC TCT GCG GAC GAG TCC CTT CAC CTT TCT TTT GGT GGG       5483

GTA TCC ATG TCC TTC GGA TCC CTT TTC GAC GGA GAG ATG GGC GCC TTG       5531

GCA GCG GCA CAA CCC CCG GCA AGT ACA TGC CCT ACG GAT GTG CCT ATG       5579

TCT TTC GGA TCG TTT TCC GAC GGA GAG ATT GAG GAG CTG AGC CGC AGA       5627

GTA ACC GAG TCT GAG CCC GTC CTG TTT GGG TCA TTT GAA CCG GGC GAA       5675

GTG AAC TCA ATT ATA TCG TCC CGA TCA GTT GTA TCT TTT CCA CCA CGC       5723

AAG CAG AGA CGT AGA CGC AGG AGC AGG AGG ACC GAA TAC TGA CTA ACC       5771

GGG GTA GGT GGG TAC ATA TTT TCG ACG GAC ACA GGC CCT GGG CAC TTG       5819

CAA ATG GAG TCC GTT CTG CAG AAT CAG CTT ACA GAA CCG ACC TTG GAG       5867

CGC AAT GTT CTG GAA AGA ATC TAC GCC CCG GTG CTC GAC ACG TCG AAA       5915

GAG GAA CAG CTC AAA CTC AGG TAC CAG ATG ATG CCC ACC GAA GCC AAC       5963

AAA AGC AGG TAC CAG TCT AGA AAA GTA GAA AAT CAG AAA GCC ATA ACC       6011

ACT GAG CGA CTG CTT TCA GGG CTA CGA CTG TAT AAC TCT GCC ACA GAT       6059

CAG CCA GAA TGC TAT AAG ATC ACC TAC CCG AAA CCA TCG TAT TCC AGC       6107

AGT GTA CCG GCG AAC TAC TCT GAC CCA AAG TTT GCT GTA GCT GTT TGC       6155

AAC AAC TAT CTG CAT GAG AAT TAC CCG ACG GTA GCA TCT TAT CAG ATC       6203

ACC GAC GAG TAC GAT GCT TAC TTG GAT ATG GTA GAC GGG ACA GTC GCT       6251

TGC CTA GAT ACT GCA ACT TTT TGC CCC GCC AAG CTT AGA AGT TAC CCG       6299

AAA AGA CAC GAG TAT AGA GCC CCA AAC ACT CGC AGT GCG GTT CCA TCA       6347

GCG ATG CAG AAC ACG TTG CAA AAC GTG CTC ATT GCC GCG ACT AAA AGA       6395

AAC TGC AAC GTC ACA CAA ATG CGT GAA TTG CCA ACA CTG GAC TCA GCG       6443

ACA TTC AAC GTT GAA TGC TTT CGA AAA TAT GCA TGT AAT GAC GAG TAT       6491

TGG GAG GAG TTT GCC CGA AAG CCA ATT AGG ATC ACT ACT GAG TTC GTT       6539

ACC GCA TAC GTG GCC AGA CTG AAA GGC CCT AAG GCC GCC GCA CTG TTC       6587

GCA AAG ACG CAT AAT TTG GTC CCA TTG CAA GAA GTG CCT ATG GAT AGG       6635

TTC GTC ATG GAC ATG AAA AGA GAC GTG AAA GTT ACA CCT GGC ACG AAA       6683

CAC ACA GAA GAA AGA CCG AAA GTA CAA GTG CTA CAA GCC GCA GAA CCC       6731

CTG GCG ACC GCT TAC CTG TGC GGG ATC CAC CGG GAG TTA GTG CGC AGG       6779

CTT ACA GCC GTC TTG CTA CCC AAC ATT CAC ACG CTT TTT GAC ATG TCG       6827

GCG GAG GAC TTT GAT GCA ATC ATA GCA GAA CAC TTC AAG CAA GGT GAC       6875

CCG GTA CTG GAG ACG GAT ATC GCC TCG TTC GAC AAA AGC CAA GAC GAC       6923
```

```
GCT ATG GCG TTA ACT GGC CTG ATG ATC TTG GAA GAC CTG GGT GTG GAC      6971

CAA CCA CTA CTC GAC TTG ATC GAG TGC GCC TTT GGA GAA ATA TCA TCC      7019

ACC CAT CTG CCC ACG GGT ACC CGT TTC AAA TTC GGG GCG ATG ATG AAA      7067

TCC GGA ATG TTC CTC ACG CTC TTT GTC AAC ACA GTT CTG AAT GTC GTT      7115

ATC GCC AGC AGA GTA TTG GAG GAG CGG CTT AAA ACG TCC AAA TGT GCA      7163

GCA TTT ATC GGC GAC GAC AAC ATC ATA CAC GGA GTA GTA TCT GAC AAA      7211

GAA ATG GCT GAG AGG TGT GCC ACC TGG CTC AAC ATG GAG GTT AAG ATC      7259

ATT GAC GCA GTC ATC GGC GAG AGA CCG CCT TAC TTC TGC GGT GGA TTC      7307

ATC TTG CAA GAT TCG GTT ACC TCC ACA GCG TGT CGC GTG GCG GAC CCC      7355

TTG AAA AGG CTG TTT AAG TTG GGT AAA CCG CTC CCA GCC GAC GAC GAG      7403

CAA GAC GAA GAC AGA AGA CGC GCT CTG CTA GAT GAA ACA AAG GCG TGG      7451

TTT AGA GTA GGT ATA ACA GAC ACC TTA GCA GTG GCC GTG GCA ACT CGG      7499

TAT GAG GTA GAC AAC ATC ACA CCT GTC CTG CTG GCA TTG AGA ACT TTT      7547

GCC CAG AGC AAA AGA GCA TTT CAA GCC ATC AGA GGG GAA ATA AAG CAT      7595

CTC TAC GGT GGT CCT AAA TAGTCAGCAT AGCACATTTC ATCTGACTAA             7643

TACCACAACA CCACCACC ATG AAT AGA GGA TTC TTT AAC ATG CTC GGC CGC      7694

CGC CCC TTC CCG GCC CCC ACT GCC ATG TGG AGG CCG CGG AGA AGG AGG      7742

CAG GCG GCC CCG ATG CCT GCC CGC AAT GGG CTG GCT TCC CAA ATC CAG      7790

CAA CTG ACC ACA GCC GTC AGT GCC CTA GTC ATT GGA CAG GCA ACT AGA      7838

CCT CAA ACC CCA CGC CCA CGC CCG CCG CCG CGC CAG AAG AAG CAG GCG      7886

CCA AAG CAA CCA CCG AAG CCG AAG AAA CCA AAA ACA CAG GAG AAG AAG      7934

AAG AAG CAA CCT GCA AAA CCC AAA CCC GGA AAG AGA CAA CGT ATG GCA      7982

CTC AAG TTG GAG GCC GAC AGA CTG TTC GAC GTC AAA AAT GAG GAC GGA      8030

GAT GTC ATC GGG CAC GCA CTG GCC ATG GAA GGA AAG GTA ATG AAA CCA      8078

CTC CAC GTG AAA GGA ACT ATT GAC CAC CCT GTG CTA TCA AAG CTC AAA      8126

TTC ACC AAG TCG TCA GCA TAC GAC ATG GAG TTC GCA CAG TTG CCG GTC      8174

AAC ATG AGA AGT GAG GCG TTC ACC TAC ACC AGC GAA CAC CCT GAA GGG      8222

TTT TAC AAC TGG CAC CAC GGA GCG GTG CAG TAT AGT GGA GGT AGA TTT      8270

ACC ATC CCC CGC GGA GTA GGA GGC AGA GGA GAC AGT GGT CGT CCG ATT      8318

ATG GAT AAC TCA GGC CGG GTT GTC GCG ATA GTC CTC GGA GGG GCT GAT      8366

GAG GGA ACA AGA ACT GCC CTT TCG GTC GTC ACC TGG AAT AGC AAA GGG      8414

AAG ACA ATC AAG ACA ACC CCG GAA GGG ACA GAA GAG TGG TCT GCA GCA      8462

CCA CTG GTC ACG GCC ATG TGC TTG CTT GGA AAC GTG AGC TTC CCA TGC      8510

AAT CGC CCG CCC ACA TGC TAC ACC CGC GAA CCA TCC AGA GCT CTT GAC      8558

ATC CTT GAA GAG AAC GTG AAC CAC GAG GCC TAC GAC ACC CTG CTC AAC      8606

GCC ATA TTG CGG TGC GGA TCG TCC GGC AGA AGC AAA AGA AGC GTC ACT      8654

GAC GAC TTT ACC TTG ACC AGC CCG TAC TTG GGC ACA TGC TCG TAC TGT      8702

CAC CAT ACT GAA CCG TGC TTT AGC CCG ATT AAG ATC GAG CAG GTC TGG      8750

GAT GAA GCG GAC GAC AAC ACC ATA CGC ATA CAG ACT TCC GCC CAG TTT      8798
```

```
GGA TAC GAC CAA AGC GGA GCA GCA AGC TCA AAT AAG TAC CGC TAC ATG    8846
TCG CTC GAG CAG GAT CAT ACC GTC AAA GAA GGC ACT ATG GAT GAC ATC    8894
AAG ATC AGC ACC TCA GGA CCG TGT AGA AGG CTT AGC TAC AAA GGA TAC    8942
TTT CTC CTC GCG AAG TGT CCT CCA GGG GAC AGC GTA ACG GTT AGT ATA    8990
GCG AGT AGC AAC TCA GCA ACG TCA TGC ACA ATG GCC CGC AAG ATA AAA    9038
CCA AAA TTC GTG GGA CGG GAA AAA TAT GAC CTA CCT CCC GTT CAC GGT    9086
AAG AAG ATT CCT TGC ACA GTG TAC GAC CGT CTG AAA GAA ACA ACC GCC    9134
GGC TAC ATC ACT ATG CAC AGG CCG GGA CCG CAC GCC TAT ACG TCC TAT    9182
CTG GAG GAA TCA TCA GGG AAA GTC TAC GCG AAG CCA CCA TCC GGA AAG    9230
AAC ATT ACG TAC GAG TGC AAG TGC GGC GAT TAC AAG ACC GGT ACC GTT    9278
ACG ACC CGT ACC GAA ATC ACG GGC TGC ACC GCC ATC AAG CAG TGC GTC    9326
GCC TAT AAG AGC GAC CAA ACG AAG TGG GTC TTC AAT TCG CCG GAC TTG    9374
ATC AGA CAT GCC GAC CAC ACG GCC CAA GGG AAA TTG CAT TTA CCT TTC    9422
AAG CTG ATC CCG AGT ACC TGC ATG GTC CCT GTT GCC CAC GCG CCG AAC    9470
GTA GTA CAC GGC TTT AAA CAC ATC AGC CTC CAA TTA GAC ACA GAC CAC    9518
CTG ACA TTG CTC ACC ACC AGG AGA CTA GGG GCA AAT CCG GAA CCA ACT    9566
ACT GAA TGG ATC ATC GGA AAG ACG GTT AGA AAC TTC ACC GTC GAC CGA    9614
GAT GGC CTG GAA TAC ATA TGG GGC AAT CAC GAA CCG GTA AGG GTC TAT    9662
GCC CAA GAG TCT GCA CCA GGA GAC CCT CAC GGA TGG CCA CAC GAA ATA    9710
GTA CAG CAT TAC TAC CAT CGC CAT CCT GTG TAC ACC ATC TTA GCC GTC    9758
GCA TCA GCT GCT GTG GCG ATG ATG ATT GGC GTA ACT GTT GCA GCA TTA    9806
TGT GCC TGT AAA GCG CGC CGT GAG TGC CTG ACG CCA TAT GCC CTG GCC    9854
CCA AAT GCC GTG ATT CCA ACT TCG CTG GCA CTT TTG TGC TGT GTT AGG    9902
TCG GCT AAT GCT GAA ACA TTC ACC GAG ACC ATG AGT ACC TAT GGC ACG    9950
AAC AGC CAG CCA TTC TTC TGG GTC CAG CTG TGT ATA CCC CTG GCC GCT    9998
GTC ATC GTT CTA ATG CGC TGT TGC TCA TGC TGC CTG CCT TTT TTA GTG   10046
GTT GCC GGC GCC TAC CTG GCG AAG GTA GAC GCC TAC GAA CAT GCG ACC   10094
ACT GTT CCA AAT GTG CCA CAG ATA CCG TAT AAG GCA CTT GTT GAA AGG   10142
GCA GGG TAC GCC CCG CTC AAT TTG GAG ATT ACT GTC ATG TCC TCG AGG   10190
GTT TTG CCT TCC ACC AAC CAA GAG TAC ATC ACC TGC AAA TTC ACC ACT   10238
GTG GTC CCC TCC CCT AAA GTC AAA TGC TGC GGC TCC TTG GAA TGT CAG   10286
CCC GCC GCT CAC GCA GAC TAT ACC TGC AAG GTC TTT GGA GGG GTG TAC   10334
CCC TTC ATG TGG GGA GGA GCA CAA TGT TTT TGC GAC AGT GAG AAC AGC   10382
CAG ATG AGT GAG GCG TAC GTC GAA TTG TCA GCA GAT TGC GCG ACT GAC   10430
CAC GCG CAG GCG ATT AAG GTG CAT ACT GCC GCG ATG AAA GTA GGA CTA   10478
CGT ATA GTG TAC GGG AAC ACT ACC AGT TTC CTA GAT GTG TAC GTG AAC   10526
GGA GTC ACA CCA GGA ACG TCT AAA GAC CTG AAA GTC ATA GCT GGA CCA   10574
ATT TCA GCA TCG TTT ACA CCA TTC GAT CAC AAG GTC GTT ATC CAT CGC   10622
GGC CTG GTG TAC AAC TAT GAC TTC CCG GAA TAC GGA GCG ATG AAA CCA   10670
GGA GCG TTT GGA GAC ATT CAA GCT ACC TCC TTG ACT AGC AAA GAT CTC   10718
```

```
ATC GCC AGC ACA GAC ATT AGA CTA CTC AAG CCT TCC GCC AAG AAC GTG      10766
CAT GTC CCG TAC ACG CAG GCC GCA TCT GGA TTC GAG ATG TGG AAA AAC      10814
AAC TCA GGC CGC CCA CTG CAG GAA ACC GCC CCT TTC GGG TGC AAG ATT      10862
GCA GTC AAT CCG CTT CGA GCG GTG GAC TGC TCA TAC GGG AAC ATT CCC      10910
ATC TCT ATC GAC ATC CCG AAC GCT GCC TTT ATC AGG ACA TCA GAT GCA      10958
CCA CTG GTC TCA ACA GTC AAA TGT GAT GTC AGT GAG TGC ACT TAC TCA      11006
GCG GAC TTC GGC GGG ATG GCT ACC CTG CAG TAT GTA TCC GAC CGC GAA      11054
GGA CAA TGC CCT GTA CAT TCG CAT TCG AGC ACA GCA ACC CTC CAA GAG      11102
TCG ACA GTT CAT GTC CTG GAG AAA GGA GCG GTG ACA GTA CAC TTC AGC      11150
ACC GCG AGC CCA CAG GCG AAC TTT ATT GTA TCG CTG TGT GGT AAG AAG      11198
ACA ACA TGC AAT GCA GAA TGC AAA CCA CCA GCT GAC CAT ATC GTG AGC      11246
ACC CCG CAC AAA AAT GAC CAA GAA TTC CAA GCC GCC ATC TCA AAA ACT      11294
TCA TGG AGT TGG CTG TTT GCC CTT TTC GGC GGC GCC TCG TCG CTA TTA      11342
ATT ATA GGA CTT ATG ATT TTT GCT TGC AGC ATG ATG CTG ACT AGC ACA      11390
CGA AGA TGACCGCTAC GCCCCAATGA CCCGACCAGC AAAACTCGAT GTACTTCCGA      11446
GGAACTGATG TGCATAATGC ATCAGGCTGG TATATTAGAT CCCCGCTTAC CGCGGGCAAT   11506
ATAGCAACAC CAAAACTCGA CGTATTTCCG AGGAAGCGCA GTGCATAATG CTGCGCAGTG   11566
TTGCCAAATA ATCACTATAT TAACCATTTA TTTAGCGGAC GCCAAAACTC AATGTATTTC   11626
TGAGGAAGCA TGGTGCATAA TGCCATGCAG CGTCTGCATA ACTTTTTATT ATTTCTTTTA   11686
TTAATCAACA AAATTTTGTT TTTAACATTT N                                   11717
```

(2) INFORMATION FOR SEQ ID NO:5:

(i) SEQUENCE CHARACTERISTICS:
        (A) LENGTH: 2517 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Lys Pro Val Val Asn Val Asp Val Asp Pro Gln Ser Pro Phe
 1               5                  10                  15

Val Val Gln Leu Gln Lys Ser Phe Pro Gln Phe Glu Val Val Ala Gln
            20                  25                  30

Gln Val Thr Pro Asn Asp His Ala Asn Ala Arg Ala Phe Ser His Leu
        35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140
```

-continued

```
Thr Arg Ala Glu Tyr Ser Val Met Gln Asp Val Tyr Ile Asn Ala Pro
145                 150                 155                 160
Gly Thr Ile Tyr His Gln Ala Met Lys Gly Val Arg Thr Leu Tyr Trp
                165                 170                 175
Ile Gly Phe Asp Thr Thr Gln Phe Met Phe Ser Ala Met Ala Gly Ser
            180                 185                 190
Tyr Pro Ala Tyr Asn Thr Asn Trp Ala Asp Glu Lys Val Leu Glu Ala
        195                 200                 205
Arg Asn Ile Gly Leu Cys Ser Thr Lys Leu Ser Glu Gly Arg Thr Gly
210                 215                 220
Lys Leu Ser Ile Met Arg Lys Lys Glu Leu Lys Pro Gly Ser Arg Val
225                 230                 235                 240
Tyr Phe Ser Val Gly Ser Thr Leu Tyr Pro Glu His Arg Ala Ser Leu
                245                 250                 255
Gln Ser Trp His Leu Pro Ser Val Phe His Leu Lys Gly Lys Gln Ser
                260                 265                 270
Tyr Thr Cys Arg Cys Asp Thr Val Val Ser Cys Glu Gly Tyr Val Val
            275                 280                 285
Lys Lys Ile Thr Ile Ser Pro Gly Ile Thr Gly Glu Thr Val Gly Tyr
        290                 295                 300
Ala Val Thr Asn Asn Ser Glu Gly Phe Leu Leu Cys Lys Val Thr Asp
305                 310                 315                 320
Thr Val Lys Gly Glu Arg Val Ser Phe Pro Val Cys Thr Tyr Ile Pro
                325                 330                 335
Ala Thr Ile Cys Asp Gln Met Thr Gly Ile Met Ala Thr Asp Ile Ser
                340                 345                 350
Pro Asp Asp Ala Gln Lys Leu Leu Val Gly Leu Asn Gln Arg Ile Val
            355                 360                 365
Ile Asn Gly Lys Thr Asn Arg Asn Thr Asn Thr Met Gln Asn Tyr Leu
        370                 375                 380
Leu Pro Ile Ile Ala Gln Gly Phe Ser Lys Trp Ala Lys Glu Arg Lys
385                 390                 395                 400
Glu Asp Leu Asp Asn Glu Lys Met Leu Gly Thr Arg Glu Arg Lys Leu
                405                 410                 415
Thr Tyr Gly Cys Leu Trp Ala Phe Arg Thr Lys Lys Val His Ser Phe
                420                 425                 430
Tyr Arg Pro Pro Gly Thr Gln Thr Ile Val Lys Val Pro Ala Ser Phe
            435                 440                 445
Ser Ala Phe Pro Met Ser Ser Val Trp Thr Thr Ser Leu Pro Met Ser
450                 455                 460
Leu Arg Gln Lys Ile Lys Leu Ala Leu Gln Pro Lys Lys Glu Glu Lys
465                 470                 475                 480
Leu Leu Gln Val Pro Glu Glu Leu Val Met Glu Ala Lys Ala Ala Phe
                485                 490                 495
Glu Asp Ala Gln Glu Glu Ser Arg Ala Glu Lys Leu Arg Glu Ala Leu
            500                 505                 510
Pro Pro Leu Val Ala Asp Lys Gly Ile Glu Ala Ala Glu Val Val
        515                 520                 525
Cys Glu Val Glu Gly Leu Gln Ala Asp Ile Gly Ala Ala Leu Val Glu
530                 535                 540
Thr Pro Arg Gly His Val Arg Ile Ile Pro Gln Ala Asn Asp Arg Met
545                 550                 555                 560
```

-continued

```
Ile Gly Gln Tyr Ile Val Val Ser Pro Thr Ser Val Leu Lys Asn Ala
                565                 570                 575
Lys Leu Ala Pro Ala His Pro Leu Ala Asp Gln Val Lys Ile Ile Thr
            580                 585                 590
His Ser Gly Arg Ser Gly Arg Tyr Ala Val Glu Pro Tyr Asp Ala Lys
        595                 600                 605
Val Leu Met Pro Ala Gly Ser Ala Val Pro Trp Pro Glu Phe Leu Ala
    610                 615                 620
Leu Ser Glu Ser Ala Thr Leu Val Tyr Asn Glu Arg Glu Phe Val Asn
625                 630                 635                 640
Arg Lys Leu Tyr His Ile Ala Met His Gly Pro Ala Lys Asn Thr Glu
                645                 650                 655
Glu Glu Gln Tyr Lys Val Thr Lys Ala Glu Leu Ala Glu Thr Glu Tyr
            660                 665                 670
Val Phe Asp Val Asp Lys Lys Arg Cys Val Lys Lys Glu Glu Ala Ser
        675                 680                 685
Gly Leu Val Leu Ser Gly Glu Leu Thr Asn Pro Pro Tyr His Glu Leu
    690                 695                 700
Ala Leu Glu Gly Leu Lys Thr Arg Pro Val Val Pro Tyr Lys Val Glu
705                 710                 715                 720
Thr Ile Gly Val Ile Gly Ala Pro Gly Ser Gly Lys Ser Ala Ile Ile
                725                 730                 735
Lys Ser Thr Val Thr Ala Arg Asp Leu Val Thr Ser Gly Lys Lys Glu
            740                 745                 750
Asn Cys Arg Glu Ile Gln Ala Asp Val Leu Arg Leu Arg Gly Met Gln
        755                 760                 765
Ile Thr Ser Lys Thr Val Asp Ser Val Met Leu Asn Gly Cys Arg Lys
    770                 775                 780
Ala Val Glu Val Leu Tyr Val Asp Glu Ala Phe Ala Cys His Ala Gly
785                 790                 795                 800
Ala Leu Leu Ala Leu Ile Ala Ile Val Arg Pro Arg His Lys Val Val
                805                 810                 815
Leu Cys Gly Asp Pro Lys Gln Cys Gly Phe Phe Asn Met Met Gln Leu
            820                 825                 830
Lys Val Tyr Phe Asn His Pro Glu Lys Asp Ile Cys Thr Lys Thr Phe
        835                 840                 845
Tyr Lys Phe Ile Ser Arg Arg Cys Thr Gln Pro Val Thr Ala Ile Val
    850                 855                 860
Ser Thr Leu His Tyr Asp Gly Lys Met Lys Thr Thr Asn Pro Cys Lys
865                 870                 875                 880
Lys Asn Ile Glu Ile Asp Ile Thr Gly Ala Thr Lys Pro Lys Pro Gly
                885                 890                 895
Asp Ile Ile Leu Thr Cys Phe Arg Gly Trp Val Lys Gln Leu Gln Ile
            900                 905                 910
Asp Tyr Pro Gly His Glu Val Met Thr Ala Ala Ser Gln Gly Leu
        915                 920                 925
Thr Arg Lys Gly Val Tyr Ala Val Arg Gln Lys Val Asn Glu Asn Pro
    930                 935                 940
Leu Tyr Ala Ile Thr Ser Glu His Val Asn Val Leu Leu Thr Arg Thr
945                 950                 955                 960
Glu Asp Arg Leu Val Trp Lys Thr Leu Gln Gly Asp Pro Trp Ile Lys
                965                 970                 975
Gln Leu Thr Asn Val Pro Lys Gly Asn Phe Gln Ala Thr Ile Glu Asp
```

-continued

```
                        980                 985                 990
Trp Glu Ala Glu His Lys Gly Ile Ile Ala Ala Ile Asn Ser Pro Ala
            995                1000               1005

Pro Arg Thr Asn Pro Phe Ser Cys Lys Thr Asn Val Cys Trp Ala Lys
           1010                1015               1020

Arg Leu Glu Pro Ile Leu Ala Thr Ala Gly Ile Val Leu Thr Gly Cys
1025               1030                1035               1040

Gln Trp Ser Glu Leu Phe Pro Gln Phe Ala Asp Asp Lys Pro His Ser
                1045               1050               1055

Ala Ile Tyr Ala Leu Asp Val Ile Cys Ile Lys Phe Phe Gly Met Asp
            1060               1065                1070

Leu Thr Ser Gly Leu Phe Ser Lys Gln Ser Ile Pro Leu Thr Tyr His
            1075               1080                1085

Pro Ala Asp Ser Ala Arg Pro Val Ala His Trp Asp Asn Ser Pro Gly
1090                1095               1100

Thr Arg Lys Tyr Gly Tyr Asp His Ala Val Ala Ala Glu Leu Ser Arg
1105                1110               1115                1120

Arg Phe Pro Val Phe Gln Leu Ala Gly Lys Gly Thr Gln Leu Asp Leu
                1125               1130                1135

Gln Thr Gly Arg Thr Arg Val Ile Ser Ala Gln His Asn Leu Val Pro
                1140               1145                1150

Val Asn Arg Asn Leu Pro His Ala Leu Val Pro Glu His Lys Glu Lys
            1155               1160                1165

Gln Pro Gly Pro Val Lys Lys Phe Leu Ser Gln Phe Lys His His Ser
            1170               1175                1180

Val Leu Val Val Ser Glu Glu Lys Ile Glu Ala Pro His Lys Arg Ile
1185                1190               1195                1200

Glu Trp Ile Ala Pro Ile Gly Ile Ala Gly Ala Asp Lys Asn Tyr Asn
                1205               1210                1215

Leu Ala Phe Gly Phe Pro Pro Gln Ala Arg Tyr Asp Leu Val Phe Ile
                1220               1225                1230

Asn Ile Gly Thr Lys Tyr Arg Asn His His Phe Gln Gln Cys Glu Asp
            1235               1240                1245

His Ala Ala Thr Leu Lys Thr Leu Ser Arg Ser Ala Leu Asn Cys Leu
            1250               1255                1260

Asn Pro Gly Gly Thr Leu Val Val Lys Ser Tyr Gly Tyr Ala Asp Arg
1265                1270               1275                1280

Asn Ser Glu Asp Val Val Thr Ala Leu Ala Arg Lys Phe Val Arg Val
                1285               1290                1295

Ser Ala Ala Arg Pro Glu Cys Val Ser Ser Asn Thr Glu Met Tyr Leu
                1300               1305                1310

Ile Phe Arg Gln Leu Asp Asn Ser Arg Thr Arg Gln Phe Thr Pro His
            1315               1320                1325

His Leu Asn Cys Val Ile Ser Ser Val Tyr Glu Gly Thr Arg Asp Gly
            1330               1335                1340

Val Gly Ala Ala Pro Ser Tyr Arg Thr Lys Arg Glu Asn Ile Ala Asp
1345                1350               1355                1360

Cys Gln Glu Glu Ala Val Val Asn Ala Ala Asn Pro Leu Gly Arg Pro
                1365               1370                1375

Gly Glu Gly Val Cys Arg Ala Ile Tyr Lys Arg Trp Pro Asn Ser Phe
                1380               1385                1390

Thr Asp Ser Ala Thr Glu Thr Gly Thr Ala Lys Leu Thr Val Cys Gln
            1395               1400                1405
```

-continued

```
Gly Lys Lys Val Ile His Ala Val Gly Pro Asp Phe Arg Lys His Pro
    1410                1415                1420
Glu Ala Glu Ala Leu Lys Leu Leu Gln Asn Ala Tyr His Ala Val Ala
1425                1430                1435                1440
Asp Leu Val Asn Glu His Asn Ile Lys Ser Val Ala Ile Pro Leu Leu
                1445                1450                1455
Ser Thr Gly Ile Tyr Ala Ala Gly Lys Asp Arg Leu Glu Val Ser Leu
                1460                1465                1470
Asn Cys Leu Thr Thr Ala Leu Asp Arg Thr Asp Ala Asp Val Thr Ile
            1475                1480                1485
Tyr Cys Leu Asp Lys Lys Trp Lys Glu Arg Ile Asp Ala Val Leu Gln
            1490                1495                1500
Leu Lys Glu Ser Val Ile Glu Leu Lys Asp Glu Asp Met Glu Ile Asp
1505                1510                1515                1520
Asp Glu Leu Val Trp Ile His Pro Asp Ser Cys Leu Lys Gly Arg Lys
                1525                1530                1535
Gly Phe Ser Thr Thr Lys Gly Leu Tyr Ser Tyr Phe Glu Gly Thr
                1540                1545                1550
Lys Phe His Gln Ala Ala Lys Asp Met Ala Glu Ile Lys Val Leu Phe
            1555                1560                1565
Pro Asn Asp Gln Glu Ser Asn Glu Gln Leu Cys Ala Tyr Ile Leu Gly
            1570                1575                1580
Glu Thr Met Glu Ala Ile Arg Gly Lys Cys Pro Val Asp His Asn Pro
1585                1590                1595                1600
Ser Ser Ser Pro Pro Lys Thr Leu Pro Cys Leu Cys Met Tyr Ala Met
                1605                1610                1615
Thr Pro Glu Arg Val His Arg Leu Arg Ser Asn Asn Val Lys Glu Val
                1620                1625                1630
Thr Val Cys Ser Ser Thr Pro Leu Pro Lys Tyr Lys Ile Lys Asn Val
            1635                1640                1645
Gln Lys Val Gln Cys Thr Lys Val Val Leu Phe Asn Pro His Thr Pro
            1650                1655                1660
Ala Phe Val Pro Ala Arg Lys Tyr Ile Glu Ala Pro Glu Gln Pro Ala
1665                1670                1675                1680
Ala Pro Pro Ala Gln Ala Glu Glu Ala Pro Glu Val Ala Ala Thr Pro
                1685                1690                1695
Thr Pro Pro Ala Ala Asp Asn Thr Ser Leu Asp Val Thr Asp Ile Ser
                1700                1705                1710
Leu Asp Met Glu Asp Ser Ser Gly Ser Leu Phe Ser Ser Phe Ser
            1715                1720                1725
Gly Ser Asp Asn Ser Ile Thr Ser Met Asp Ser Trp Ser Ser Gly Pro
            1730                1735                1740
Ser Ser Leu Glu Ile Val Asp Arg Arg Gln Val Val Ala Asp Val
1745                1750                1755                1760
His Ala Val Gln Glu Pro Ala Pro Val Pro Pro Arg Leu Lys Lys
                1765                1770                1775
Met Ala Arg Leu Ala Ala Ala Arg Met Gln Glu Glu Pro Thr Pro Pro
            1780                1785                1790
Ala Ser Thr Ser Ser Ala Asp Glu Ser Leu His Leu Ser Phe Gly Gly
            1795                1800                1805
Val Ser Met Ser Phe Gly Ser Leu Phe Asp Gly Glu Met Gly Ala Leu
            1810                1815                1820
```

```
Ala Ala Ala Gln Pro Pro Ala Ser Thr Cys Pro Thr Asp Val Pro Met
1825                1830                1835                1840

Ser Phe Gly Ser Phe Ser Asp Gly Glu Ile Glu Glu Leu Ser Arg Arg
            1845                1850                1855

Val Thr Glu Ser Glu Pro Val Leu Phe Gly Ser Phe Glu Pro Gly Glu
            1860                1865                1870

Val Asn Ser Ile Ile Ser Ser Arg Ser Val Val Ser Phe Pro Pro Arg
            1875                1880                1885

Lys Gln Arg Arg Arg Arg Arg Ser Arg Arg Thr Glu Tyr Leu Thr Gly
            1890                1895                1900

Val Gly Gly Tyr Ile Phe Ser Thr Asp Thr Gly Pro Gly His Leu Gln
1905                1910                1915                1920

Met Glu Ser Val Leu Gln Asn Gln Leu Thr Glu Pro Thr Leu Glu Arg
                1925                1930                1935

Asn Val Leu Glu Arg Ile Tyr Ala Pro Val Leu Asp Thr Ser Lys Glu
                1940                1945                1950

Glu Gln Leu Lys Leu Arg Tyr Gln Met Met Pro Thr Glu Ala Asn Lys
                1955                1960                1965

Ser Arg Tyr Gln Ser Arg Lys Val Glu Asn Gln Lys Ala Ile Thr Thr
                1970                1975                1980

Glu Arg Leu Leu Ser Gly Leu Arg Leu Tyr Asn Ser Ala Thr Asp Gln
1985                1990                1995                2000

Pro Glu Cys Tyr Lys Ile Thr Tyr Pro Lys Pro Ser Tyr Ser Ser Ser
                2005                2010                2015

Val Pro Ala Asn Tyr Ser Asp Pro Lys Phe Ala Val Ala Val Cys Asn
                2020                2025                2030

Asn Tyr Leu His Glu Asn Tyr Pro Thr Val Ala Ser Tyr Gln Ile Thr
                2035                2040                2045

Asp Glu Tyr Asp Ala Tyr Leu Asp Met Val Asp Gly Thr Val Ala Cys
                2050                2055                2060

Leu Asp Thr Ala Thr Phe Cys Pro Ala Lys Leu Arg Ser Tyr Pro Lys
2065                2070                2075                2080

Arg His Glu Tyr Arg Ala Pro Asn Thr Arg Ser Ala Val Pro Ser Ala
                2085                2090                2095

Met Gln Asn Thr Leu Gln Asn Val Leu Ile Ala Ala Thr Lys Arg Asn
                2100                2105                2110

Cys Asn Val Thr Gln Met Arg Glu Leu Pro Thr Leu Asp Ser Ala Thr
                2115                2120                2125

Phe Asn Val Glu Cys Phe Arg Lys Tyr Ala Cys Asn Asp Glu Tyr Trp
            2130                2135                2140

Glu Glu Phe Ala Arg Lys Pro Ile Arg Ile Thr Thr Glu Phe Val Thr
2145                2150                2155                2160

Ala Tyr Val Ala Arg Leu Lys Gly Pro Lys Ala Ala Ala Leu Phe Ala
                2165                2170                2175

Lys Thr His Asn Leu Val Pro Leu Gln Glu Val Pro Met Asp Arg Phe
                2180                2185                2190

Val Met Asp Met Lys Arg Asp Val Lys Val Thr Pro Gly Thr Lys His
            2195                2200                2205

Thr Glu Glu Arg Pro Lys Val Gln Val Leu Gln Ala Ala Glu Pro Leu
        2210                2215                2220

Ala Thr Ala Tyr Leu Cys Gly Ile His Arg Glu Leu Val Arg Arg Leu
2225                2230                2235                2240

Thr Ala Val Leu Leu Pro Asn Ile His Thr Leu Phe Asp Met Ser Ala
```

```
                  2245               2250               2255

Glu Asp Phe Asp Ala Ile Ile Ala Glu His Phe Lys Gln Gly Asp Pro
                2260               2265               2270

Val Leu Glu Thr Asp Ile Ala Ser Phe Asp Lys Ser Gln Asp Ala
        2275               2280               2285

Met Ala Leu Thr Gly Leu Met Ile Leu Glu Asp Leu Gly Val Asp Gln
        2290               2295               2300

Pro Leu Leu Asp Leu Ile Glu Cys Ala Phe Gly Glu Ile Ser Ser Thr
2305               2310               2315               2320

His Leu Pro Thr Gly Thr Arg Phe Lys Phe Gly Ala Met Met Lys Ser
                2325               2330               2335

Gly Met Phe Leu Thr Leu Phe Val Asn Thr Val Leu Asn Val Val Ile
                2340               2345               2350

Ala Ser Arg Val Leu Glu Glu Arg Leu Lys Thr Ser Lys Cys Ala Ala
                2355               2360               2365

Phe Ile Gly Asp Asp Asn Ile Ile His Gly Val Val Ser Asp Lys Glu
        2370               2375               2380

Met Ala Glu Arg Cys Ala Thr Trp Leu Asn Met Glu Val Lys Ile Ile
2385               2390               2395               2400

Asp Ala Val Ile Gly Glu Arg Pro Pro Tyr Phe Cys Gly Gly Phe Ile
                2405               2410               2415

Leu Gln Asp Ser Val Thr Ser Thr Ala Cys Arg Val Ala Asp Pro Leu
                2420               2425               2430

Lys Arg Leu Phe Lys Leu Gly Lys Pro Leu Pro Ala Asp Asp Glu Gln
                2435               2440               2445

Asp Glu Asp Arg Arg Arg Ala Leu Leu Asp Glu Thr Lys Ala Trp Phe
        2450               2455               2460

Arg Val Gly Ile Thr Asp Thr Leu Ala Val Ala Val Ala Thr Arg Tyr
2465               2470               2475               2480

Glu Val Asp Asn Ile Thr Pro Val Leu Leu Ala Leu Arg Thr Phe Ala
                2485               2490               2495

Gln Ser Lys Arg Ala Phe Gln Ala Ile Arg Gly Glu Ile Lys His Leu
                2500               2505               2510

Tyr Gly Gly Pro Lys
        2515

(2) INFORMATION FOR SEQ ID NO:6:

(i) SEQUENCE CHARACTERISTICS:
        (A) LENGTH: 1245 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Arg Gly Phe Phe Asn Met Leu Gly Arg Arg Pro Phe Pro Ala
 1               5                  10                  15

Pro Thr Ala Met Trp Arg Pro Arg Arg Arg Gln Ala Ala Pro Met
            20                  25                  30

Pro Ala Arg Asn Gly Leu Ala Ser Gln Ile Gln Gln Leu Thr Thr Ala
        35                  40                  45

Val Ser Ala Leu Val Ile Gly Gln Ala Thr Arg Pro Gln Thr Pro Arg
    50                  55                  60

Pro Arg Pro Pro Arg Gln Lys Lys Gln Ala Pro Lys Gln Pro Pro
65                  70                  75                  80
```

-continued

```
Lys Pro Lys Lys Pro Lys Thr Gln Glu Lys Lys Lys Gln Pro Ala
                 85                  90                  95
Lys Pro Lys Pro Gly Lys Arg Gln Arg Met Ala Leu Lys Leu Glu Ala
            100                 105                 110
Asp Arg Leu Phe Asp Val Lys Asn Glu Asp Gly Asp Val Ile Gly His
            115                 120                 125
Ala Leu Ala Met Glu Gly Lys Val Met Lys Pro Leu His Val Lys Gly
        130                 135                 140
Thr Ile Asp His Pro Val Leu Ser Lys Leu Lys Phe Thr Lys Ser Ser
145                 150                 155                 160
Ala Tyr Asp Met Glu Phe Ala Gln Leu Pro Val Asn Met Arg Ser Glu
                165                 170                 175
Ala Phe Thr Tyr Thr Ser Glu His Pro Glu Gly Phe Tyr Asn Trp His
                180                 185                 190
His Gly Ala Val Gln Tyr Ser Gly Gly Arg Phe Thr Ile Pro Arg Gly
            195                 200                 205
Val Gly Gly Arg Gly Asp Ser Gly Arg Pro Ile Met Asp Asn Ser Gly
        210                 215                 220
Arg Val Val Ala Ile Val Leu Gly Gly Ala Asp Glu Gly Thr Arg Thr
225                 230                 235                 240
Ala Leu Ser Val Val Thr Trp Asn Ser Lys Gly Lys Thr Ile Lys Thr
                245                 250                 255
Thr Pro Glu Gly Thr Glu Glu Trp Ser Ala Ala Pro Leu Val Thr Ala
                260                 265                 270
Met Cys Leu Leu Gly Asn Val Ser Phe Pro Cys Asn Arg Pro Pro Thr
            275                 280                 285
Cys Tyr Thr Arg Glu Pro Ser Arg Ala Leu Asp Ile Leu Glu Glu Asn
        290                 295                 300
Val Asn His Glu Ala Tyr Asp Thr Leu Leu Asn Ala Ile Leu Arg Cys
305                 310                 315                 320
Gly Ser Ser Gly Arg Ser Lys Arg Ser Val Thr Asp Asp Phe Thr Leu
                325                 330                 335
Thr Ser Pro Tyr Leu Gly Thr Cys Ser Tyr Cys His His Thr Glu Pro
                340                 345                 350
Cys Phe Ser Pro Ile Lys Ile Glu Gln Val Trp Asp Glu Ala Asp Asp
            355                 360                 365
Asn Thr Ile Arg Ile Gln Thr Ser Ala Gln Phe Gly Tyr Asp Gln Ser
        370                 375                 380
Gly Ala Ala Ser Ser Asn Lys Tyr Arg Tyr Met Ser Leu Glu Gln Asp
385                 390                 395                 400
His Thr Val Lys Glu Gly Thr Met Asp Asp Ile Lys Ile Ser Thr Ser
                405                 410                 415
Gly Pro Cys Arg Arg Leu Ser Tyr Lys Gly Tyr Phe Leu Leu Ala Lys
            420                 425                 430
Cys Pro Pro Gly Asp Ser Val Thr Val Ser Ile Ala Ser Ser Asn Ser
        435                 440                 445
Ala Thr Ser Cys Thr Met Ala Arg Lys Ile Lys Pro Lys Phe Val Gly
        450                 455                 460
Arg Glu Lys Tyr Asp Leu Pro Pro Val His Gly Lys Lys Ile Pro Cys
465                 470                 475                 480
Thr Val Tyr Asp Arg Leu Lys Glu Thr Thr Ala Gly Tyr Ile Thr Met
                485                 490                 495
```

-continued

```
His Arg Pro Gly Pro His Ala Tyr Thr Ser Tyr Leu Glu Glu Ser Ser
            500                 505                 510

Gly Lys Val Tyr Ala Lys Pro Pro Ser Gly Lys Asn Ile Thr Tyr Glu
            515                 520                 525

Cys Lys Cys Gly Asp Tyr Lys Thr Gly Thr Val Thr Thr Arg Thr Glu
            530                 535                 540

Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Leu Ile Arg His Ala Asp
            565                 570                 575

His Thr Ala Gln Gly Lys Leu His Leu Pro Phe Lys Leu Ile Pro Ser
            580                 585                 590

Thr Cys Met Val Pro Val Ala His Ala Pro Asn Val Val His Gly Phe
            595                 600                 605

Lys His Ile Ser Leu Gln Leu Asp Thr Asp His Leu Thr Leu Leu Thr
            610                 615                 620

Thr Arg Arg Leu Gly Ala Asn Pro Glu Pro Thr Thr Glu Trp Ile Ile
625                 630                 635                 640

Gly Lys Thr Val Arg Asn Phe Thr Val Asp Arg Asp Gly Leu Glu Tyr
            645                 650                 655

Ile Trp Gly Asn His Glu Pro Val Arg Val Tyr Ala Gln Glu Ser Ala
            660                 665                 670

Pro Gly Asp Pro His Gly Trp Pro His Glu Ile Val Gln His Tyr Tyr
            675                 680                 685

His Arg His Pro Val Tyr Thr Ile Leu Ala Val Ala Ser Ala Ala Val
            690                 695                 700

Ala Met Met Ile Gly Val Thr Val Ala Ala Leu Cys Ala Cys Lys Ala
705                 710                 715                 720

Arg Arg Glu Cys Leu Thr Pro Tyr Ala Leu Ala Pro Asn Ala Val Ile
            725                 730                 735

Pro Thr Ser Leu Ala Leu Leu Cys Cys Val Arg Ser Ala Asn Ala Glu
            740                 745                 750

Thr Phe Thr Glu Thr Met Ser Tyr Leu Trp Ser Asn Ser Gln Pro Phe
            755                 760                 765

Phe Trp Val Gln Leu Cys Ile Pro Leu Ala Ala Val Ile Val Leu Met
            770                 775                 780

Arg Cys Cys Ser Cys Cys Leu Pro Phe Leu Val Val Ala Gly Ala Tyr
785                 790                 795                 800

Leu Ala Lys Val Asp Ala Tyr Glu His Ala Thr Thr Val Pro Asn Val
            805                 810                 815

Pro Gln Ile Pro Tyr Lys Ala Leu Val Glu Arg Ala Gly Tyr Ala Pro
            820                 825                 830

Leu Asn Leu Glu Ile Thr Val Met Ser Ser Glu Val Leu Pro Ser Thr
            835                 840                 845

Asn Gln Glu Tyr Ile Thr Cys Lys Phe Thr Thr Val Val Pro Ser Pro
            850                 855                 860

Lys Val Lys Cys Cys Gly Ser Leu Glu Cys Gln Pro Ala Ala His Ala
865                 870                 875                 880

Asp Tyr Thr Cys Lys Val Phe Gly Gly Val Tyr Pro Phe Met Trp Gly
            885                 890                 895

Gly Ala Gln Cys Phe Cys Asp Ser Glu Asn Ser Gln Met Ser Glu Ala
            900                 905                 910

Tyr Val Glu Leu Ser Ala Asp Cys Ala Thr Asp His Ala Gln Ala Ile
```

```
                      915                 920                 925
Lys Val His Thr Ala Met Lys Val Gly Leu Arg Ile Val Tyr Gly
            930                 935                 940

Asn Thr Thr Ser Phe Leu Asp Val Tyr Val Asn Gly Val Thr Pro Gly
945                 950                 955                 960

Thr Ser Lys Asp Leu Lys Val Ile Ala Gly Pro Ile Ser Ala Ser Phe
                965                 970                 975

Thr Pro Phe Asp His Lys Val Val Ile His Arg Gly Leu Val Tyr Asn
                980                 985                 990

Tyr Asp Phe Pro Glu Tyr Gly Ala Met Lys Pro Gly Ala Phe Gly Asp
            995                 1000                1005

Ile Gln Ala Thr Ser Leu Thr Ser Lys Asp Leu Ile Ala Ser Thr Asp
    1010                1015                1020

Ile Arg Leu Leu Lys Pro Ser Ala Lys Asn Val His Val Pro Tyr Thr
1025                1030                1035                1040

Gln Ala Ala Ser Gly Phe Glu Met Trp Lys Asn Asn Ser Gly Arg Pro
                1045                1050                1055

Leu Gln Glu Thr Ala Pro Phe Gly Cys Lys Ile Ala Val Asn Pro Leu
                1060                1065                1070

Arg Ala Val Asp Cys Ser Tyr Gly Asn Ile Pro Ile Ser Ile Asp Ile
                1075                1080                1085

Pro Asn Ala Ala Phe Ile Arg Thr Ser Asp Ala Pro Leu Val Ser Thr
    1090                1095                1100

Val Lys Cys Asp Val Ser Glu Cys Thr Tyr Ser Ala Asp Phe Gly Gly
1105                1110                1115                1120

Met Ala Thr Leu Gln Tyr Val Ser Asp Arg Glu Gly Gln Cys Pro Val
                1125                1130                1135

His Ser His Ser Ser Thr Ala Thr Leu Gln Glu Ser Thr Val His Val
                1140                1145                1150

Leu Glu Lys Gly Ala Val Thr Val His Phe Ser Thr Ala Ser Pro Gln
                1155                1160                1165

Ala Asn Phe Ile Val Ser Leu Cys Gly Lys Lys Thr Thr Cys Asn Ala
    1170                1175                1180

Glu Cys Lys Pro Pro Ala Asp His Ile Val Ser Thr Pro His Lys Asn
1185                1190                1195                1200

Asp Gln Glu Phe Gln Ala Ala Ile Ser Lys Thr Ser Trp Ser Trp Leu
                1205                1210                1215

Phe Ala Leu Phe Gly Gly Ala Ser Ser Leu Leu Ile Ile Gly Leu Met
                1220                1225                1230

Ile Phe Ala Cys Ser Met Met Leu Thr Ser Thr Arg Arg
                1235                1240                1245

(2) INFORMATION FOR SEQ ID NO:7:

(i) SEQUENCE CHARACTERISTICS:
        (A) LENGTH: 11663 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

ATTGGCGGCG TAGTACACAC TATTGAATCA AACAGCCGAC CAATTGCACT ACCATCACAA      60

TGGAGAAGCC AGTAGTTAAC GTAGACGTAG ACCCTCAGAG TCCGTTTGTC GTGCAACTGC     120
```

-continued

| | |
|---|---|
| AAAAGAGCTT CCCGCAATTT GAGGTAGTAG CACAGCAGGT CACTCCAAAT GACCATGCTA | 180 |
| ATGCCAGAGC ATTTTCGCAT CTGGCCAGTA AACTGATCGA GCTGGAGGTT CCTACCACAG | 240 |
| CGACGATTTT GGACATAGGC AGCGCACCGG CTCGTAGAAT GTTTTCCGAG CACCAGTACC | 300 |
| ATTGCGTTTG CCCCATGCGT AGTCCAGAAG ACCCGGACCG CATGATGAAA TATGCCAGCA | 360 |
| AACTGGCGGA AAAAGCATGT AAGATTACAA ACAAGAACTT GCATGAGAAG ATCAAGGACC | 420 |
| TCCGGACCGT ACTTGATACA CCGGATGCTG AAACGCCATC ACTCTGCTTC CACAACGATG | 480 |
| TTACCTGCAA CACGCGTGCC GAGTACTCCG TCATGCAGGA CGTGTACATC AACGCTCCCG | 540 |
| GAACTATTTA CCACCAGGCT ATGAAAGGCG TGCGGACCCT GTACTGGATT GGCTTCGACA | 600 |
| CCACCCAGTT CATGTTCTCG GCTATGGCAG GTTCGTACCC TGCATACAAC ACCAACTGGG | 660 |
| CCGACGAAAA AGTCCTTGAA GCGCGTAACA TCGGACTCTG CAGCACAAAG CTGAGTGAAG | 720 |
| GCAGGACAGG AAAGTTGTCG ATAATGAGGA AGAAGGAGTT GAAGCCCGGG TCACGGGTTT | 780 |
| ATTTCTCCGT TGGATCGACA CTTTACCCAG AACACAGAGC CAGCTTGCAG AGCTGGCATC | 840 |
| TTCCATCGGT GTTCCACTTG AAAGGAAAGC AGTCGTACAC TTGCCGCTGT GATACAGTGG | 900 |
| TGAGCTGCGA AGGCTACGTA GTGAAGAAAA TCACCATCAG TCCCGGGATC ACGGGAGAAA | 960 |
| CCGTGGGATA CGCGGTTACA AACAATAGCG AGGGCTTCTT GCTATGCAAA GTTACCGATA | 1020 |
| CAGTAAAAGG AGAACGGGTA TCGTTCCCCG TGTGCACGTA TATCCCGGCC ACCATATGCG | 1080 |
| ATCAGATGAC CGGCATAATG GCCACGGATA TCTCACCTGA CGATGCACAA AAACTTCTGG | 1140 |
| TTGGGCTCAA CCAGCGAATC GTCATTAACG GTAAGACTAA CAGGAACACC AATACCATGC | 1200 |
| AAAATTACCT TCTGCCAATC ATTGCACAAG GGTTCAGCAA ATGGGCCAAG GAGCGCAAAG | 1260 |
| AAGATCTTGA CAATGAAAAA ATGCTGGGCA CCAGAGAGCG CAAGCTTACA TATGGCTGCT | 1320 |
| TGTGGGCGTT TCGCACTAAG AAAGTGCACT CGTTCTATCG CCCACCTGGA ACGCAGACCA | 1380 |
| TCGTAAAAGT CCCAGCCTCT TTTAGCGCTT TCCCCATGTC ATCCGTATGG ACTACCTCTT | 1440 |
| TGCCCATGTC GCTGAGGCAG AAGATGAAAT TGGCATTACA ACCAAAGAAG GAGGAAAAAC | 1500 |
| TGCTGCAAGT CCCGGAGGAA TTAGTTATGG AGGCCAAGGC TGCTTTCGAG GATGCTCAGG | 1560 |
| AGGAATCCAG AGCGGAGAAG CTCCGAGAAG CACTCCCACC ATTAGTGGCA GACAAAGGTA | 1620 |
| TCGAGGCAGC TGCGGAAGTT GTCTGCGAAG TGGAGGGGCT CCAGGCGGAC ACCGGAGCAG | 1680 |
| CACTCGTCGA AACCCCGCGC GGTCATGTAA GGATAATACC TCAAGCAAAT GACCGTATGA | 1740 |
| TCGGACAGTA TATCGTTGTC TCGCCGATCT CTGTGCTGAA GAACGCTAAA CTCGCACCAG | 1800 |
| CACACCCGCT AGCAGACCAG GTTAAGATCA TAACGCACTC CGGAAGATCA GGAAGGTATG | 1860 |
| CAGTCGAACC ATACGACGCT AAAGTACTGA TGCCAGCAGG AAGTGCCGTA CCATGGCCAG | 1920 |
| AATTCTTAGC ACTGAGTGAG AGCGCCACGC TTGTGTACAA CGAAAGAGAG TTTGTGAACC | 1980 |
| GCAAGCTGTA CCATATTGCC ATGCACGGTC CCGCTAAGAA TACAGAAGAG GAGCAGTACA | 2040 |
| AGGTTACAAA GGCAGAGCTC GCAGAAACAG AGTACGTGTT TGACGTGGAC AAGAAGCGAT | 2100 |
| GCGTTAAGAA GGAAGAAGCC TCAGGACTTG TCCTTTCGGG AGAACTGACC AACCCGCCCT | 2160 |
| ATCACGAACT AGCTCTTGAG GGACTGAAGA CTCGACCCGC GGTCCCGTAC AAGGTTGAAA | 2220 |
| CAATAGGAGT GATAGGCACA CCAGGATCGG GCAAGTCAGC TATCATCAAG TCAACTGTCA | 2280 |
| CGGCACGTGA TCTTGTTACC AGCGGAAAGA AAGAAAACTG CCGCGAAATT GAGGCCGACG | 2340 |
| TGCTACGGCT GAGGGGCATG CAGATCACGT CGAAGACAGT GGATTCGGTT ATGCTCAACG | 2400 |
| GATGCCACAA AGCCGTAGAA GTGCTGTATG TTGACGAAGC GTTCCGGTGC CACGCAGGAG | 2460 |
| CACTACTTGC CTTGATTGCA ATCGTCAGAC CCCGTAAGAA GGTAGTACTA TGCGGAGACC | 2520 |

```
CTAAGCAATG CGGATTCTTC AACATGATGC AACTAAAGGT ACATTTCAAC CACCCTGAAA    2580

AAGACATATG TACCAAGACA TTCTACAAGT TTATCTCCCG ACGTTGCACA CAGCCAGTCA    2640

CGGCTATTGT ATCGACACTG CATTACGATG GAAAAATGAA AACCACAAAC CCGTGCAAGA    2700

AGAACATCGA AATCGACATT ACAGGGGCCA CGAAGCCGAA GCCAGGGGAC ATCATCCTGA    2760

CATGTTTCCG CGGGTGGGTT AAGCAACTGC AAATCGACTA TCCCGGACAT GAGGTAATGA    2820

CAGCCGCGGC CTCACAAGGG CTAACCAGAA AAGGAGTATA TGCCGTCCGG CAAAAAGTCA    2880

ATGAAAACCC GCTGTACGCG ATCACATCAG AGCATGTGAA CGTGTTGCTC ACCCGCACTG    2940

AGGACAGGCT AGTATGGAAA ACTTTACAGG GCGACCCATG GATTAAGCAG CTCACTAACG    3000

TACCTAAAGG AAATTTTCAG GCCACCATCG AGGACTGGGA AGCTGAACAC AAGGGAATAA    3060

TTGCTGCGAT AAACAGTCCC GCTCCCCGTA CCAATCCGTT CAGCTGCAAG ACTAACGTTT    3120

GCTGGGCGAA AGCACTGGAA CCGATACTGG CCACGGCCGG TATCGTACTT ACCGGTTGCC    3180

AGTGGAGCGA GCTGTTCCCA CAGTTTGCGG ATGACAAACC ACACTCGGCC ATCTACGCCT    3240

TAGACGTAAT TTGCATTAAG TTTTTCGGCA TGGACTTGAC AAGCGGGCTG TTTTCCAAAC    3300

AGAGCATCCC GTTAACGTAC CATCCTGCCG ACTCAGCGAG GCCAGTAGCT CATTGGGACA    3360

ACAGCCCAGG AACACGCAAG TATGGGTACG ATCACGCCGT TGCCGCCGAA CTCTCCCGTA    3420

GATTTCCGGT GTTCCAGCTA GCTGGGAAAG GCACACAGCT TGATTTGCAG ACGGGCAGAA    3480

CTAGAGTTAT CTCTGCACAG CATAACTTGG TCCCAGTGAA CCGCAATCTC CCTCACGCCT    3540

TAGTCCCCGA GCACAAGGAG AAACAACCCG GCCCGGTCGA AAAATTCTTG AGCCAGTTCA    3600

AACACCACTC CGTACTTGTG ATCTCAGAGA AAAAAATTGA AGCTCCCCAC AAGAGAATCG    3660

AATGGATCGC CCCGATTGGC ATAGCCGGCG CAGATAAGAA CTACAACCTG GCTTTCGGGT    3720

TTCCGCCGCA GGCACGGTAC GACCTGGTGT TCATCAATAT TGGAACTAAA TACAGAAACC    3780

ATCACTTTCA ACAGTGCGAA GACCACGCGG CGACCTTGAA AACCCTTTCG CGTTCGGCCC    3840

TGAACTGCCT TAACCCCGGA GGGACCCTCG TGGTGAAGTC CTACGGTTAC GCCGACCGCA    3900

ATAGTGAGGA CGTAGTCACC GCTCTTGCCA GAAAATTTGT CAGAGTGTCT GCAGCGAGGC    3960

CAGAGTGCGT CTCAAGCAAT ACAGAAATGT ACCTGATTTT CCGACAACTA GACAACAGCC    4020

GCACACGACA ATTCACCCCG CATCATTTGA ATTGTGTGAT TTCGTCCGTG TACGAGGGTA    4080

CAAGAGACGG AGTTGGAGCC GCACCGTCGT ACCGTACTAA AAGGGAGAAC ATTGCTGATT    4140

GTCAAGAGGA AGCAGTTGTC AATGCAGCCA ATCCACTGGG CAGACCAGGA GAAGGAGTCT    4200

GCCGTGCCAT CTATAAACGT TGGCCGAACA GTTTCACCGA TTCAGCCACA GAGACAGGTA    4260

CCGCAAAACT GACTGTGTGC AAGGAAAGA AAGTGATCCA CGCGGTTGGC CCTGATTTCC    4320

GGAAACACCC AGAGGCAGAA GCCCTGAAAT TGCTGCAAAA CGCCTACCAT GCAGTGGCAG    4380

ACTTAGTAAA TGAACATAAT ATCAAGTCTG TCGCCATCCC ACTGCTATCT ACAGGCATTT    4440

ACGCAGCCGG AAAAGACCGC CTTGAGGTAT CACTTAACTG CTTGACAACC GCGCTAGACA    4500

GAACTGATGC GGACGTAACC ATCTACTGCC TGGATAAGAA GTGGAAGGAA AGAATCGACG    4560

CGGTGCTCCA ACTTAAGGAG TCTGTAACTG AGCTGAAGGA TGAGGATATG GAGATCGACG    4620

ACGAGTTAGT ATGGATCCAT CCGGACAGTT GCCTGAAGGG AAGAAAGGGA TTCAGTACTA    4680

CAAAAGGAAA GTTGTATTCG TACTTTGAAG GCACCAAATT CCATCAAGCA GCAAAAGATA    4740

TGGCGGAGAT AAAGGTCCTG TTCCCAAATG ACCAGGAAAG CAACGAACAA CTGTGTGCCT    4800

ACATATTGGG GGAGACCATG GAAGCAATCC GCGAAAAATG CCCGGTCGAC CACAACCCGT    4860
```

-continued

```
CGTCTAGCCC GCCAAAAACG CTGCCGTGCC TCTGTATGTA TGCCATGACG CCAGAAAGGG    4920

TCCACAGACT CAGAAGCAAT AACGTCAAAG AAGTTACAGT ATGCTCCTCC ACCCCCCTTC    4980

CAAAGTACAA AATCAAGAAT GTTCAGAAGG TTCAGTGCAC AAAAGTAGTC CTGTTTAACC    5040

CGCATACCCC CGCATTCGTT CCCGCCCGTA AGTACATAGA AGCACCAGAA CAGCCTGCAG    5100

CTCCGCCTGC ACAGGCCGAG GAGGCCCCCG GAGTTGTAGC GACACCAACA CCACCTGCAG    5160

CTGATAACAC CTCGCTTGAT GTCACGGACA TCTCACTGGA CATGGAAGAC AGTAGCGAAG    5220

GCTCACTCTT TTCGAGCTTT AGCGGATCGG ACAACTACCG AAGGCAGGTG GTGGTGGCTG    5280

ACGTCCATGC CGTCCAAGAG CCTGCCCCTG TTCCACCGCC AAGGCTAAAG AAGATGGCCC    5340

GCCTGGCAGC GGCAAGAATG CAGGAAGAGC CAACTCCACC GGCAAGCACC AGCTCTGCGG    5400

ACGAGTCCCT TCACCTTTCT TTTGATGGGG TATCTATATC CTTCGGATCC CTTTTCGACG    5460

GAGAGATGGC CCGCTTGGCA GCGGCACAAC CCCCGGCAAG TACATGCCCT ACGGATGTGC    5520

CTATGTCTTT CGGATCGTTT TCCGACGGAG AGATTGAGGA GTTGAGCCGC AGAGTAACCG    5580

AGTCGGAGCC CGTCCTGTTT GGGTCATTTG AACCGGGCGA AGTGAACTCA ATTATATCGT    5640

CCCGATCAGC CGTATCTTTT CCACCACGCA AGCAGAGACG TAGACGCAGG AGCAGGAGGA    5700

CCGAATACTG TCTAACCGGG GTAGGTGGGT ACATATTTTC GACGGACACA GGCCCTGGGC    5760

ACTTGCAAAA GAAGTCCGTT CTGCAGAACC AGCTTACAGA ACCGACCTTG GAGCGCAATG    5820

TTCTGGAAAG AATCTACGCC CCGGTGCTCG CACACGTCGAA AGAGGAACAG CTCAAACTCA    5880

GGTACCAGAT GATGCCCACC GAAGCCAACA AAAGCAGGTA CCAGTCTCGA AAAGTAGAAA    5940

ACCAGAAAGC CATAACCACT GAGCGACTGC TTTCAGGGCT ACGGCTGTAT AACTCTGCCA    6000

CAGATCAGCC AGAATGCTAT AAGATCACCT ACCCGAAACC ATCGTATTCC AGCAGTGTAC    6060

CAGCGAACTA CTCTGACCCA AGTTTGCTG TAGCTGTTTG TAACAACTAT CTGCATGAGA    6120

ATTACCCGAC GGTAGCATCT TATCAGATCA CCGACGAGTA CGATGCTTAC TTGGATATGG    6180

TAGACGGGAC AGTCGCTTGC CTAGATACTG CAACTTTTTG CCCCGCCAAG CTTAGAAGTT    6240

ACCCGAAAAG ACACGAGTAT AGAGCCCCAA ACATCCGCAG TGCGGTTCCA TCAGCGATGC    6300

AGAACACGTT GCAAAACGTG CTCATTGCCG CGACTAAAAG AAACTGCAAC GTCACACAAA    6360

TGCGTGAACT GCCAACACTG GACTCAGCGA CATTCAACGT TGAATGCTTT CGAAAATATG    6420

CATGCAATGA CGAGTATTGG GAGGAGTTTG CCCGAAAGCC AATTAGGATC ACTACTGAGT    6480

TCGTTACCGC ATACGTGGCC AGACTGAAAG GCCCTAAGGC CGCCGCACTG TTCGCAAAGA    6540

CGCATAATTT GGTCCCATTG CAAGAAGTGC CTATGGATAG ATTCGTCATG GACATGAAAA    6600

GAGACGTGAA AGTTACACCT GGCACGAAAC ACACAGAAGA AAGACCGAAA GTACAAGTGA    6660

TACAAGCCGC AGAACCCCTG GCGACCGCTT ACCTATGCGG GATCCACCGG GAGTTAGTGC    6720

GCAGGCTTAC AGCCGTTTTG CTACCCAACA TTCACACGCT CTTTGACATG TCGGCGGAGG    6780

ACTTTGATGC AATCATAGCA GAACACTTCA AGCAAGGTGA CCCGGTACTG GAGACGGATA    6840

TCGCCTCGTT CGACAAAAGC CAAGACGACG CTATGGCGTT AACCGGCCTG ATGATCTTGG    6900

AAGACCTGGG TGTGGACCAA CCACTACTCG ACTTGATCGA GTGCGCCTTT GGAGAAATAT    6960

CATCCACCCA TCTGCCCACG GGTACCCGTT TCAAATTCGG GGCGATGATG AAATCCGGAA    7020

TGTTCCTCAC GCTCTTTGTC AACACAGTTC TGAATGTCGT TATCGCCAGC AGAGTATTGG    7080

AGGAGCGGCT TAAAACGTCC AAATGTGCAG CATTTATCGG CGACGACAAC ATTATACACG    7140

GAGTAGTATC TGACAAAGAA ATGGCTGAGA GGTGTGCCAC CTGGCTCAAC ATGGAGGTTA    7200

AGATCATTGA CGCAGTCATC GGCGAGAGAC CACCTTACTT CTGCGGTGGA TTCATCTTGC    7260
```

```
AAGATTCGGT TACCTCCACA GCGTGTCGCG TGGCGGACCC CTTGAAAAGG CTGTTTAAGT    7320

TGGGTAAACC GCTCCCAGCC GACGATGAGC AAGACGAAGA CAGAAGACGC GCTCTGCTAG    7380

ATGAAACAAA GGCGTGGTTT AGAGTAGGTA TAACAGACAC CTTAGCAGTG GCCGTGGCAA    7440

CTCGGTATGA GGTAGACAAC ATCACACCTG TCCTGCTGGC ATTGAGAACT TTTGCCCAGA    7500

GCAAAAGAGC ATTTCAAGCC ATCAGAGGGG AAATAAAGCA TCTCTACGGT GGTCCTAAAT    7560

AGTCAGCATA GTACATTTCA TCTGACTAAT ACCACAACAC CACCACCATG AATAGAGGAT    7620

TCTTTAACAT GCTCGGCCGC CGCCCCTTCC CAGCCCCCAC TGCCATGTGG AGGCCGCGGA    7680

GAAGGAGGCA GGCGGCCCCG ATGCCTGCCC GCAATGGGCT GGCTTCCCAA ATCCAGCAAC    7740

TGACCACAGC CGTCAGTGCC CTAGTCATTG GACAGGCAAC TAGACCTCAA ACCCCACGCC    7800

CACGCCCGCC GCCGCGCCAG AAGAAGCAGG CGCCAAAGCA ACCACCGAAG CCGAAGAAAC    7860

CAAAACACA GGAGAAGAAG AAGAAGCAAC CTGCAAAACC CAAACCCGGA AAGAGACAGC    7920

GTATGGCACT TAAGTTGGAG GCCGACAGAC TGTTCGACGT CAAAAATGAG GACGGAGATG    7980

TCATCGGGCA CGCACTGGCC ATGGAAGGAA AGGTAATGAA ACCACTCCAC GTGAAAGGAA    8040

CTATTGACCA CCCTGTGCTA TCAAAGCTCA AATTCACCAA GTCGTCAGCA TACGACATGG    8100

AGTTCGCACA GTTGCCGGTC AACATGAGAA GTGAGGCGTT CACCTACACC AGTGAACACC    8160

CTGAAGGGTT CTACAACTGG CACCACGGAG CGGTGCAGTA TAGTGGAGGC AGATTTACCA    8220

TCCCCCGCGG AGTAGGAGGC AGAGGAGACA GTGGTCGTCC GATTATGGAT AACTCAGGCC    8280

GGGTTGTCGC GATAGTCCTC GGAGGGGCTG ATGAGGGAAC AAGAACCGCC CTTTCGGTCG    8340

TCACCTGGAA TAGCAAAGGG AAGACAATCA AGACAACCCC GGAAGGGACA GAAGAGTGGT    8400

CTGCTGCACC ACTGGTCACG GCCATGTGCT TGCTTGGAAA CGTGAGCTTC CCATGCAATC    8460

GCCCGCCCAC ATGCTACACC CGCGAACCAT CCAGAGCTCT CGACATCCTC GAAGAGAACG    8520

TGAACCACGA GGCCTACGAC ACCCTGCTCA ACGCCATATT GCGGTGCGGA TCGTCCGGCA    8580

GAAGTAAAAG AAGCGTCACT GACGACTTTA CCTTGACCAG CCCGTACTTG GGCACATGCT    8640

CGTACTGTCA CCATACTGAA CCGTGCTTTA GCCCGATTAA GATCGAGCAG GTCTGGGATG    8700

AAGCGGACGA CAACACCATA CGCATACAGA CTTCCGCCCA GTTTGGATAC GACCAAAGCG    8760

GAGCAGCAAG CTCAAATAAG TACCGCTACA TGTCGCTCGA GCAGGATCAT ACTGTCAAAG    8820

AAGGCACCAT GGATGACATC AAGATCAGCA CCCTCAGGAC CGTGTAGAAGG CTTAGCTACA    8880

AAGGATACTT TCTCCTCGCG AAGTGTCCTC CAGGGGACAG CGTAACGGTT AGCATAGCGA    8940

GTAGCAACTC AGCAACGTCA TGCACAATGG CCCGCAAGAT AAAACCAAAA TTCGTGGGAC    9000

GGGAAAAATA TGACCTACCT CCCGTTCACG GTAAGAAGAT TCCTTGCACA GTGTACGACC    9060

GTCTGAAAGA AACAACCGCC GGCTACATCA CTATGCACAG GCCGGGACCG ACGCCTATA    9120

CATCCTATCT GGAGGAATCA TCAGGGAAAG TTTACGCGAA GCCACCATCC GGGAAGAACA    9180

TTACGTACGA GTGCAAGTGC GGCGATTACA AGACCGGAAC CGTTACGACC CGTACCGAAA    9240

TCACGGGCTG CACCGCCATC AAGCAGTGCG TCGCCTATAA GAGCGACCAA ACGAAGTGGG    9300

TCTTCAACTC GCCGGACTCG ATCAGACACG CCGACCACAC GGCCCAAGGG AAATTGCATT    9360

TGCCTTTCAA GCTGATCCCG AGTACCTGCA TGGTCCCTGT TGCCCACGCG CCGAACGTAG    9420

TACACGGCTT TAAACACATC AGCCTCCAAT TAGACACAGA CCATCTGACA TTGCTCACCA    9480

CCAGGAGACT AGGGGCAAAC CCGGAACCAA CCACTGAATG GATCATCGGA AACACGGTTA    9540

GAAACTTCAC CGTCGACCGA GATGGCCTGG AATACATATG GGGCAATCAC GAACCAGTAA    9600
```

```
GGGTCTATGC CCAAGAGTCT GCACCAGGAG ACCCTCACGG ATGGCACAC GAAATAGTAC      9660

AGCATTACTA TCATCGCCAT CCTGTGTACA CCATCTTAGC CGTCGCATCA GCTGCTGTGG     9720

CGATGATGAT TGGCGTAACT GTTGCAGCAT TATGTGCCTG TAAAGCGCGC CGTGAGTGCC     9780

TGACGCCATA TGCCCTGGCC CCAAATGCCG TGATTCCAAC TTCGCTGGCA CTTTTGTGCT     9840

GTGTTAGGTC GGCTAATGCT GAAACATTCA CCGAGACCAT GAGTTACTTA TGGTCGAACA     9900

GCCAGCCGTT CTTCTGGGTC CAGCTGTGTA TACCTCTGGC CGCTGTCGTC GTTCTAATGC     9960

GCTGTTGCTC ATGCTGCCTG CCTTTTTTAG TGGTTGCCGG CGCCTACCTG GCGAAGGTAG    10020

ACGCCTACGA ACATGCGACC ACTGTTCCAA ATGTGCCACA GATACCGTAT AAGGCACTTG    10080

TTGAAAGGGC AGGGTACGCC CCGCTCAATT TGGAGATTAC TGTCATGTCC TCGGAGGTTT    10140

TGCCTTCCAC CAACCAAGAG TACATTACCT GCAAATTCAC CACTGTGGTC CCCTCCCCTA    10200

AAGTCAGATG CTGCGGCTCC TTGGAATGTC AGCCCGCCGC TCACGCAGAC TATACCTGCA    10260

AGGTCTTTGG AGGGGTGTAC CCCTTCATGT GGGGAGGAGC ACAATGTTTT TGCGACAGTG    10320

AGAACAGCCA GATGAGTGAG GCGTACGTCG AATTGTCAGT AGATTGCGCG ACTGACCACG    10380

CGCAGGCGAT TAAGGTGCAT ACTGCCGCGA TGAAAGTAGG ACTGCGTATA GTGTACGGGA    10440

ACACTACCAG TTTCCTAGAT GTGTACGTGA ACGGAGTCAC ACCAGGAACG TCTAAAGACC    10500

TGAAAGTCAT AGCTGGACCA ATTTCAGCAT TGTTTACACC ATTCGATCAC AAGGTCGTTA    10560

TCAATCGCGG CCTGGTGTAC AACTATGACT TTCCGGAATA CGGAGCGATG AAACCAGGAG    10620

CGTTTGGAGA CATTCAAGCT ACCTCCTTGA CTAGCAAAGA CCTCATCGCC AGCACAGACA    10680

TTAGGCTACT CAAGCCTTCC GCCAAGAACG TGCATGTCCC GTACACGCAG GCCGCATCTG    10740

GATTCGAGAT GTGGAAAAAC AACTCAGGCC GCCCACTGCA GGAAACCGCC CCTTTTGGGT    10800

GCAAGATTGC AGTCAATCCG CTTCGAGCGG TGGACTGCTC ATACGGGAAC ATTCCCATTT    10860

CTATTGACAT CCCGAACGCT GCCTTTATCA GGACATCAGA TGCACCACTG GTCTCAACAG    10920

TCAAATGTGA TGTCAGTGAG TGCACTTATT CAGCGGACTT CGGAGGGATG GCTACCCTGC    10980

AGTATGTATC CGACCGCGAA GGACAATGCC CTGTACATTC GCATTCGAGC ACAGCAACCC    11040

TCCAAGAGTC GACAGTTCAT GTCCTGGAGA AAGGAGCGGT GACAGTACAC TTCAGCACCG    11100

CGAGCCCACA GGCGAACTTC ATTGTATCGC TGTGTGGTAA GAAGACAACA TGCAATGCAG    11160

AATGCAAACC ACCAGCTGAT CATATCGTGA GCACCCCGCA CAAAAATGAC CAAGAATTCC    11220

AAGCCGCCAT CTCAAAAACT TCATGGAGTT GGCTGTTTGC CCTTTTCGGC GGCGCCTCGT    11280

CGCTATTAAT TATAGGACTT ATGATTTTTG CTTGCAGCAT GATGCTGACT AGCACACGAA    11340

GATGACCGCT ACGCCCCAAT GACCCGACCA GCAAAACTCG ATGTACTTCC GAGGAACTGA    11400

TGTGCATAAT GCATCAGGCT GGTATATTAG ATCCCCGCTT ACCGCGGGCA ATATAGCAAC    11460

ACCAAAACTC GACGTATTTC CGAGGAAGCG CAGTGCATAA TGCTGCGCAG TGTTGCCAAA    11520

TAATCACTAT ATTAACCATT TATTCAGCGG ACGCCAAAAC TCAATGTATT CTGAGGAAG    11580

CATGGTGCAT AATGCCATGC AGCGTCTGCA TAACTTTTTA TTATTTCTTT TATTAATCAA    11640

CAAAATTTTG TTTTTAACAT TTC                                           11663
```

(2) INFORMATION FOR SEQ ID NO:8:

(i) SEQUENCE CHARACTERISTICS:
        (A) LENGTH: 11703 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
ATTGGCGGCG TAGTACACAC TATTGAATCA AACAGCCGAC CAATTGCACT ACCATCACA          59
ATG GAG AAG CCA GTA GTA AAC GTA GAC GTA GAC CCC CAG AGT CCG TTT         107
GTC GTG CAA CTG CAA AAA AGC TTC CCG CAA TTT GAG GTA GTA GCA CAG         155
CAG GTC ACT CCA AAT GAC CAT GCT AAT GCC AGA GCA TTT TCG CAT CTG         203
GCC AGT AAA CTA ATC GAG CTG GAG GTT CCT ACC ACA GCG ACG ATC TTG         251
GAC ATA GGC AGC GCA CCG GCT CGT AGA ATG TTT TCC GAG CAC CAG TAT         299
CAT TGT GTC TGC CCC ATG CGT AGT CCA GAA GAC CCG GAC CGC ATG ATG         347
AAA TAT GCC AGT AAA CTG GCG GAA AAA GCG TGC AAG ATT ACA AAC AAG         395
AAC TTG CAT GAG AAG ATT AAG GAT CTC CGG ACC GTA CTT GAT ACG CCG         443
GAT GCT GAA ACA CCA TCG CTC TGC TTT CAC AAC GAT GTT ACC TGC AAC         491
ATG CGT GCC GAA TAT TCC GTC ATG CAG GAC GTG TAT ATC AAC GCT CCC         539
GGA ACT ATC TAT CAT CAG GCT ATG AAA GGC GTG CGG ACC CTG TAC TGG         587
ATT GGC TTC GAC ACC ACC CAG TTC ATG TTC TCG GCT ATG GCA GGT TCG         635
TAC CCT GCG TAC AAC ACC AAC TGG GCC GAC GAG AAA GTC CTT GAA GCG         683
CGT AAC ATC GGA CTT TGC AGC ACA AAG CTG AGT GAA GGT AGG ACA GGA         731
AAA TTG TCG ATA ATG AGG AAG AAG GAG TTG AAG CCC GGG TCG CGG GTT         779
TAT TTC TCC GTA GGA TCG ACA CTT TAT CCA GAA CAC AGA GCC AGC TTG         827
CAG AGC TGG CAT CTT CCA TCG GTG TTC CAC TTG AAT GGA AAG CAG TCG         875
TAC ACT TGC CGC TGT GAT ACA GTG GTG AGT TGC GAA GGC TAC GTA GTG         923
AAG AAA ATC ACC ATC AGT CCC GGG ATC ACG GGA GAA ACC GTG GGA TAC         971
GCG GTT ACA CAC AAT AGC GAG GGC TTC TTG CTA TGC AAA GTT ACT GAC        1019
ACA GTA AAA GGA GAA CGG GTA TCG TTC CCT GTG TGC ACG TAC ATC CCG        1067
GCC ACC ATA TGC GAT CAG ATG ACT GGT ATA ATG GCC ACG GAT ATA TCA        1115
CCT GAC GAT GCA CAA AAA CTT CTG GTT GGG CTC AAC CAG CGA ATT GTC        1163
ATT AAC GGT AGG ACT AAC AGG AAC ACC AAC ACC ATG CAA AAT TAC CTT        1211
CTG CCG ATC ATA GCA CAA GGG TTC AGC AAA TGG GCT AAG GAG CGC AAG        1259
GAT GAT CTT GAT AAC GAG AAA ATG CTG GGT ACT AGA GAA CGC AAG CTT        1307
ACG TAT GGC TGC TTG TGG GCG TTT CGC ACT AAG AAA GTA CAT TCG TTT        1355
TAT CGC CCA CCT GGA ACG CAG ACC ATC GTA AAA GTC CCA GCC TCT TTT        1403
AGC GCT TTT CCC ATG TCG TCC GTA TGG ACG ACC TCT TTG CCC ATG TCG        1451
CTG AGG CAG AAA TTG AAA CTG GCA TTG CAA CCA AAG AAG GAG GAA AAA        1499
CTG CTG CAG GTC TCG GAG GAA TTA GTC ATG GAG GCC AAG GCT GCT TTT        1547
GAG GAT GCT CAG GAG GAA GCC AGA GCG GAG AAG CTC CGA GAA GCA CTT        1595
CCA CCA TTA GTG GCA GAC AAA GGC ATC GAG GCA GCC GCA GAA GTT GTC        1643
TGC GAA GTG GAG GGG CTC CAG GCG GAC ATC GGA GCA GCA TTA GTT GAA        1691
ACC CCG CGC GGT CAC GTA AGG ATA ATA CCT CAA GCA AAT GAC CGT ATG        1739
ATC GGA CAG TAT ATC GTT GTC TCG CCA AAC TCT GTG CTG AAG AAT GCC        1787
AAA CTC GCA CCA GCG CAC CCG CTA GCA GAT CAG GTT AAG ATC ATA ACA        1835
```

```
CAC TCC GGT AGA TCA GGA AGG TAC GCG GTC GAA CCA TAC GAC GCT AAA      1883

GTA CTG ATG CCA GCA GGA GGT GCC GTA CCA TGG CCA GAA TTC CTA GCA      1931

CTG AGT GAG AGC GCC ACG TTA GTG TAC AAC GAA AGA GAG TTT GTG AAC      1979

CGC AAA CTA TAC CAC ATT GCC ATG CAT GGC CCC GCC AAG AAT ACA GAA      2027

GAG GAG CAG TAC AAG GTT ACA AAG GCA GAG CTT GCA GAA ACA GAG TAC      2075

GTG TTT GAC GTG GAC AAG AAG CGT TGC GTT AAG AAG GAA GAA GCC TCA      2123

GGT CTG GTC CTC TCG GGA GAA CTG ACC AAC CCT CCC TAT CAT GAG CTA      2171

GCT CTG GAG GGA CTG AAG ACC CGA CCT GCG GTC CGT TAC AAG GTC GAA      2219

ACA ATA GGA GTG ATA GGC ACA CCG GGG TCG GGC AAG TCA GCT ATT ATC      2267

AAG TCA ACT GTC ACG GCA CGG GAT CTT GTT ACC AGC GGA AAG AAA GAA      2315

AAT TGT CGC GAA ATT GAG GCC GAC GTG CTA AGA CTG AGG GGT ATG CAG      2363

ATT ACG TCG AAG ACA GTA GAT TCG GTT ATG CTC AAC GGA TGC CAC AAA      2411

GCC GTA GAA GTG CTG TAC GTT GAC GAA GCG TTC GCG TGC CAC GCA GGA      2459

GCA CTA CTT GCC TTG ATT GCT ATC GTC AGG CCC CGC AAG AAG GTA GTA      2507

CTA TGC GGA GAC CCC ATG CAA TGC GGA TTC TTC AAC ATG ATG CAA CTA      2555

AAG GTA CAT TTC AAT CAC CCT GAA AAA GAC ATA TGC ACC AAG ACA TTC      2603

TAC AAG TAT ATC TCC CGG CGT TGC ACA CAG CCA GTT ACA GCT ATT GTA      2651

TCG ACA CTG CAT TAC GAT GGA AAG ATG AAA ACC ACG AAC CCG TGC AAG      2699

AAG AAC ATT GAA ATC GAT ATT ACA GGG GCC ACA AAG CCG AAG CCA GGG      2747

GAT ATC ATC CTG ACA TGT TTC CGC GGG TGG GTT AAG CAA TTG CAA ATC      2795

GAC TAT CCC GGA CAT GAA GTA ATG ACA GCC GCG GCC TCA CAA GGG CTA      2843

ACC AGA AAA GGA GTG TAT GCC GTC CGG CAA AAA GTC AAT GAA AAC CCA      2891

CTG TAC GCG ATC ACA TCA GAG CAT GTG AAC GTG TTG CTC ACC CGC ACT      2939

GAG GAC AGG CTA GTG TGG AAA ACC TTG CAG GGC GAC CCA TGG ATT AAG      2987

CAG CTC ACT AAC ATA CCT AAA GGA AAC TTT CAG GCT ACT ATA GAG GAC      3035

TGG GAA GCT GAA CAC AAG GGA ATA ATT GCT GCA ATA AAC AGC CCC ACT      3083

CCC CGT GCC AAT CCG TTC AGC TGC AAG ACC AAC GTT TGC TGG GCG AAA      3131

GCA TTG GAA CCA ATA CTA GCC ACG GCC GGT ATC GTA CTT ACC GGT TGC      3179

CAG TGG AGC GAA CTG TTC CCA CAG TTT GCG GAT GAC AAA CCA CAT TCG      3227

GCC ATT TAC GCC TTA GAC GTA ATT TGC ATT AAG TTT TTC GGC ATG GAC      3275

TTG ACA AGC GGA CTG TTT TCT AAA CAG AGC ATC CCA CTA ACG TAC CAT      3323

CCC GCC GAT TCA GCG AGG CCG GTA GCT CAT TGG GAC AAC AGC CCA GGA      3371

ACC CGC AAG TAT GGG TAC GAT CAC GCC ATT GCC GCC GAA CTC TCC CGT      3419

AGA TTT CCG GTG TTC AGG CTA GCT GGG AAG GGC ACA CAA CTT GAT TTG      3467

CAG ACG GGG AGA ACC AGA GTT ATC TCT GCA CAG CAT AAC CTG GTC CCG      3515

GTG AAC CGC AAT CTT CCT CAC GCC TTA GTC CCC GAG TAC AAG GAG AAG      3563

CAA CCC GGC CCG GTC GAA AAA TTC TTG AAC CAG TTC AAA CAC CAC TCA      3611

GTA CTT GTG GTA TCA GAG GAA AAA ATT GAA GCT CCC CGT AAG AGA ATC      3659

GAA TGG ATC GCC CCG ATT GGC ATA GCC GGT GCA GAT AAG AAC TAC AAC      3707
```

```
CTG GCT TTC GGG TTT CCG CCG CAG GCA CGG TAC GAC CTG GTG TTC ATC      3755
AAC ATT GGA ACT AAA TAC AGA AAC CAC CAC TTT CAG CAG TGC GAA GAC      3803
CAT GCG GCG ACC TTA AAA ACC CTT TCG CGT TCG GCC CTG AAT TGC CTT      3851
AAC CCA GGA GGC ACC CTC GTG GTG AAG TCC TAT GGC TAC GCC GAC CGC      3899
AAC AGT GAG GAC GTA GTC ACC GCT CTT GCC AGA AAG TTT GTC AGG GTG      3947
TCC GCA GCG AGA CCA GAT TGT GTC TCA AGC AAT ACA GAA ATG TAC CTG      3995
ATT TTC CGA CAA CTA GAC AAC AGC CGT ACA CGG CAA TTC ACC CCG CAC      4043
CAT CTG AAT TGC GTG ATT TCG TCC GTG TAT GAG GGT ACA AGA GAT GGA      4091
GTT GGA GCC GCG CCG TCA TAC CGC ACC AAA AGG GAG AAT ATT GCT GAC      4139
TGT CAA GAG GAA GCA GTT GTC AAC GCA GCC AAT CCG CTG GGT AGA CCA      4187
GGC GAA GGA GTC TGC CGT GCC ATC TAT AAA CGT TGG CCG ACC AGT TTT      4235
ACC GAT TCA GCC ACG GAG ACA GGC ACC GCA AGA ATG ACT GTG TGC CTA      4283
GGA AAG AAA GTG ATC CAC GCG GTC GGC CCT GAT TTC CGG AAG CAC CCA      4331
GAA GCA GAA GCC TTG AAA TTG CTA CAA AAC GCC TAC CAT GCA GTG GCA      4379
GAC TTA GTA AAT GAA CAT AAC ATC AAG TCT GTC GCC ATT CCA CTG CTA      4427
TCT ACA GGC ATT TAC GCA GCC GGA AAA GAC CGC CTT GAA GTA TCA CTT      4475
AAC TGC TTG ACA ACC GCG CTA GAC AGA ACT GAC GCG GAC GTA ACC ATC      4523
TAT TGC CTG GAT AAG AAG TGG AAG GAA AGA ATC GAC GCG GCA CTC CAA      4571
CTT AAG GAG TCT GTA ACA GAG CTG AAG GAT GAA GAT ATG GAG ATC GAC      4619
GAT GAG TTA GTA TGG ATC CAT CCA GAC AGT TGC TTG AAG GGA AGA AAG      4667
GGA TTC AGT ACT ACA AAA GGA AAA TTG TAT TCG TAC TTC GAA GGC ACC      4715
AAA TTC CAT CAA GCA GCA AAA GAC ATG GCG GAG ATA AAG GTC CTG TTC      4763
CCT AAT GAC CAG GAA AGT AAT GAA CAA CTG TGT GCC TAC ATA TTG GGT      4811
GAG ACC ATG GAA GCA ATC CGC GAA AAG TGC CCG GTC GAC CAT AAC CCG      4859
TCG TCT AGC CCG CCC AAA ACG TTG CCG TGC CTT TGC ATG TAT GCC ATG      4907
ACG CCA GAA AGG GTC CAC AGA CTT AGA AGC AAT AAC GTC AAA GAA GTT      4955
ACA GTA TGC TCC TCC ACC CCC CTT CCT AAG CAC AAA ATT AAG AAT GTT      5003
CAG AAG GTT CAG TGC ACG AAA GTA GTC CTG TTT AAT CCG CAC ACT CCC      5051
GCA TTC GTT CCC GCC CGT AAG TAC ATA GAA GTG CCA GAA CAG CCT ACC      5099
GCT CCT CCT GCA CAG GCC GAG GAG GCC CCC GAA GTT GTA GCG ACA CCG      5147
TCA CCA TCT ACA GCT GAT AAC ACC TCG CTT GAT GTC ACA GAC ATC TCA      5195
CTG GAT ATG GAT GAC AGT AGC GAA GGC TCA CTT TTT TCG AGC TTT AGC      5243
GGA TCG GAC AAC TCT ATT ACT AGT ATG GAC AGT TGG TCG TCA GGA CCT      5291
AGT TCA CTA GAG ATA GTA GAC CGA AGG CAG GTG GTG GTG GCT GAC GTT      5339
CAT GCC GTC CAA GAG CCT GCC CCT ATT CCA CCG CCA AGG CTA AAG AAG      5387
ATG GCC CGC CTG GCA GCG GCA AGA AAA GAG CCC ACT CCA CCG GCA AGC      5435
AAT AGC TCT GAG TCC CTC CAC CTC TCT TTT GGT GGG GTA TCC ATG TCC      5483
CTC GGA TCA ATT TTC GAC GGA GAG ACG GCC CGC CAG GCA GCG TAC AA      5531
CCC CTG GCA ACA GGC CCC ACG GAT GTG CCT ATG TCT TTC GGA TCG TTT      5579
TCC GAC GGA GAG ATT GAT GAG CTG AGC CGC AGA GTA ACT GAG TCC GAA      5627
```

```
CCC GTC CTG TTT GGA TCA TTT GAA CCG GGC GAA GTG AAC TCA ATT ATA      5675
TCG TCC CGA TCA GCC GTA TCT TTT CCA CTA CGC AAG CAG AGA CGT AGA      5723
CGC AGG AGC AGG AGG ACT GAA TAC TGA CTA ACC GGG GTA GGT GGG TAC      5771
ATA TTT TCG ACG GAC ACA GGC CCT GGG CAC TTG CAA AAG AAG TCC GTT      5819
CTG CAG AAC CAG CTT ACA GAA CCG ACC TTG GAG CGC AAT GTC CTG GAA      5867
AGA ATT CAT GCC CCG GTG CTC GAC ACG TCG AAA GAG GAA CAA CTC AAA      5915
CTC AGG TAC CAG ATG ATG CCC ACC GAA GCC AAC AAA AGT AGG TAC CAG      5963
TCT CGT AAA GTA GAA AAT CAG AAA GCC ATA ACC ACT GAG CGA CTA CTG      6011
TCA GGA CTA CGA CTG TAT AAC TCT GCC ACA GAT CAG CCA GAA TGC TAT      6059
AAG ATC ACC TAT CCG AAA CCA TTG TAC TCC AGT AGC GTA CCG GCG AAC      6107
TAC TCC GAT CCA CAG TTC GCT GTA GCT GTC TGT AAC AAC TAT CTG CAT      6155
GAG AAC TAT CCG ACA GTA GCA TCT TAT CAG ATT ACT GAC GAG TAC GAT      6203
GCT TAC TTG GAT ATG GTA GAC GGG ACA GTC GCC TGC CTG GAT ACT GCA      6251
ACC TTC TGC CCC GCT AAG CTT AGA AGT TAC CCG AAA AAA CAT GAG TAT      6299
AGA GCC CCG AAT ATC CGC AGT GCG GTT CCA TCA GCG ATG CAG AAC ACG      6347
CTA CAA AAT GTG CTC ATT GCC GCA ACT AAA AGA AAT TGC AAC GTC ACG      6395
CAG ATG CGT GAA CTG CCA ACA CTG GAC TCA GCG ACA TTC AAT GTC GAA      6443
TGC TTT CGA AAA TAT GCA TGT AAT GAC GAG TAT TGG GAG GAG TTC GCT      6491
CGG AAG CCA ATT AGG ATT ACC ACT GAG TTT GTC ACC GCA TAT GTA GCT      6539
AGA CTG AAA GGC CCT AAG GCC GCC GCA CTA TTT GCA AAG ACG TAT AAT      6587
TTG GTC CCA TTG CAA GAA GTG CCT ATG GAT AGA TTC GTC ATG GAC ATG      6635
AAA AGA GAC GTG AAA GTT ACA CCA GGC ACG AAA CAC ACA GAA GAA AGA      6683
CCG AAA GTA CAA GTG ATA CAA GCC GCA GAA CCC CTG GCG ACT GCT TAC      6731
TTA TGC GGG ATT CAC CGG GAA TTA GTG CGT AGG CTT ACG GCC GTC TTG      6779
CTT CCA AAC ATT CAC ACG CTT TTT GAC ATG TCG GCG GAG GAT TTT GAT      6827
GCA ATC ATA GCA GAA CAC TTC AAG CAA GGC GAC CCG GTA CTG GAG ACG      6875
GAT ATC GCA TCA TTC GAC AAA AGC CAA GAC GAC GCT ATG GCG TTA ACC      6923
GGT CTG ATG ATC TTG GAG GAC CTG GGT GTG GAT CAA CCA CTA CTC GAC      6971
TTG ATC GAG TGC GCC TTT GGA GAA ATA TCA TCC ACC CAT CTA CCT ACG      7019
GGT ACT CGT TTT AAA TTC GGG GCG ATG ATG AAA TCC GGA ATG TTC CTC      7067
ACA CTT TTT GTC AAC ACA GTT TTG AAT GTC GTT ATC GCC AGC AGA GTA      7115
CTA GAA GAG CGG CTT AAA ACG TCC AGA TGT GCA GCG TTC ATT GGC GAC      7163
GAC AAC ATC ATA CAT GGA GTA GTA TCT GAC AAA GAA ATG GCT GAG AGG      7211
TGC GCC ACC TGG CTC AAC ATG GAG GTT AAG ATC ATC GAC GCA GTC ATC      7259
GGT GAG AGA CCA CCT TAC TTC TGC GGC GGA TTT ATC TTG CAA GAT TCG      7307
GTT ACT TCC ACA GCG TGC CGC GTG GCG GAC CCC CTG AAA AGG CTG TTT      7355
AAG TTG GGT AAA CCG CTC CCA GCC GAC GAC GAG CAA GAC GAA GAC AGA      7403
AGA CGC GCT CTG CTA GAT GAA ACA AAG GCG TGG TTT AGA GTA GGT ATA      7451
ACA GGC ACT TTA GCA GTG GCC GTG ACG ACC CGG TAT GAG GTA GAC AAT      7499
```

```
ATT ACA CCT GTC CTA CTG GCA TTG AGA ACT TTT GCC CAG AGC AAA AGA      7547

GCA TTC CAA GCC ATC AGA GGG GAA ATA AAG CAT CTC TAC GGT GGT CCT      7595

AAA TAGTCAGCAT AGTACATTTC ATCTGACTAA TACTACAACA CCACCACC ATG AAT     7652

AGA GGA TTC TTT AAC ATG CTC GGC CGC CGC CCC TTC CCG GCC CCC ACT      7700

GCC ATG TGG AGG CCG CGG AGA AGG AGG CAG GCG GCC CCG ATG CCT GCC      7748

CGC AAC GGG CTG GCT TCT CAA ATC CAG CAA CTG ACC ACA GCC GTC AGT      7796

GCC CTA GTC ATT GGA CAG GCA ACT AGA CCT CAA CCC CCA CGT CCA CGC      7844

CCG CCA CCG CGC CAG AAG AAG CAG GCG CCC AAG CAA CCA CCG AAG CCG      7892

AAG AAA CCA AAA ACG CAG GAG AAG AAG AAG AAG CAA CCT GCA AAA CCC      7940

AAA CCC GGA AAG AGA CAG CGC ATG GCA CTT AAG TTG GAG GCC GAC AGA      7988

TTG TTC GAC GTC AAG AAC GAG GAC GGA GAT GTC ATC GGG CAC GCA CTG      8036

GCC ATG GAA GGA AAG GTA ATG AAA CCT CTG CAC GTG AAA GGA ACC ATC      8084

GAC CAC CCT GTG CTA TCA AAG CTC AAA TTT ACC AAG TCG TCA GCA TAC      8132

GAC ATG GAG TTC GCA CAG TTG CCA GTC AAC ATG AGA AGT GAG GCA TTC      8180

ACC TAC ACC AGT GAA CAC CCC GAA GGA TTC TAT AAC TGG CAC CAC GGA      8228

GCG GTG CAG TAT AGT GGA GGT AGA TTT ACC ATC CCT CGC GGA GTA GGA      8276

GGC AGA GGA GAC AGC GGT CGT CCG ATC ATG GAT AAC TCC GGT CGG GTT      8324

GTC GCG ATA GTC CTC GGT GGA GCT GAT GAA GGA ACA CGA ACT GCC CTT      8372

TCG GTC GTC ACC TGG AAT AGT AAA GGG AAG ACA ATT AAG ACG ACC CCG      8420

GAA GGG ACA GAA GAG TGG TCC GCA GCA CCA CTG GTC ACG GCA ATG TGT      8468

TTG CTC GGA AAT GTG AGC TTC CCA TGC GAC CGC CCG CCC ACA TGC TAT      8516

ACC CGC GAA CCT TCC AGA GCC CTC GAC ATC CTT GAA GAG AAC GTG AAC      8564

CAT GAG GCC TAC GAT ACC CTG CTC AAT GCC ATA TTG CGG TGC GGA TCG      8612

TCT GGC AGA AGC AAA AGA AGC GTC ACT GAC GAC TTT ACC CTG ACC AGC      8660

CCC TAC TTG GGC ACA TGC TCG TAC TGC CAC CAT ACT GAA CCG TGC TTC      8708

AGC CCT GTT AAG ATC GAG CAG GTC TGG GAC GAA GCG GAC GAT AAC ACC      8756

ATA CGC ATA CAG ACT TCC GCC CAG TTT GGA TAC GAC CAA AGC GGA GCA      8804

GCA AGC GCA AAC AAG TAC CGC TAC ATG TCG CTT GAG CAG GAT CAC ACC      8852

GTT AAA GAA GGC ACC ATG GAT GAC ATC AAG ATT AGC ACC TCA GGA CCG      8900

TGT AGA AGG CTT AGC TAC AAA GGA TAC TTT CTC CTC GCA AAA TGC CCT      8948

CCA GGG GAC AGC GTA ACG GTT AGC ATA GTG AGT AGC AAC TCA GCA ACG      8996

TCA TGT ACA CTG GCC CGC AAG ATA AAA CCA AAA TTC GTG GGA CGG GAA      9044

AAA TAT GAT CTA CCT CCC GTT CAC GGT AAA AAA ATT CCT TGC ACA GTG      9092

TAC GAC CGT CTG AAA GAA ACA ACT GCA GGC TAC ATC ACT ATG CAC AGG      9140

CCG GGA CCG CAC GCT TAT ACA TCC TAC CTG GAA GAA TCA TCA GGG AAA      9188

GTT TAC GCA AAG CCG CCA TCT GGG AAG AAC ATT ACG TAT GAG TGC AAG      9236

TGC GGC GAC TAC AAG ACC GGA ACC GTT TCG ACC CGC ACC GAA ATC ACT      9284

GGT TGC ACC GCC ATC AAG CAG TGC GTC GCC TAT AAG AGC GAC CAA ACG      9332

AAG TGG GTC TTC AAC TCA CCG GAC TTG ATC AGA CAT GAC GAC CAC ACG      9380

GCC CAA GGG AAA TTG CAT TTG CCT TTC AAG TTG ATC CCG AGT ACC TGC      9428
```

-continued

```
ATG GTC CCT GTT GCC CAC GCG CCG AAT GTA ATA CAT GGC TTT AAA CAC      9476
ATC AGC CTC CAA TTA GAT ACA GAC CAC TTG ACA TTG CTC ACC ACC AGG      9524
AGA CTA GGG GCA AAC CCG GAA CCA ACC ACT GAA TGG ATC GTC GGA AAG      9572
ACG TCA GAA AAC TTC ACC GTC GAC CGA GAT GGC CTG GAA TAC ATA TGG      9620
GGA AAT CAT GAG CCA GTG AGG GTC TAT GCC CAA GAG TCA GCA CCA GGA      9668
GAC CCT CAC GGA TGG CCA CAC GAA ATA GTA CAG CAT TAC TAC CAT CGC      9716
CAT CCT GTG TAC ACC ATC TTA GCC GTC GCA TCA GCT ACC GTG GCG ATG      9764
ATG ATT GGC GTA ACC GTT GCA GTG TTA TGT GCC TGT AAA GCG CGC CGT      9812
GAG TGC CTG ACG CCA TAC GCC CTG GCC CCA AAC GCC GTA ATC CCA ACT      9860
TCG CTG GCA CTC TTG TGC TGC GTT AGG TCG GCC AAT GCT GAA ACG TTC      9908
ACC GAG ACC ATG AGT TAC TTG TGG TCG AAC AGT CAG CCG TTC TTC TGG      9956
GTC CAG TTG TGC ATA CCT TTG GCC GCT TTC ATC GTT CTA ATG CGC TGC     10004
TGC TCC TGC TGC CTG CCT TTT TTA GTG GTT GCC GGC GCC TAC CTG GCG     10052
AAG GTA GAC GCC TAC GAA CAT GCG ACC ACT GTT CCA AAT GTG CCA CAG     10100
ATA CCG TAT AAG GCA CTT GTT GAA AGG GCA GGG TAT GCC CCG CTC AAT     10148
TTG GAG ATC ACT GTC ATG TCC TCG GAG GTT TTG CCT TCC ACC AAC CAA     10196
GAG TAC ATT ACC TGC AAA TTC ACC ACT GTG GTC CCC TCC CCA AAA ATC     10244
AAA TGC TGC GGC TCC TTG GAA TGT CAG CCG GCC GCT CAT GCA GAC TAT     10292
ACC TGC AAG GTC TTC GGA GGG GTC TAC CCC TTT ATG TGG GGA GGA GCG     10340
CAA TGT TTT TGC GAC AGT GAG AAC AGC CAG ATG AGT GAG GCG TAC GTC     10388
GAA CTG TCA GCA GAT TGC GCG TCT GAC CAC GCG CAG GCG ATT AAG GTG     10436
CAC ACT GCC GCG ATG AAA GTA GGA CTG CGT ATA GTG TAC GGG AAC ACT     10484
ACC AGT TTC CTA GAT GTG TAC GTG AAC GGA GTC ACA CCA GGA ACG TCT     10532
AAA GAC TTG AAA GTC ATA GCT GGA CCA ATT TCA GCA TCG TTT ACG CCA     10580
TTC GAT CAT AAG GTC GTT ATC CAT CGC GGC CTG GTG TAC AAC TAT GAC     10628
TTC CCG GAA TAT GGA GCG ATG AAA CCA GGA GCG TTT GGA GAC ATT CAA     10676
GCT ACC TCC TTG ACT AGC AAG GAT CTC ATC GCC AGC ACA GAC ATT AGG     10724
CTA CTC AAG CCT TCC GCC AAG AAC GTG CAT GTC CCG TAC ACG CAG GCC     10772
GCA TCA GGA TTT GAG ATG TGG AAA AAC AAC TCA GGC CGC CCA CTG CAG     10820
GAA ACC GCA CCT TTC GGG TGT AAG ATT GCA GTA AAT CCG CTC CGA GCG     10868
GTG GAC TGT TCA TAC GGG AAC ATT CCC ATT TCT ATT GAC ATC CCG AAC     10916
GCT GCC TTT ATC AGG ACA TCA GAT GCA CCA CTG GTC TCA ACA GTC AAA     10964
TGT GAA GTC AGT GAG TGC ACT TAT TCA GCA GAC TTC GGC GGG ATG GCC     11012
ACC CTG CAG TAT GTA TCC GAC CGC GAA GGT CAA TGC CCC GTA CAT TCG     11060
CAT TCG AGC ACA GCA ACT CTC CAA GAG TCG ACA GTA CAT GTC CTG GAG     11108
AAA GGA GCG GTG ACA GTA CAC TTT AGC ACC GCG AGT CCA CAG GCG AAC     11156
TTT ATC GTA TCG CTG TGT GGG AAG AAG ACA ACA TGC AAT GCA GAA TGT     11204
AAA CCA CCA GCT GAC CAT ATC GTG AGC ACC CCG CAC AAA AAT GAC CAA     11252
GAA TTT CAA GCC GCC ATC TCA AAA ACA TCA TGG AGT TGG CTG TTT GCC     11300
```

```
CTT TTC GGC GGC GCC TCG TCG CTA TTA ATT ATA GGA CTT ATG ATT TTT    11348

GCT TGC AGC ATG ATG CTG ACT AGC ACA CGA AGA TGACCGCTAC GCCCCAATGA  11401

TCCGACCAGC AAAACTCGAT GTACTTCCGA GGAACTGATG TGCATAATGC ATCAGGCTGG  11461

TACATTAGAT CCCCGCTTAC CGCGGGCAAT ATAGCAACAC TAAAAACTCG ATGTACTTCC  11521

GAGGAAGCGC AGTGCATAAT GCTGCGCAGT GTTGCCACAT AACCACTATA TTAACCATTT  11581

ATCTAGCGGA CGCCAAAAAC TCAATGTATT TCTGAGGAAG CGTGGTGCAT AATGCCACGC  11641

AGCGTCTGCA TAACTTTTAT TATTTCTTTT ATTAATCAAC AAAATTTTGT TTTTAACATT  11701

TC                                                                 11703
```

(2) INFORMATION FOR SEQ ID NO:9:

(i) SEQUENCE CHARACTERISTICS:
        (A) LENGTH: 2512 amino acids
        (B) TYPE: amino acid
        (D) TOPOLOGY: linear (ii) MOLECULE TYPE: protein (xi) SEQUENCE DESCRIPTION: SEQ ID NO:9:

```
Met Glu Lys Pro Val Val Asn Val Asp Val Pro Gln Ser Pro Phe
 1               5                  10                  15

Val Val Gln Leu Gln Lys Ser Phe Pro Gln Phe Glu Val Val Ala Gln
                20                  25                  30

Gln Val Thr Pro Asn Asp His Ala Asn Ala Arg Ala Phe Ser His Leu
            35                  40                  45

Ala Ser Lys Leu Ile Glu Leu Glu Val Pro Thr Thr Ala Thr Ile Leu
        50                  55                  60

Asp Ile Gly Ser Ala Pro Ala Arg Arg Met Phe Ser Glu His Gln Tyr
 65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
                100                 105                 110

Asn Leu His Glu Lys Ile Lys Asp Leu Arg Thr Val Leu Asp Thr Pro
            115                 120                 125

Asp Ala Glu Thr Pro Ser Leu Cys Phe His Asn Asp Val Thr Cys Asn
        130                 135                 140

Met Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
                180                 185                 190

Tyr Pro Ala Tyr Asn Thr Asn Trp Ala Asp Glu Lys Val Leu Glu Ala
            195                 200                 205

Arg Asn Ile Gly Leu Cys Ser Thr Lys Leu Ser Glu Gly Arg Thr Gly
        210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Asn Gly Lys Gln Ser
            260                 265                 270
```

-continued

```
Tyr Thr Cys Arg Cys Asp Thr Val Val Ser Cys Glu Gly Tyr Val Val
            275                 280                 285
Lys Lys Ile Thr Ile Ser Pro Gly Ile Thr Gly Glu Thr Val Gly Tyr
        290                 295                 300
Ala Val Thr His Asn Ser Glu Gly Phe Leu Leu Cys Lys Val Thr Asp
305                 310                 315                 320
Thr Val Lys Gly Glu Arg Val Ser Phe Pro Val Cys Thr Tyr Ile Pro
                325                 330                 335
Ala Thr Ile Cys Asp Gln Met Thr Gly Ile Met Ala Thr Asp Ile Ser
            340                 345                 350
Pro Asp Asp Ala Gln Lys Leu Leu Val Gly Leu Asn Gln Arg Ile Val
        355                 360                 365
Ile Asn Gly Arg Thr Asn Arg Asn Thr Asn Thr Met Gln Asn Tyr Leu
370                 375                 380
Leu Pro Ile Ile Ala Gln Gly Phe Ser Lys Trp Ala Lys Glu Arg Lys
385                 390                 395                 400
Asp Asp Leu Asp Asn Glu Lys Met Leu Gly Thr Arg Glu Arg Lys Leu
                405                 410                 415
Thr Tyr Gly Cys Leu Trp Ala Phe Arg Thr Lys Lys Val His Ser Phe
            420                 425                 430
Tyr Arg Pro Pro Gly Thr Gln Thr Ile Val Lys Val Pro Ala Ser Phe
        435                 440                 445
Ser Ala Phe Pro Met Ser Ser Val Trp Thr Thr Ser Leu Pro Met Ser
450                 455                 460
Leu Arg Gln Lys Leu Lys Leu Ala Leu Gln Pro Lys Lys Glu Glu Lys
465                 470                 475                 480
Leu Leu Gln Val Ser Glu Glu Leu Val Met Glu Ala Lys Ala Ala Phe
                485                 490                 495
Glu Asp Ala Gln Glu Glu Ala Arg Ala Glu Lys Leu Arg Glu Ala Leu
            500                 505                 510
Pro Pro Leu Val Ala Asp Lys Gly Ile Glu Ala Ala Glu Val Val
        515                 520                 525
Cys Glu Val Glu Gly Leu Gln Ala Asp Ile Gly Ala Ala Leu Val Glu
530                 535                 540
Thr Pro Arg Gly His Val Arg Ile Ile Pro Gln Ala Asn Asp Arg Met
545                 550                 555                 560
Ile Gly Gln Tyr Ile Val Val Ser Pro Asn Ser Val Leu Lys Asn Ala
                565                 570                 575
Lys Leu Ala Pro Ala His Pro Leu Ala Asp Gln Val Lys Ile Ile Thr
            580                 585                 590
His Ser Gly Arg Ser Gly Arg Tyr Ala Val Glu Pro Tyr Asp Ala Lys
        595                 600                 605
Val Leu Met Pro Ala Gly Gly Ala Val Pro Trp Pro Glu Phe Leu Ala
610                 615                 620
Leu Ser Glu Ser Ala Thr Leu Val Tyr Asn Glu Arg Glu Phe Val Asn
625                 630                 635                 640
Arg Lys Leu Tyr His Ile Ala Met His Gly Pro Ala Lys Asn Thr Glu
                645                 650                 655
Glu Glu Gln Tyr Lys Val Thr Lys Ala Glu Leu Ala Glu Thr Glu Tyr
            660                 665                 670
Val Phe Asp Val Asp Lys Lys Arg Cys Val Lys Lys Glu Glu Ala Ser
        675                 680                 685
Gly Leu Val Leu Ser Gly Glu Leu Thr Asn Pro Pro Tyr His Glu Leu
```

-continued

```
            690                 695                 700
Ala Leu Glu Gly Leu Lys Thr Arg Pro Ala Val Pro Tyr Lys Val Glu
705                     710                 715                 720

Thr Ile Gly Val Ile Gly Thr Pro Gly Ser Gly Lys Ser Ala Ile Ile
                    725                 730                 735

Lys Ser Thr Val Thr Ala Arg Asp Leu Val Thr Ser Gly Lys Lys Glu
                740                 745                 750

Asn Cys Arg Glu Ile Glu Ala Asp Val Leu Arg Leu Arg Gly Met Gln
                    755                 760                 765

Ile Thr Ser Lys Thr Val Asp Ser Val Met Leu Asn Gly Cys His Lys
770                 775                 780

Ala Val Glu Val Leu Tyr Val Asp Glu Ala Phe Ala Cys His Ala Gly
785                 790                 795                 800

Ala Leu Leu Ala Leu Ile Ala Ile Val Arg Pro Arg Lys Lys Val Val
                    805                 810                 815

Leu Cys Gly Asp Pro Met Gln Cys Gly Phe Phe Asn Met Met Gln Leu
                    820                 825                 830

Lys Val His Phe Asn His Pro Glu Lys Asp Ile Cys Thr Lys Thr Phe
                835                 840                 845

Tyr Lys Tyr Ile Ser Arg Arg Cys Thr Gln Pro Val Thr Ala Ile Val
850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
                    885                 890                 895

Asp Ile Ile Leu Thr Cys Phe Arg Gly Trp Val Lys Gln Leu Gln Ile
                900                 905                 910

Asp Tyr Pro Gly His Glu Val Met Thr Ala Ala Ser Gln Gly Leu
                915                 920                 925

Thr Arg Lys Gly Val Tyr Ala Val Arg Gln Lys Val Asn Glu Asn Pro
930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys
                965                 970                 975

Gln Leu Thr Asn Ile Pro Lys Gly Asn Phe Gln Ala Thr Ile Glu Asp
                980                 985                 990

Trp Glu Ala Glu His Lys Gly Ile Ile Ala Ile Asn Ser Pro Thr
            995                 1000                1005

Pro Arg Ala Asn Pro Phe Ser Cys Lys Thr Asn Val Cys Trp Ala Lys
        1010                1015                1020

Ala Leu Glu Pro Ile Leu Ala Thr Ala Gly Ile Val Leu Thr Gly Cys
1025                1030                1035                1040

Gln Trp Ser Glu Leu Phe Pro Gln Phe Ala Asp Asp Lys Pro His Ser
            1045                1050                1055

Ala Ile Tyr Ala Leu Asp Val Ile Cys Ile Lys Phe Phe Gly Met Asp
                1060                1065                1070

Leu Thr Ser Gly Leu Phe Ser Lys Gln Ser Ile Pro Leu Thr Tyr His
            1075                1080                1085

Pro Ala Asp Ser Ala Arg Pro Val Ala His Trp Asp Asn Ser Pro Gly
        1090                1095                1100

Thr Arg Lys Tyr Gly Tyr Asp His Ala Ile Ala Ala Glu Leu Ser Arg
1105                1110                1115                1120
```

```
Arg Phe Pro Val Phe Gln Leu Ala Gly Lys Gly Thr Gln Leu Asp Leu
            1125                1130                1135

Gln Thr Gly Arg Thr Arg Val Ile Ser Ala Gln His Asn Leu Val Pro
        1140                1145                1150

Val Asn Arg Asn Leu Pro His Ala Leu Val Pro Glu Tyr Lys Glu Lys
            1155                1160                1165

Gln Pro Gly Pro Val Glu Lys Phe Leu Asn Gln Phe Lys His His Ser
    1170                1175                1180

Val Leu Val Val Ser Glu Glu Lys Ile Glu Ala Pro Arg Lys Arg Ile
1185                1190                1195                1200

Glu Trp Ile Ala Pro Ile Gly Ile Ala Gly Ala Asp Lys Asn Tyr Asn
            1205                1210                1215

Leu Ala Phe Gly Phe Pro Pro Gln Ala Arg Tyr Asp Leu Val Phe Ile
            1220                1225                1230

Asn Ile Gly Thr Lys Tyr Arg Asn His His Phe Gln Gln Cys Glu Asp
            1235                1240                1245

His Ala Ala Thr Leu Lys Thr Leu Ser Arg Ser Ala Leu Asn Cys Leu
            1250                1255                1260

Asn Pro Gly Gly Thr Leu Val Val Lys Ser Tyr Gly Tyr Ala Asp Arg
1265                1270                1275                1280

Asn Ser Glu Asp Val Val Thr Ala Leu Ala Arg Lys Phe Val Arg Val
                1285                1290                1295

Ser Ala Ala Arg Pro Asp Cys Val Ser Ser Asn Thr Glu Met Tyr Leu
            1300                1305                1310

Ile Phe Arg Gln Leu Asp Asn Ser Arg Thr Arg Gln Phe Thr Pro His
            1315                1320                1325

His Leu Asn Cys Val Ile Ser Ser Val Tyr Glu Gly Thr Arg Asp Gly
            1330                1335                1340

Val Gly Ala Ala Pro Ser Tyr Arg Thr Lys Arg Glu Asn Ile Ala Asp
1345                1350                1355                1360

Cys Gln Glu Glu Ala Val Val Asn Ala Ala Asn Pro Leu Gly Arg Pro
            1365                1370                1375

Gly Glu Gly Val Cys Arg Ala Ile Tyr Lys Arg Trp Pro Thr Ser Phe
            1380                1385                1390

Thr Asp Ser Ala Thr Glu Thr Gly Thr Ala Arg Met Thr Val Cys Leu
        1395                1400                1405

Gly Lys Lys Val Ile His Ala Val Gly Pro Asp Phe Arg Lys His Pro
    1410                1415                1420

Glu Ala Glu Ala Leu Lys Leu Leu Gln Asn Ala Tyr His Ala Val Ala
1425                1430                1435                1440

Asp Leu Val Asn Glu His Asn Ile Lys Ser Val Ala Ile Pro Leu Leu
            1445                1450                1455

Ser Thr Gly Ile Tyr Ala Ala Gly Lys Asp Arg Leu Glu Val Ser Leu
            1460                1465                1470

Asn Cys Leu Thr Thr Ala Leu Asp Arg Thr Asp Ala Asp Val Thr Ile
        1475                1480                1485

Tyr Cys Leu Asp Lys Lys Trp Lys Glu Arg Ile Asp Ala Ala Leu Gln
    1490                1495                1500

Leu Lys Glu Ser Val Thr Glu Leu Lys Asp Glu Asp Met Glu Ile Asp
1505                1510                1515                1520

Asp Glu Leu Val Trp Ile His Pro Asp Ser Cys Leu Lys Gly Arg Lys
            1525                1530                1535
```

-continued

Gly Phe Ser Thr Thr Lys Gly Lys Leu Tyr Ser Tyr Phe Glu Gly Thr
        1540                  1545                  1550

Lys Phe His Gln Ala Ala Lys Asp Met Ala Glu Ile Lys Val Leu Phe
        1555                  1560                  1565

Pro Asn Asp Gln Glu Ser Asn Glu Gln Leu Cys Ala Tyr Ile Leu Gly
        1570                  1575                  1580

Glu Thr Met Glu Ala Ile Arg Glu Lys Cys Pro Val Asp His Asn Pro
1585                  1590                  1595                  1600

Ser Ser Ser Pro Pro Lys Thr Leu Pro Cys Leu Cys Met Tyr Ala Met
        1605                  1610                  1615

Thr Pro Glu Arg Val His Arg Leu Arg Ser Asn Asn Val Lys Glu Val
        1620                  1625                  1630

Thr Val Cys Ser Ser Thr Pro Leu Pro Lys His Lys Ile Lys Asn Val
        1635                  1640                  1645

Gln Lys Val Gln Cys Thr Lys Val Val Leu Phe Asn Pro His Thr Pro
        1650                  1655                  1660

Ala Phe Val Pro Ala Arg Lys Tyr Ile Glu Val Pro Glu Gln Pro Thr
1665                  1670                  1675                  1680

Ala Pro Pro Ala Gln Ala Glu Glu Ala Pro Glu Val Val Ala Thr Pro
        1685                  1690                  1695

Ser Pro Ser Thr Ala Asp Asn Ser Leu Asp Val Thr Asp Ile Ser
        1700                  1705                  1710

Leu Asp Met Asp Asp Ser Ser Glu Gly Ser Leu Phe Ser Ser Phe Ser
        1715                  1720                  1725

Gly Ser Asp Asn Ser Ile Thr Ser Met Asp Ser Trp Ser Ser Gly Pro
        1730                  1735                  1740

Ser Ser Leu Glu Ile Val Asp Arg Arg Gln Val Val Ala Asp Val
1745                  1750                  1755                  1760

His Ala Val Gln Glu Pro Ala Pro Ile Pro Pro Arg Leu Lys Lys
        1765                  1770                  1775

Met Ala Arg Leu Ala Ala Ala Arg Lys Glu Pro Thr Pro Pro Ala Ser
        1780                  1785                  1790

Asn Ser Ser Glu Ser Leu His Leu Ser Phe Gly Gly Val Ser Met Ser
        1795                  1800                  1805

Leu Gly Ser Ile Phe Asp Gly Glu Thr Ala Arg Gln Ala Ala Val Gln
        1810                  1815                  1820

Pro Leu Ala Thr Gly Pro Thr Asp Val Pro Met Ser Phe Gly Ser Phe
1825                  1830                  1835                  1840

Ser Asp Gly Glu Ile Asp Glu Leu Ser Arg Arg Val Thr Glu Ser Glu
                1845                  1850                  1855

Pro Val Leu Phe Gly Ser Phe Glu Pro Gly Glu Val Asn Ser Ile Ile
        1860                  1865                  1870

Ser Ser Arg Ser Ala Val Ser Phe Pro Leu Arg Lys Gln Arg Arg Arg
        1875                  1880                  1885

Arg Arg Ser Arg Arg Thr Glu Tyr Leu Thr Gly Val Gly Gly Tyr Ile
        1890                  1895                  1900

Phe Ser Thr Asp Thr Gly Pro Gly His Leu Gln Lys Lys Ser Val Leu
1905                  1910                  1915                  1920

Gln Asn Gln Leu Thr Glu Pro Thr Leu Glu Arg Asn Val Leu Glu Arg
        1925                  1930                  1935

Ile His Ala Pro Val Leu Asp Thr Ser Lys Glu Glu Gln Leu Lys Leu
        1940                  1945                  1950

Arg Tyr Gln Met Met Pro Thr Glu Ala Asn Lys Ser Arg Tyr Gln Ser

-continued

```
                1955                1960                1965
Arg Lys Val Glu Asn Gln Lys Ala Ile Thr Thr Glu Arg Leu Leu Ser
    1970                1975                1980

Gly Leu Arg Leu Tyr Asn Ser Ala Thr Asp Gln Pro Glu Cys Tyr Lys
1985                1990                1995                2000

Ile Thr Tyr Pro Lys Pro Leu Tyr Ser Ser Val Pro Ala Asn Tyr
                2005                2010                2015

Ser Asp Pro Gln Phe Ala Val Ala Val Cys Asn Asn Tyr Leu His Glu
            2020                2025                2030

Asn Tyr Pro Thr Val Ala Ser Tyr Gln Ile Thr Asp Glu Tyr Asp Ala
            2035                2040                2045

Tyr Leu Asp Met Val Asp Gly Thr Val Ala Cys Leu Asp Thr Ala Thr
    2050                2055                2060

Phe Cys Pro Ala Lys Leu Arg Ser Tyr Pro Lys Lys His Glu Tyr Arg
2065                2070                2075                2080

Ala Pro Asn Ile Arg Ser Ala Val Pro Ser Ala Met Gln Asn Thr Leu
                2085                2090                2095

Gln Asn Val Leu Ile Ala Ala Thr Lys Arg Asn Cys Asn Val Thr Gln
            2100                2105                2110

Met Arg Glu Leu Pro Thr Leu Asp Ser Ala Thr Phe Asn Val Glu Cys
        2115                2120                2125

Phe Arg Lys Tyr Ala Cys Asn Asp Glu Tyr Trp Glu Phe Ala Arg
    2130                2135                2140

Lys Pro Ile Arg Ile Thr Thr Glu Phe Val Thr Ala Tyr Val Ala Arg
2145                2150                2155                2160

Leu Lys Gly Pro Lys Ala Ala Leu Phe Ala Lys Thr Tyr Asn Leu
                2165                2170                2175

Val Pro Leu Gln Glu Val Pro Met Asp Arg Phe Val Met Asp Met Lys
            2180                2185                2190

Arg Asp Val Lys Val Thr Pro Gly Thr Lys His Thr Glu Glu Arg Pro
        2195                2200                2205

Lys Val Gln Val Ile Gln Ala Ala Glu Pro Leu Ala Thr Ala Tyr Leu
    2210                2215                2220

Cys Gly Ile His Arg Glu Leu Val Arg Arg Leu Thr Ala Val Leu Leu
2225                2230                2235                2240

Pro Asn Ile His Thr Leu Phe Asp Met Ser Ala Glu Asp Phe Asp Ala
                2245                2250                2255

Ile Ile Ala Glu His Phe Lys Gln Gly Asp Pro Val Leu Glu Thr Asp
            2260                2265                2270

Ile Ala Ser Phe Asp Lys Ser Gln Asp Asp Ala Met Ala Leu Thr Gly
        2275                2280                2285

Leu Met Ile Leu Glu Asp Leu Gly Val Asp Gln Pro Leu Leu Asp Leu
    2290                2295                2300

Ile Glu Cys Ala Phe Gly Glu Ile Ser Ser Thr His Leu Pro Thr Gly
2305                2310                2315                2320

Thr Arg Phe Lys Phe Gly Ala Met Met Lys Ser Gly Met Phe Leu Thr
                2325                2330                2335

Leu Phe Val Asn Thr Val Leu Asn Val Val Ile Ala Ser Arg Val Leu
            2340                2345                2350

Glu Glu Arg Leu Lys Thr Ser Arg Cys Ala Ala Phe Ile Gly Asp Asp
        2355                2360                2365

Asn Ile Ile His Gly Val Val Ser Asp Lys Glu Met Ala Glu Arg Cys
    2370                2375                2380
```

-continued

```
Ala Thr Trp Leu Asn Met Glu Val Lys Ile Ile Asp Ala Val Ile Gly
2385                2390                2395                2400

Glu Arg Pro Pro Tyr Phe Cys Gly Gly Phe Ile Leu Gln Asp Ser Val
                    2405                2410                2415

Thr Ser Thr Ala Cys Arg Val Ala Asp Pro Leu Lys Arg Leu Phe Lys
                2420                2425                2430

Leu Gly Lys Pro Leu Pro Ala Asp Asp Glu Gln Asp Glu Asp Arg Arg
            2435                2440                2445

Arg Ala Leu Leu Asp Glu Thr Lys Ala Trp Phe Arg Val Gly Ile Thr
        2450                2455                2460

Gly Thr Leu Ala Val Ala Val Thr Thr Arg Tyr Glu Val Asp Asn Ile
2465                2470                2475                2480

Thr Pro Val Leu Leu Ala Leu Arg Thr Phe Ala Gln Ser Lys Arg Ala
                2485                2490                2495

Phe Gln Ala Ile Arg Gly Glu Ile Lys His Leu Tyr Gly Gly Pro Lys
                2500                2505                2510

(2) INFORMATION FOR SEQ ID NO:10:

(i) SEQUENCE CHARACTERISTICS:
        (A) LENGTH: 1245 amino acids
        (B) TYPE: amino acid
        (D) TOPOLOGY: linear (ii) MOLECULE TYPE: protein (xi) SEQUENCE DESCRIPTION: SEQ ID NO:10:

Met Asn Arg Gly Phe Phe Asn Met Leu Gly Arg Arg Pro Phe Pro Ala
1               5                   10                  15

Pro Thr Ala Met Trp Arg Pro Arg Arg Arg Gln Ala Ala Pro Met
                20                  25                  30

Pro Ala Arg Asn Gly Leu Ala Ser Gln Ile Gln Gln Leu Thr Thr Ala
            35                  40                  45

Val Ser Ala Leu Val Ile Gly Gln Ala Thr Arg Pro Gln Pro Pro Arg
        50                  55                  60

Pro Arg Pro Pro Arg Gln Lys Lys Gln Ala Pro Lys Gln Pro Pro
65                  70                  75                  80

Lys Pro Lys Lys Pro Lys Thr Gln Glu Lys Lys Lys Gln Pro Ala
                85                  90                  95

Lys Pro Lys Pro Gly Lys Arg Gln Arg Met Ala Leu Lys Leu Glu Ala
            100                 105                 110

Asp Arg Leu Phe Asp Val Lys Asn Glu Asp Gly Asp Val Ile Gly His
            115                 120                 125

Ala Leu Ala Met Glu Gly Lys Val Met Lys Pro Leu His Val Lys Gly
130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
                165                 170                 175

Ala Phe Thr Tyr Thr Ser Glu His Pro Glu Gly Phe Tyr Asn Trp His
                180                 185                 190

His Gly Ala Val Gln Tyr Ser Gly Gly Arg Phe Thr Ile Pro Arg Gly
            195                 200                 205

Val Gly Gly Arg Gly Asp Ser Gly Arg Pro Ile Met Asp Asn Ser Gly
        210                 215                 220
```

-continued

```
Arg Val Ala Ile Val Leu Gly Gly Ala Asp Glu Gly Thr Arg Thr
225                 230                 235                 240

Ala Leu Ser Val Val Thr Trp Asn Ser Lys Gly Lys Thr Ile Lys Thr
            245                 250                 255

Thr Pro Glu Gly Thr Glu Trp Ser Ala Ala Pro Leu Val Thr Ala
        260                 265                 270

Met Cys Leu Leu Gly Asn Val Ser Phe Pro Cys Asp Arg Pro Pro Thr
        275                 280                 285

Cys Tyr Thr Arg Glu Pro Ser Arg Ala Leu Asp Ile Leu Glu Glu Asn
    290                 295                 300

Val Asn His Glu Ala Tyr Asp Thr Leu Leu Asn Ala Ile Leu Arg Cys
305                 310                 315                 320

Gly Ser Ser Gly Arg Ser Lys Arg Ser Val Thr Asp Asp Phe Thr Leu
                325                 330                 335

Thr Ser Pro Tyr Leu Gly Thr Cys Ser Tyr Cys His His Thr Glu Pro
            340                 345                 350

Cys Phe Ser Pro Val Lys Ile Glu Gln Val Trp Asp Glu Ala Asp Asp
        355                 360                 365

Asn Thr Ile Arg Ile Gln Thr Ser Ala Gln Phe Gly Tyr Asp Gln Ser
    370                 375                 380

Gly Ala Ala Ser Ala Asn Lys Tyr Arg Tyr Met Ser Leu Glu Gln Asp
385                 390                 395                 400

His Thr Val Lys Glu Gly Thr Met Asp Asp Ile Lys Ile Ser Thr Ser
                405                 410                 415

Gly Pro Cys Arg Arg Leu Ser Tyr Lys Gly Tyr Phe Leu Leu Ala Lys
            420                 425                 430

Cys Pro Pro Gly Asp Ser Val Thr Val Ser Ile Val Ser Ser Asn Ser
        435                 440                 445

Ala Thr Ser Cys Thr Leu Ala Arg Lys Ile Lys Pro Lys Phe Val Gly
    450                 455                 460

Arg Glu Lys Tyr Asp Leu Pro Pro Val His Gly Lys Lys Ile Pro Cys
465                 470                 475                 480

Thr Val Tyr Asp Arg Leu Lys Glu Thr Thr Ala Gly Tyr Ile Thr Met
                485                 490                 495

His Arg Pro Gly Pro His Ala Tyr Thr Ser Tyr Leu Glu Glu Ser Ser
            500                 505                 510

Gly Lys Val Tyr Ala Lys Pro Pro Ser Gly Lys Asn Ile Thr Tyr Glu
        515                 520                 525

Cys Lys Cys Gly Asp Tyr Lys Thr Gly Thr Val Ser Thr Arg Thr Glu
    530                 535                 540

Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Leu Ile Arg His Asp Asp
                565                 570                 575

His Thr Ala Gln Gly Lys Leu His Leu Pro Phe Lys Leu Ile Pro Ser
            580                 585                 590

Thr Cys Met Val Pro Val Ala His Ala Pro Asn Val Ile His Gly Phe
        595                 600                 605

Lys His Ile Ser Leu Gln Leu Asp Thr Asp His Leu Thr Leu Leu Thr
    610                 615                 620

Thr Arg Arg Leu Gly Ala Asn Pro Glu Pro Thr Thr Glu Trp Ile Val
625                 630                 635                 640

Gly Lys Thr Val Arg Asn Phe Thr Val Asp Arg Asp Gly Leu Glu Tyr
```

-continued

```
                645                 650                 655
Ile Trp Gly Asn His Glu Pro Val Arg Val Tyr Ala Gln Glu Ser Ala
            660                 665                 670
Pro Gly Asp Pro His Gly Trp Pro His Glu Ile Val Gln His Tyr Tyr
            675                 680                 685
His Arg His Pro Val Tyr Thr Ile Leu Ala Val Ala Ser Ala Thr Val
            690                 695                 700
Ala Met Met Ile Gly Val Thr Val Ala Val Leu Cys Ala Cys Lys Ala
705                 710                 715                 720
Arg Arg Glu Cys Leu Thr Pro Tyr Ala Leu Ala Pro Asn Ala Val Ile
                725                 730                 735
Pro Thr Ser Leu Ala Leu Leu Cys Cys Val Arg Ser Ala Asn Ala Glu
                740                 745                 750
Thr Phe Thr Glu Thr Met Ser Tyr Leu Trp Ser Asn Ser Gln Pro Phe
            755                 760                 765
Phe Trp Val Gln Leu Cys Ile Pro Leu Ala Ala Phe Ile Val Leu Met
770                 775                 780
Arg Cys Cys Ser Cys Leu Pro Phe Leu Val Val Ala Gly Ala Tyr
785                 790                 795                 800
Leu Ala Lys Val Asp Ala Tyr Glu His Ala Thr Thr Val Pro Asn Val
                805                 810                 815
Pro Gln Ile Pro Tyr Lys Ala Leu Val Glu Arg Ala Gly Tyr Ala Pro
            820                 825                 830
Leu Asn Leu Glu Ile Thr Val Met Ser Ser Glu Val Leu Pro Ser Thr
            835                 840                 845
Asn Gln Glu Tyr Ile Thr Cys Lys Phe Thr Thr Val Val Pro Ser Pro
850                 855                 860
Lys Ile Lys Cys Cys Gly Ser Leu Glu Cys Gln Pro Ala Ala His Ala
865                 870                 875                 880
Asp Tyr Thr Cys Lys Val Phe Gly Gly Val Tyr Pro Phe Met Trp Gly
                885                 890                 895
Gly Ala Gln Cys Phe Cys Asp Ser Glu Asn Ser Gln Met Ser Glu Ala
            900                 905                 910
Tyr Val Glu Leu Ser Ala Asp Cys Ala Ser Asp His Ala Gln Ala Ile
            915                 920                 925
Lys Val His Thr Ala Ala Met Lys Val Gly Leu Arg Ile Val Tyr Gly
930                 935                 940
Asn Thr Thr Ser Phe Leu Asp Val Tyr Val Asn Gly Val Thr Pro Gly
945                 950                 955                 960
Thr Ser Lys Asp Leu Lys Val Ile Ala Gly Pro Ile Ser Ala Ser Phe
                965                 970                 975
Thr Pro Phe Asp His Lys Val Val Ile His Arg Gly Leu Val Tyr Asn
            980                 985                 990
Tyr Asp Phe Pro Glu Tyr Gly Ala Met Lys Pro Gly Ala Phe Gly Asp
            995                 1000                1005
Ile Gln Ala Thr Ser Leu Thr Ser Lys Asp Leu Ile Ala Ser Thr Asp
            1010                1015                1020
Ile Arg Leu Leu Lys Pro Ser Ala Lys Asn Val His Val Pro Tyr Thr
1025                1030                1035                1040
Gln Ala Ala Ser Gly Phe Glu Met Trp Lys Asn Asn Ser Gly Arg Pro
                1045                1050                1055
Leu Gln Glu Thr Ala Pro Phe Gly Cys Lys Ile Ala Val Asn Pro Leu
                1060                1065                1070
```

-continued

```
Arg Ala Val Asp Cys Ser Tyr Gly Asn Ile Pro Ile Ser Ile Asp Ile
        1075                1080                1085
Pro Asn Ala Ala Phe Ile Arg Thr Ser Asp Ala Pro Leu Val Ser Thr
    1090                1095                1100
Val Lys Cys Glu Val Ser Glu Cys Thr Tyr Ser Ala Asp Phe Gly Gly
1105                1110                1115                1120
Met Ala Thr Leu Gln Tyr Val Ser Asp Arg Glu Gly Gln Cys Pro Val
                1125                1130                1135
His Ser His Ser Ser Thr Ala Thr Leu Gln Glu Ser Thr Val His Val
            1140                1145                1150

Leu Glu Lys Gly Ala Val Thr Val His Phe Ser Thr Ala Ser Pro Gln
        1155                1160                1165
Ala Asn Phe Ile Val Ser Leu Cys Gly Lys Lys Thr Thr Cys Asn Ala
    1170                1175                1180
Glu Cys Lys Pro Pro Ala Asp His Ile Val Ser Thr Pro His Lys Asn
1185                1190                1195                1200
Asp Gln Glu Phe Gln Ala Ala Ile Ser Lys Thr Ser Trp Ser Trp Leu
                1205                1210                1215
Phe Ala Leu Phe Gly Gly Ala Ser Ser Leu Leu Ile Ile Gly Leu Met
            1220                1225                1230

Ile Phe Ala Cys Ser Met Met Leu Thr Ser Thr Arg Arg
        1235                1240                1245
```

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:11:

CTGCGGCGGA TTCATCTTGC 20

(2) INFORMATION FOR SEQ ID NO:12:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(xi) SEQUENCE DESCRIPTION: SEQ ID NO:12:

CTCCAACTTA AGTG 14

US 6,583,121 B1

SYSTEM FOR THE IN VIVO DELIVERY AND EXPRESSION OF HETEROLOGOUS GENES IN THE BONE MARROW

RELATED APPLICATION INFORMATION

This application is filed under 35 U.S.C. §371 of PCT Application No. PCT/US98/02945, filed on Feb. 18, 1999, the disclosure of which is incorporated by reference herein in its entirety, which is a continuation-in-part of co-pending U.S. application Ser. No. 08/801,263, filed on Feb. 19, 1997, which issued as U.S. Pat. No. 5,811,407, the disclosure of which is incorporated by reference herein in its entirety.

FEDERALLY SPONSORED RESEARCH

This invention was made with Government support under Grant Number 5 RO1 AI22186 from the National Institutes of Health. The Government has certain rights to this invention.

FIELD OF THE INVENTION

The present invention relates to recombinant DNA technology, and in particular to introducing and expressing foreign DNA in a eukaryotic cell.

BACKGROUND OF THE INVENTION

The Alphavirus genus includes a variety of viruses all of which are members of the Togaviridae family. The alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86 (S.A.AR86), Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus.

The alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1-nsP4) and the second encodes the viral structural proteins. Strauss and Strauss, Microbiological Rev. 58, 491–562, 494 (1994). Structural subunits consisting of a single viral protein, C, associate with themselves and with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2. See Paredes et al., Proc. Natl. Acad. Sci. USA 90, 9095–99 (1993); Paredes et al. Virology 187, 324–32 (1993); Pedersen et al., J. Virol. 14:40 (1974).

Sindbis virus, the prototype member of the alphavirus genus of the family Togaviridae, and viruses related to Sindbis are broadly distributed throughout Africa, Europe, Asia, the Indian subcontinent, and Australia, based on serological surveys of humans, domestic animals and wild birds. Kokemot et al., Trans. R. Soc. Trop Med. Hyg. 59, 553–62 (1965); Redaksie, S. Aft. Med. J. 42, 197 (1968); Adekolu-John and Fagbami, Trans. R. Soc. Trop. Med. Hyg. 77, 149–51 (1983); Darwish et al., Trans. R. Soc. Trop. Med. Hyg. 77, 442–45 (1983); Lundström et al., Epidemiol. Infect. 106, 567–74 (1991); Morrill et al., J. Trop. Med. Hyg. 94, 166–68 (1991). The first isolate of Sindbis virus (strain AR339) was recovered from a pool of Culex sp. mosquitoes collected in Sindbis, Egypt in 1953 (Taylor et al., Am. J. Trop. Med. Hyg. 4, 844–62 (1955)), and is the most extensively studied representative of this group. Other members of the Sindbis group of alphaviruses include South African Arbovirus No. 86, Ockelbo82, and Girdwood S.A. These viruses are not strains of the Sindbis virus; they are related to Sindbis AR339, but they are more closely related to each other based on nucleotide sequence and serological comparisons. Lundström et al., J. Wildl. Dis. 29, 189–95 (1993); Simpson et al., Virology 222, 464–69 (1996). Ockelbo82, S.A.AR86 and Girdwood S.A. are all associated with human disease, whereas Sindbis is not. The clinical symptoms of human infection with Ockelbo82, S.A.AR86, or Girdwood S.A. are a febrile illness, general malaise, macropapular rash, and joint pain that occasionally progresses to a polyarthralgia sometimes lasting from a few months to a few years.

The study of these viruses has led to the development of beneficial techniques for vaccinating against the alphavirus diseases, and other diseases through the use of alphavirus vectors for the introduction of foreign DNA. See U.S. Pat. No. 5,185,440 to Davis et al., and PCT Publication WO 92/10578. It is intended that all United States patent references be incorporated in their entirety by reference.

It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens of such agents into a vaccine strain of another virus. One such system utilizing a live VEE vector is described in U.S. Pat. No. 5,505,947 to Johnston et al.

Sindbis virus vaccines have been employed as viral carriers in virus constructs which express genes encoding immunizing antigens for other viruses. See U.S. Pat. No. 5,217,879 to Huang et al. Huang et al. describes Sindbis infectious viral vectors. However, the reference does not describe the cDNA sequence of Girdwood S.A. and TR339, nor clones or viral vectors produced therefrom.

Another such system is described by Hahn et al., Proc. Natl. Acad. Sci. USA 89:2679 (1992), wherein Sindbis virus constructs which express a truncated form of the influenza hemagglutinin protein are described. The constructs are used to study antigen processing and presentation in vitro and in mice. Although no infectious challenge dose is tested, it is also suggested that such constructs might be used to produce protective B- and T-cell mediated immunity.

London et al., Proc. Natl. Acad; Sci, USA 89, 207–11 (1992), disclose a method of producing an immune response in mice against a lethal Rift Valley Fever (RVF) virus by infecting the mice with an infectious Sindbis virus containing an RVF epitope. London does not disclose using Girdwood S.A. or TR339 to induce an immune response in animals.

Viral carriers can also be used to introduce and express foreign DNA in eukaryotic cells. One goal of such techniques is to employ vectors that target expression to particular cells and/or tissues. A current approach has been to remove target cells from the body, culture them ex vivo, infect them with an expression vector, and then reintroduce them into the patient.

PCT Publication No. WO 92/10578 to Garoff and Liljestrom provide a system for introducing and expressing foreign proteins in animal cells using alphaviruses. This reference discloses the use of Semliki Forest virus to introduce and express foreign proteins in animal cells. The use of Girdwood S.A. or TR339 is not discussed. Furthermore, this reference does not provide a method of targeting and introducing foreign DNA into specific cell or tissue types.

Accordingly, there remains a need in the art for full-length cDNA clones of positive-strand RNA viruses, such as Girdwood S.A and TR339. In addition, there is an ongoing need in the art for improved vaccination strategies. Finally, there remains a need in the art for improved methods and nucleic acid sequences for delivering foreign DNA to target cells.

SUMMARY OF THE INVENTION

A first aspect of the present invention is a method of introducing and expressing heterologous RNA in bone marrow cells, comprising: (a) providing a recombinant alphavirus, the alphavirus containing a heterologous RNA segment, the heterologous RNA segment comprising a promoter operable in bone marrow cells operatively associated with a heterologous RNA to be expressed in bone marrow cells; and then (b) contacting the recombinant alphavirus to the bone marrow cells so that the heterologous RNA segment is introduced and expressed therein.

As a second aspect, the present invention provides a helper cell for expressing an infectious, propagation defective, Girdwood S.A. virus particle, comprising, in a Girdwood S.A.-permissive cell: (a) a first helper RNA encoding (i) at least one Girdwood S.A. structural protein, and (ii) not encoding at least one other Girdwood S.A. structural protein; and (b) a second helper RNA separate from the first helper RNA, the second helper RNA (i) not encoding the at least one Girdwood S.A. structural protein encoded by the first helper RNA, and (ii) encoding the at least one other Girdwood S.A. structural protein not encoded by the first helper RNA, and with all of the Girdwood S.A. structural proteins encoded by the first and second helper RNAs assembling together into Girdwood S.A. particles in the cell containing the replicon RNA; and wherein the Girdwood S.A. packaging segment is deleted from at least the first helper RNA.

A third aspect of the present invention is a method of making infectious, propagation defective, Girdwood S.A. virus particles, comprising: transfecting a Girdwood S.A.-permissive cell with a propagation defective replicon RNA, the replicon RNA including the Girdwood S.A. packaging segment and an inserted heterologous RNA; producing the Girdwood S.A. virus particles in the transfected cell; and then collecting the Girdwood S.A. virus particles from the cell. Also disclosed are infectious Girdwood S.A. RNAs, cDNAs encoding the same, infectious Girdwood S.A. virus particles, and pharmaceutical formulations thereof.

As a fourth aspect, the present invention provides a helper cell for expressing an infectious, propagation defective, TR339 virus particle, comprising, in a TR339-permissive cell: (a) a first helper RNA encoding (i) at least one TR339 structural protein, and (ii) not encoding at least one other TR339 structural protein; and (b) a second helper RNA separate from the first helper RNA, the second helper RNA (i) not encoding the at least one TR339 structural protein encoded by the first helper RNA, and (ii) encoding the at least one other TR339 structural protein not encoded by the first helper RNA, and with all of the TR339 structural proteins encoded by the first and second helper RNAs assembling together into TR339 particles in the cell containing the replicon RNA; and wherein the TR339 packaging segment is deleted from at least the first helper RNA.

A fifth aspect of the present invention is a method of making infectious, propagation defective, TR339 virus particles, comprising: transfecting a TR339-permissive cell with a propagation defective replicon RNA, the replicon RNA including the TR339 packaging segment and an inserted heterologous RNA; producing the TR339 virus particles in the transfected cell; and then collecting the TR339 virus particles from the cell. Also disclosed are infectious TR339 RNAs, cDNAs encoding the same, infectious TR339 virus particles, and pharmaceutical formulations thereof.

As a sixth aspect, the present invention provides a recombinant DNA comprising a cDNA coding for an infectious Girdwood S.A. virus RNA transcript, and a heterologous promoter positioned upstream from the cDNA and operatively associated therewith. The present invention also provides infectious RNA transcripts encoded by the above-mentioned cDNA and infectious viral particles containing the infectious RNA transcripts.

As a seventh aspect, the present invention provides a recombinant DNA comprising a cDNA coding for a Sindbis strain TR339 RNA transcript, and a heterologous promoter positioned upstream from the cDNA and operatively associated therewith. The present invention also provides infectious RNA transcripts encoded by the above-mentioned cDNA and infectious viral particles containing the infectious RNA transcripts.

The foregoing and other aspects of the present invention are described in the detailed description set forth below.

DETAILED DESCRIPTION OF THE INVENTION

The production and use of recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877, 729 to Clark et al. at Col. 4 line 38 to Col. 7 line 6; U.S. Pat. No. 4,912,038 to Schilling at Col 3 line 26 to Col 14 line 12; and U.S. Pat. No. 4,879,224 to Wallner at Col. 6 line 8 to Col. 8 line 59.

The term "alphavirus" has its conventional meaning in the art, and includes the various species of alphaviruses such as Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86, Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzlagach virus, Highlands J virus, Fort Morgan virus, Ndumu virus, Buggy Creek virus, and any other virus classified by the International Committee on Taxonomy of Viruses (ICTV) as an alphavirus. The preferred alphaviruses for use in the present invention include Sindbis virus strains (e.g., TR339), Girdwood S.A., S.A.AR86, and Ockelbo82.

An "Old World alphavirus" is a virus that is primarily distributed throughout the Old World. Alternately stated, an Old World alphavirus is a virus that is primarily distributed throughout Africa, Asia, Australia and New Zealand, or Europe. Exemplary Old World viruses include SF group alphaviruses and SIN group alphaviruses. SF group alphaviruses include Semliki Forest virus, Middelburg virus, Chikungunya virus, O'Nyong-Nyong virus, Ross River virus, Barmah Forest virus, Getah virus, Sagiyama virus, Bebaru virus, Mayaro virus, and Una virus. SIN group alphaviruses include Sindbis virus, South African Arbovirus No. 86, Ockelbo virus, Girdwood S.A. virus, Aura virus, Whataroa virus, Babanki virus, and Kyzylagach virus.

Acceptable alphaviruses include those containing attenuating mutations. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., a loss of virulence), in accordance with standard terminology in the art, whether the mutation be a substitution mutation or an in-frame deletion mutation. See, e.g., B. DAVIS ET AL., MICROBIOLOGY 132 (3d ed. 1980). The phrase "attenuating mutation" excludes mutations or combinations of mutations which would be lethal to the virus.

Appropriate attenuating mutations will be dependent upon the alphavirus used. Suitable attenuating mutations within the alphavirus genome will be known to those skilled in the art. Exemplary attenuating mutations include, but are not limited to, those described in U.S. Pat. No. 5,505,947 to Johnston et al., copending U.S. application Ser. No. 08/448,630 to Johnston et al., and copending U.S. application Ser. No. 08/446,9 32 to Johnston et al. it is intended that all United States patent references be incorporated in their entirety by reference.

Attenuating mutations may be introduced into the RNA by performing site-directed mutagenesis on the cDNA which encodes the RNA, in accordance with known procedures. See, Kunkel, *Proc. Natl. Acad. Sci. USA* 82, 488 (1985), the disclosure of which is incorporated herein by reference in its entirety. Alternatively, mutations may be introduced into the RNA by replacement of homologous restriction fragments in the cDNA which encodes for the RNA, in accordance with known procedures.

I. Methods for Introducing and Expressing Heterologous RNA in Bone Marrow Cells The present invention provides methods of using a recombinant alphavirus to introduce and express a heterologous RNA in bone marrow cells. Such methods are useful as vaccination strategies when the heterologous RNA encodes an immunogenic protein or peptide. Alternatively, such methods are useful in introducing and expressing in bone marrow cells an RNA which encodes a desirable protein or peptide, for example, a therapeutic protein or peptide.

The present invention is carried out using a recombinant alphavirus to introduce a heterologous RNA into bone marrow cells. Any alphavirus that targets and infects bone marrow cells is suitable. Preferred alphaviruses include Old World alphaviruses, more preferably SF group alphaviruses and SIN group alphaviruses, more preferably Sindbis virus strains (e.g., TR339), S.A.AR86 virus, Girdwood S.A. virus, and Ockelbo virus. In a more preferred embodiment, the alphavirus contains one or more attenuating mutations, as described hereinabove.

Two types of recombinant virus vector are contemplated in carrying out the present invention. In one embodiment employing "double promoter vectors," the heterologous RNA is inserted into a replication and propagation competent virus. Double promoter vectors are described in U.S. Pat. No. 5,505,947 to Johnston et al. With this type of viral vector, it is preferable that heterologous RNA sequences of less than 3 kilobases are inserted into the viral vector, more preferably those less than 2 kilobases, and more preferably still those less than 1 kilobase. In an alternate embodiment, propagation-defective "replicon vectors," as described in copending U.S. application Ser. No. 08/448,630 to Johnston et al., will be used. One advantage of replicon viral vectors is that larger RNA inserts, up to approximately 4–5 kilobases in length can be utilized. Double promoter vectors and replicon vectors are described in more detail hereinbelow.

The recombinant alphaviruses of the claimed method target the heterologous RNA to bone marrow cells, where it expresses the encoded protein or peptide. Heterologous RNA can be introduced and expressed in any cell type found in the bone marrow. Bone marrow cells that may be targeted by the recombinant alphaviruses of the present invention include, but are not limited to, polymorphonuclear cells, hemopoietic stem cells (including megakaryocyte colony forming units (CFU-M), spleen colony forming units (CFU-S), erythroid colony forming units (CFU-E), erythroid burst forming units (BFU-E), and colony forming units in culture (CFU-C), erythrocytes, macrophages (including reticular cells), monocytes, granulocytes, megakaryoctyes, lymphocytes, fibroblasts, osteoprogenitor cells, osteoblasts, osteoclasts, marrow stromal cells, chondrocytes and other cells of synovial joints. Preferably, marrow cells within the endosteum are targeted, more preferably osteoblasts. Also preferred are methods in which cells in the endosteum of synovial joints (e.g., hip and knee joints) are targeted.

By targeting to the cells of the bone marrow, it is meant that the primary site in which the virus will be localized in vivo is the cells of the bone marrow. Alternately stated, the alphaviruses of the present invention target bone marrow cells, such that titers in bone marrow two days after infection are greater than 100 PFU/g crushed bone, preferably greater than 200 PFU/g crushed bone, more preferably greater than 300 PFU/g crushed bone, and more preferably still greater than 500 PFU/g crushed bone. Virus may be detected occasionally in other cell or tissue types, but only sporadically and usually at low levels. Virus localization in the bone marrow can be demonstrated by any suitable technique known in the art, such as in situ hybridization.

Bone marrow cells are long-lived and harbor infectious alphaviruses for a prolonged period of time, as demonstrated in the Examples below. These characteristics of bone marrow cells render the present invention useful not only for the purpose of supplying a desired protein or peptide to skeletal tissue, but also for expressing proteins or peptides in vivo that are needed by other cell or tissue types.

The present invention can be carried out in vivo or with cultured bone marrow cells in vitro. Bone marrow cell cultures include primary cultures of bone marrow cells, serially-passaged cultures of bone marrow cells, and cultures of immortalized bone marrow cell lines. Bone marrow cells may be cultured by any suitable means known in the art.

The recombinant alphaviruses of the present invention carry a heterologous RNA segment. The heterologous RNA segment encodes a promoter and an inserted heterologous RNA. The inserted heterologous RNA may encode any protein or a peptide which is desirably expressed by the host bone marrow cells. Suitable heterologous RNA may be of prokaryotic (e.g., RNA encoding the Botulinus toxin C), or eukaryotic (e.g., RNA encoding malaria Plasmodium protein cs1) origin. Illustrative proteins and peptides encoded by the heterologous RNAs of the present invention include hormones, growth factors, interleukins, cytokines, chemokines, enzymes, and ribozymes. Alternately, the heterologous RNAs encode any therapeutic protein or peptide. As a further alternative, the heterologous RNAs of the present invention encode any immunogenic protein or peptide.

An immunogenic protein or peptide, or "immunogen," may be any protein or peptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV envelope GP160 protein and the HIV matrix/capsid proteins). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia), a flavivirus immunogen (e.g., a yellow fever virus immunogen or a Japanese encephalitis virus immunogen), a filovirus immunogen (e.g., an Ebola virus immunogen, or a Marburg virus immunogen), a bunyavirus immunogen (e.g., RVFV, CCHF, and SFS viruses), or a coronavirus immunogen (e.g., an infectious human coronavirus immunogen, such as the human coronavirus envelope glycoprotein gene, or a transmissible gastroenteritis virus immunogen for pigs, or an infectious bronchitis virus immunogen for chickens).

Alternatively, the present invention can be used to express heterologous RNAs encoding antisense oligonucleotides. In general, "antisense" refers to the use of small, synthetic oligonucleotides to inhibit gene expression by inhibiting the function of the target MRNA containing the complementary sequence. Milligan, J. F. et al., *J. Med. Chem.* 36(14), 1923–1937 (1993). Gene expression is inhibited through hybridization to coding (sense) sequences in a specific mRNA target by hydrogen bonding according to Watson-Crick base pairing rules. The mechanism of antisense inhibition is that the exogenously applied oligonucleotides decrease the mRNA and protein levels of the target gene. Milligan, J. F. et al., *J. Med. Chem.* 36(14), 1923–1937 (1993). See also Helene, C. and Toulme, *J., Biochim. Biophys. Acta* 1049, 99–125 (1990); Cohen, J. S., Ed., OLIGODEOXYNUCLEOTIDES AS ANTISENSE INHIBITORS OF GENE EXPRESSION, CRC Press:Boca Raton, Fla. (1987).

Antisense oligonucleotides may be of any suitable length, depending on the particular target being bound. The only limits on the length of the antisense oligonucleotide is thecapacity of the virus for inserted heterologous RNA. Antisense oligonucleotides may be complementary to the entire mRNA transcript of the target gene or only a portion thereof. Preferably the antisense oligonucleotide is directed to an mRNA region containing a junction between intron and exon. Where the antisense oligonucleotide is directed to an intron/exon junction, it may either entirely overlie the junction or may be sufficiently close to the junction to inhibit splicing out of the intervening exon during processing of precursor mRNA to mature mRNA (e.g., with the 3' or 5' terminus of the antisense oligonucleotide being positioned within about, for example, 10, 5, 3 or 2 nucleotides of the intron/exon junction). Also preferred are antisense oligonucleotides which overlap the initiation codon.

When practicing the present invention, the antisense oligonucleotides administered may be related in origin to the species to which it is administered. When treating humans, human antisense may be used if desired.

Promoters for use in carrying out the present invention are operable in bone marrow cells. An operable promoter in bone marrow cells is a promoter that is recognized by and functions in bone marrow cells. Promoters for use with the present invention must also be operatively associated with the heterologous RNA to be expressed in the bone marrow. A promoter is operably linked to a heterologous RNA if it controls the transcription of the heterologous RNA, where the heterologous RNA comprises a coding sequence. Suitable promoters are well known in the art. The Sindbis 26S promoter is preferred when the alphavirus is a strain of Sindbis virus. Additional preferred promoters beyond the Sindbis 26S promoter include the Girdwood S.A. 26S promoter when the alphavirus is Girdwood S.A., the S.A.AR86 26S promoter when the alphavirus is S.A.AR86, and any other promoter sequence recognized by alphavirus polymerases. Alphavirus promoter sequences containing mutations which alter the activity level of the promoter (in relation to the activity level of the wild-type) are also suitable in the practice of the present invention. Such mutant promoter sequences are described in Raju and Huang, *J. Virol.* 65, 2501–2510 (1991), the disclosure of which is incorporated in its entirety by reference.

The heterologous RNA is introduced into the bone marrow cells by contacting the recombinant alphavirus carrying the heterologous RNA segment to the bone marrow cells. By contacting, it is meant bringing the recombinant alphavirus and the bone marrow cells in physical proximity. The contacting step can be performed in vitro or in vivo. In vitro contacting can be carried out with cultures of immortalized or non-immortalized bone marrow cells. In one particular embodiment, bone marrow cells can be removed from a subject, cultured in vitro, infected with the vector, and then introduced back into the subject. Contacting is performed in vivo when the recombinant alphavirus is administered to a subject. Pharmaceutical formulations of recombinant alphavirus can be administered to a subject parenterally (e.g., subcutaneous, intracerebral, intradermal, intramuscular, intravenous and intraarticular) administration. Alternatively, pharmaceutical formulations of the present invention may be suitable for administration to the mucus membranes of a subject (e.g., intranasal administration, by use of a dropper, swab, or inhaler). Methods of preparing infectious virus particles and pharmaceutical formulations thereof are discussed in more detail hereinbelow.

By "introducing" the heterologous RNA segment into the bone marrow cells it is meant infecting the bone marrow cells with recombinant alphavirus containing the heterologous RNA, such that the viral vector carrying the heterologous RNA enters the bone marrow cells and can be expressed therein. As used with respect to the present invention, when the heterologous RNA is "expressed," it is meant that the heterologous RNA is transcribed. In particular embodiments of the invention in which it is desired to produce a protein or peptide, expression further includes the steps of post-transcriptional processing and translation of the mRNA transcribed from the heterologous RNA. In contrast, where the heterologous RNA encodes an antisense oligonucleotide, expression need not include post-transcriptional processing and translation. With respect to embodiments in which the heterologous RNA encodes an immunogenic protein or a protein being administered for therapeutic purposes, expression may also include the further step of post-translational processing to produce an immunogenic or therapeutically-active protein.

The present invention also provides infectious RNAs, as described hereinabove, and cDNAs encoding the same. Preferably the infectious RNAs and cDNAs are derived from the S.A.AR86, Girdwood S.A., TR339, or Ockelbo viruses. The cDNA clones can be generated by any of a variety of suitable methods known to those skilled in the art. A preferred method is the method set forth in U.S. Pat. No. 5,185,440 to Davis et al., the disclosure of which is incorporated in its entirety by reference, and Gubler et al., Gene 25:263 (1983).

RNA is preferably synthesized from the DNA sequence in vitro using purified RNA polymerase in the presence of ribonucleotide triphosphates and cap analogs in accordance with conventional techniques. However, the RNA may also be synthesized intracellularly after introduction of the cDNA.

A. Double Promoter Vectors.

In one embodiment of the invention, double promoter vectors are used to introduce the heterologous RNA into the target bone marrow cells. A double promoter virus vector is a replication and propagation competent virus. Double promoter vectors are described in U.S. Pat. No. 5,505,947 to Johnston et al., the disclosure of which is incorporated in its entirety by reference. Preferred alphaviruses for constructing the double promoter vectors are S.A.AR86, Girdwood S.A., TR339 and Ockelbo viruses. More preferably, the double promoter vector contains one or more attenuating mutations. Attenuating mutations are described in more detail hereinabove.

The double promoter vector is constructed so as to contain a second subgenomic promoter (i.e., 26S promoter) inserted 3' to the virus RNA encoding the structural proteins. The heterologous RNA is inserted between the second subgenomic promoter, so as to be operatively associated therewith, and the 3' UTR of the virus genome. Heterologous RNA sequences of less than 3 kilobases, more preferably those less than 2 kilobases, and more preferably still those less than 1 kilobase, can be inserted into the double promoter vector. In a preferred embodiment of the invention, the double promoter vector is derived from Girdwood S.A., and the second subgenomic promoter is a duplicate of the Girdwood S.A. subgenomic promoter. In an alternate preferred embodiment, the double promoter vector is derived from TR339, and the second subgenomic promoter is a duplicate of the TR339 subgenomic promoter.

B. Replicon Vectors.

Replicon vectors, which are propagation-defective virus vectors can also be used to carry out the present invention. Replicon vectors are described in more detail in copending U.S. application Ser. No. 08/448,630 to Johnston et al., the disclosure of which is incorporated in its entirety by reference. Preferred alphaviruses for constructing the replicon vectors are S.A.AR86, Girdwood S.A., TR339, and Ockelbo.

In general, in the replicon system, a foreign gene to be expressed is inserted in place of at least one of the viral structural protein genes in a transcription plasmid containing an otherwise full-length cDNA copy of the alphavirus genome RNA. RNA transcribed from this plasmid contains an intact copy of the viral nonstructural genes which are responsible for RNA replication and transcription. Thus, if the transcribed RNA is transfected into susceptible cells, it will be replicated and translated to give the nonstructural proteins. These proteins will transcribe the transfected RNA to give high levels of subgenomic mRNA, which will then be translated to produce high levels of the foreign protein. The autonomously replicating RNA (i.e., replicon) can only be packaged into virus particles if the alphavirus structural protein genes are provided on one or more "helper" RNAs, which are cotransfected into cells along with the replicon RNA. The helper RNAs do not contain the viral nonstructural genes for replication, but these functions are provided in trans by the replicon RNA. Similarly, the transcriptase functions translated from the replicon RNA transcribe the structural protein genes on the helper RNA, resulting in the synthesis of viral structural proteins and packaging of the replicon into virus-like particles. As the packaging or encapsidation signal for alphavirus RNAs is located within the nonstructural genes, the absence of these sequences in the helper RNAs precludes their incorporation into virus particles.

Alphavirus-permissive cells employed in the methods of the present invention are cells which, upon transfection with the viral RNA transcript, are capable of producing viral particles. Preferred alphavirus-permissive cells are TR339-permissive cells, Girdwood S.A.-permissive cells, S.A.AR86-permissive cells, and Ockelbo-permissive cells. Alphaviruses have a broad host range. Examples of suitable host cells include, but are not limited to Vero cells, baby hamster kidney (BHK) cells, and chicken embryo fibroblast cells.

The phrase "structural protein" as used herein refers to the encoded proteins which are required for encapsidation (e.g., packaging) of the RNA replicon, and include the capsid protein, E1 glycoprotein, and E2 glycoprotein. As described hereinabove, the structural proteins of the alphavirus are distributed among one or more helper RNAs (i.e., a first helper RNA and a second helper RNA). In addition, one or more structural proteins may be located on the same RNA molecule as the replicon RNA, provided that at least one structural protein is deleted from the replicon RNA such that the resulting alphavirus particle is propagation defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "propagation defective" as used herein, means that the replicon RNA cannot be encapsidated in the host cell in the absence of the helper RNA. The resulting alphavirus replicon particles are propagation defective inasmuch as the replicon RNA in these particles does not include all of the alphavirus structural proteins required for encapsidation, at least one of the required structural proteins being deleted therefrom, such that the replicon RNA initiates only an abortive infection; no new viral particles are produced, and there is no spread of the infection to other cells.

The helper cell for expressing the infectious, propagation defective alphavirus particle comprises a set of RNAs, as described above. The set of RNAs principally include a first helper RNA and a second helper RNA. The first helper RNA includes RNA encoding at least one alphavirus structural protein but does not encode all alphavirus structural proteins. In other words, the first helper RNA does not encode at least one alphavirus structural protein; the at least one non-coded alphavirus structural protein being deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third, preferred embodiment, the first helper RNA includes RNA encoding the alphavirus E1 glycoprotein and the alphavirus E2 glycoprotein, with the alphavirus capsid protein being deleted from the first helper RNA.

The second helper RNA includes RNA encoding at least one alphavirus structural protein which is different from the at least one structural protein encoded by the first helper RNA. Thus, the second helper RNA encodes at least one alphavirus structural protein which is not encoded by the first helper RNA. The second helper RNA does not encode the at least one alphavirus structural protein which is encoded by the first helper RNA, thus the first and second helper RNAs do not encode duplicate structural proteins. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein which is deleted from the first helper RNA.

In one embodiment, the packaging segment (RNA comprising the encapsidation or packaging signal) is deleted from at least the first helper RNA. In a preferred embodiment, the packaging segment is deleted from both the first helper RNA and the second helper RNA.

In the preferred embodiment wherein the packaging segment is deleted from both the first helper RNA and the second helper RNA, the helper cell is co-transfected with a replicon RNA in addition to the first helper RNA and the second helper RNA. The replicon RNA encodes the packaging segment and an inserted heterologous RNA. The inserted heterologous RNA may be RNA encoding a protein or a peptide. In a preferred embodiment, the replicon RNA, the first helper RNA and the second helper RNA are provided on separate molecules such that a first molecule, i.e., the replicon RNA, includes RNA encoding the packaging segment and the inserted heterologous RNA, a second molecule, i.e., the first helper RNA, includes RNA encoding at least one but not all of the required alphavirus structural proteins, and a third molecule, i.e., the second helper RNA, includes RNA encoding at least one but not all of the required alphavirus structural proteins. For example, in one preferred embodiment of the present invention, the helper cell includes a set of RNAs which include (a) a replicon RNA including RNA encoding an alphavirus packaging sequence and an inserted heterologous RNA, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble into alphavirus particles in the host cell.

In an alternate embodiment, the replicon RNA and the first helper RNA are on separate molecules, and the replicon RNA and RNA encoding a structural gene not encoded by the first helper RNA are on another single molecule together, such that a first molecule, i.e., the first helper RNA, including RNA encoding at least one but not all of the required alphavirus structural proteins, and a second molecule, i.e., the replicon RNA, including RNA encoding the packaging segment, the inserted heterologous RNA, and the remaining structural proteins not encoded by the first helper RNA. For example, in one preferred embodiment of the present invention, the helper cell includes a set of RNAs including (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell, with the replicon RNA packaged therein.

In one preferred embodiment of the present invention, the RNA encoding the alphavirus structural proteins, i.e., the capsid, E1 glycoprotein and E2 glycoprotein, contains at least one attenuating mutation, as described hereinabove. Thus, according to this embodiment, at least one of the first helper RNA and the second helper RNA includes at least one attenuating mutation. In a more preferred embodiment, at least one of the first helper RNA and the second helper RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Alternatively, when the replicon RNA and the RNA encoding the structural proteins not encoded by the first helper RNA are located on the same molecule, an attenuating mutation may be positioned in the RNA which codes for the structural protein not encoded by the first helper RNA. The attenuating mutations may also be located within the RNA encoding non-structural proteins (e.g., the replicon RNA).

Preferably, the first helper RNA and the second helper RNA also include a promoter. It is also preferred that the replicon RNA also includes a promoter. Suitable promoters for inclusion in the first helper RNA, second helper RNA and replicon RNA are well known in the art. One preferred promoter is the Girdwood S.A. 26S promoter for use when the alphavirus is Girdwood S.A. Another preferred promoter is the TR339 26S promoter for use when the alphavirus is TR339. Additional promoters beyond the Girdwood S.A. and TR339 promoters include the VEE 26S promoter, the Sindbis 26S promoter, the Semliki Forest 26S promoter, and any other promoter sequence recognized by alphavirus polymerases. Alphavirus promoter sequences containing mutations which alter the activity level of the promoter (in relation to the activity level of the wild-type) are also suitable in the practice of the present invention. Such mutant promoter sequences are described in Raju and Huang, *J. Virol.* 65, 2501–2510 (1991), the disclosure of which is incorporated herein in its entirety. In the system wherein the first helper RNA, the second helper RNA, and the replicon RNA are all on separate molecules, the promoters, if the same promoter is used for all three RNAs, provide a homologous sequence between the three molecules. It is preferred that the selected promoter is operative with the non-structural proteins encoded by the replicon RNA molecule.

In cases where vaccination with two immunogens provides improved protection against disease as compared to vaccination with only a single immunogen, a double-promoter replicon would ensure that both immunogens are produced in the same cell. Such a replicon would be the same as the one described above, except that it would contain two copies of the 26S RNA promoter, each followed by a different multiple cloning site, to allow for the insertion and expression of two different heterologous proteins. Another useful strategy is to insert the IRES sequence from the picornavirus, EMC virus, between the two heterologous genes downstream from the single 26S promoter of the replicon described above, thus leading to expression of two immunogens from the single replicon transcript in the same cell.

C. Uses of the Present Invention.

The alphavirus vectors, RNAs, cDNAs, helper cells, infectious virus particles, and methods of the present invention find use in in vitro expression systems, wherein the inserted heterologous RNA encodes a protein or peptide which is desirably produced in vitro. The RNAs, cDNAs, helper cells, infectious virus particles, methods, and pharmaceutical formulations of the present invention are additionally useful in a method of administering a protein or peptide to a subject in need of the protein or peptide, as a method of treatment or otherwise. In this embodiment of the invention, the heterologous RNA encodes the desired protein or peptide, and pharmaceutical formulations of the present invention are administered to a subject in need of the desired protein or peptide. In this manner, the protein or peptide may thus be produced in vivo in the subject. The subject may be in need of the protein or peptide because the subject has a deficiency thereof, or because the production of the protein or peptide in the subject may impart some therapeutic effect, as a method of treatment or otherwise.

Alternately, the claimed methods provide a vaccination strategy, wherein the heterologous RNA encodes an immunogenic protein or peptide.

The methods and products of the invention are also useful as antigens and for evoking the production of antibodies in animals such as horses and rabbits, from which the antibodies may be collected and then used in diagnostic assays in accordance with known techniques.

A further aspect of the present invention is a method of introducing and expressing antisense oligonucleotides in bone marrow cell cultures to regulate gene expression. Alternately, the claimed method finds use in introducing and expressing a protein or peptide in bone marrow cell cultures.

II. Girdwood S.A. and TR339 Clones

Disclosed hereinbelow are genomic RNA sequences encoding live Girdwood S.A. virus, live S.A.AR86 virus, and live Sindbis strain TR339 virus, cDNAs derived therefrom, infectious RNA transcripts encoded by the cDNAs, infectious viral particles containing the infectious RNA transcripts, and pharmaceutical formulations derived therefrom.

The cDNA sequence of Girdwood S.A. is given herein as SEQ ID NO:4. Alternatively, the cDNA may have a sequence which differs from the cDNA of SEQ ID NO:4, but which has the same protein sequence as the cDNA given herein as SEQ ID NO:4. Thus, the cDNA may include one or more silent mutations.

The phrase "silent mutation" as used herein refers to mutations in the cDNA coding sequence which do not produce mutations in the corresponding protein sequence translated therefrom.

Likewise, the cDNA sequence of TR339 is given herein as SEQ ID NO:8. Alternatively, the cDNA may have a sequence which differs from the cDNA of SEQ ID NO:8, but which has the same protein sequence as the cDNA given herein as SEQ ID NO:8. Thus, the cDNA may include one or more silent mutations.

The cDNAs encoding infectious Girdwood S.A. and TR339 virus RNA transcripts of the present invention include those homologous to, and having essentially the same biological properties as, the cDNA sequences disclosed herein as SEQ ID NO:4 and SEQ ID NO:8, respectively. Thus, cDNAs that hybridize to cDNAs encoding infectious Girdwood S.A. or TR339 virus RNA transcripts disclosed herein are also an aspect of this invention. Conditions which will permit other cDNAs encoding infectious Girdwood S.A. or TR339 virus transcripts to hybridize to the cDNAs disclosed herein can be determined in accordance with known techniques. For example, hybridization of such sequences may be carried out under conditions of reduced stringency, medium stringency, or even high stringency conditions (e.g., conditions represented by a wash stringency of 35–40% formamide with 5× Denhardt's solution, 0.5% SDS and 1× SSPE at 37° C.; conditions represented by a wash stringency of 40–45% formamide with 5× Denhardt's solution, 0.5% SDS, and 1× SSPE at 42° C.; and conditions represented by a wash stringency of 50% formamide with 5× Denhardt's solution, 0.5% SDS and 1× SSPE at 42° C., respectively, to cDNA encoding infectious Girdwood S.A. or TR339 virus RNA transcripts disclosed herein in a standard hybridization assay. See J. SAMBROOK ET AL., *MOLECULAR CLONING: A LABORATORY MANUAL* (2d ed. 1989)). In general, cDNA sequences encoding infectious Girdwood S.A. or TR339 virus RNA transcripts that hybridize to the cDNAs disclosed herein will be at least 30% homologous, 50% homologous, 75% homologous, and even 95% homologous or more with the cDNA sequences encoding infectious Girdwood S.A. or TR339 virus RNA transcripts disclosed herein.

Promoter sequences and Girdwood S.A. virus or Sindbis virus strain TR339 cDNA clones are operatively associated in the present invention such that the promoter causes the cDNA clone to be transcribed in the presence of an RNA polymerase which binds to the promoter. The promoter is positioned on the 5' end (with respect to the virion RNA sequence), of the cDNA clone. An excessive number of nucleotides between the promoter sequence and the cDNA clone will result in the inoperability of the construct. Hence, the number of nucleotides between the promoter sequence and the cDNA clone is preferably not more than eight, more preferably not more than five, still more preferably not more than three, and most preferably not more than one.

Examples of promoters which are useful in the cDNA sequences of the present invention include, but are not limited to T3 promoters, T7 promoters, cytomegalovirus (CMV) promoters, and SP6 promoters. The DNA sequence of the present invention may reside in any suitable transcription vector. The DNA sequence preferably has a complementary DNA sequence bound thereto so that the double-stranded sequence will serve as an active template for RNA polymerase. The transcription vector preferably comprises a plasmid. When the DNA sequence comprises a plasmid, it is preferred that a unique restriction site be provided 3' (with respect to the virion RNA sequence) to the cDNA clone. This provides a means for linearizing the DNA sequence to allow the transcription of genome-length RNA in vitro.

The cDNA clones can be generated by any of a variety of suitable methods known to those skilled in the art. A preferred method is the method set forth in U.S. Pat. No. 5,185,440 to Davis et al., the disclosure of which is incorporated in its entirety by reference, and Gubler et al., Gene 25:263 (1983).

RNA is preferably synthesized from the DNA sequence in vitro using purified RNA polymerase in the presence of ribonucleotide triphosphates and cap analogs in accordance with conventional techniques. However, the RNA may also be synthesized intracellularly after introduction of the cDNA.

The Girdwood S.A. and TR339 cDNA clones and the infectious RNAs and infectious virus particles produced therefrom of the present invention are useful for the preparation of pharmaceutical formulations, such as vaccines. In addition, the cDNA clones, infectious RNAs, and infectious viral particles of the present invention are useful for administration to animals for the purpose of producing antibodies to the Girdwood S.A. virus or the Sindbis virus strain TR339, which antibodies may be collected and used in known diagnostic techniques for the detection of Girdwood S.A. virus or Sindbis virus strain TR339. Antibodies can also be generated to the viral proteins expressed from the cDNAs disclosed herein. As another aspect of the present invention, the claimed cDNA clones are useful as nucleotide probes to detect the presence of Girdwood S.A. or TR339 genomic RNA or transcripts.

III. Infectious Virus Particles and Pharmaceutical Formulations

The infectious virus particles of the present invention include those containing double promoter vectors and those containing replicon vectors as described hereinabove. Alternately, the infectious virus particles contain infectious RNAs encoding the Girdwood S.A. or TR339 genome. When the infectious RNA comprises the Girdwood S.A. genome, preferably the RNA has the sequence encoded by the cDNA given as SEQ ID NO:4. When the infectious RNA comprises the TR339 genome, preferably the RNA has the sequence encoded by the cDNA given as SEQ ID NO:8.

The infectious, alphavirus particles of the present invention may be prepared according to the methods disclosed herein in combination with techniques known to those skilled in the art. These methods include transfecting an alphavirus-permissive cell with a replicon RNA including the alphavirus packaging segment and an inserted heterologous RNA, a first helper RNA including RNA encoding at least one alphavirus structural protein, and a second helper RNA including RNA encoding at least one alphavirus structural protein which is different from that encoded by the first helper RNA. Alternately, and preferably, at least one of the helper RNAs is produced from a cDNA encoding the helper RNA and operably associated with an appropriate promoter, the cDNA being stably transfected and integrated into the cells. More preferably, all of the helper RNAs will be "launched" from stably transfected cDNAs. The step of transfecting the alphavirus-permissive cell can be carried out according to any suitable means known to those skilled in the art, as described above with respect to propagation-competent viruses.

Uptake of propagation-competent RNA into the cells in vitro can be carried out according to any suitable means known to those skilled in the art. Uptake of RNA into the cells can be achieved, for example, by treating the cells with DEAE-dextran, treating the RNA with LIPOFECTIN® before addition to the cells, or by electroporation, with electroporation being the currently preferred means. These techniques are well known in the art. See e.g., U.S. Pat. No. 5,185,440 to Davis et al., and PCT Publication No. WO 92/10578 to Bioption AB, the disclosures of which are incorporated herein by reference in their entirety. Uptake of propagation-competent RNA into the cell in vivo can be carried out by administering the infectious RNA to a subject as described in Section I above.

The infectious RNAs may also contain a heterologous RNA segment, where the heterologous RNA segment contains a heterologous RNA and a promoter operably associated therewith. It is preferred that the infectious RNA introduces and expresses the heterologous RNA in bone marrow cells as described in Section I above. According to this embodiment, it is preferable that the promoter operatively associated with the heterologous RNA is operable in bone marrow cells. The heterologous RNA may encode any protein or peptide, preferably an immunogenic protein or peptide, a therapeutic protein or peptide, a hormone, a growth factor, an interleukin, a cytokine, a chemokine, an enzyme, a ribozyme, or an antisense oligonucleotide as described in more detail in Section I above.

The step of facilitating the production of the infectious viral particles in the cells may be carried out using conventional techniques. See e.g., U.S. Pat. No. 5,185,440 to Davis et al., PCT Publication No. WO 92/10578 to Bioption AB, and U.S. Pat. No. 4,650,764 to Temin et al. (although Temin et al., relates to retroviruses rather than alphaviruses). The infectious viral particles may be produced by standard cell culture growth techniques.

The step of collecting the infectious virus particles may also be carried out using conventional techniques. For example, the infectious particles may be collected by cell lysis, or collection of the supernatant of the cell culture, as is known in the art. See e.g., U.S. Pat. No. 5,185,440 to Davis et al., PCT Publication No. WO 92/10578 to Bioption AB, and U.S. Pat. No. 4,650,764 to Temin et al. Other suitable techniques will be known to those skilled in the art. Optionally, the collected infectious virus particles may be purified if desired. Suitable purification techniques are well known to those skilled in the art.

Pharmaceutical formulations, such as vaccines, of the present invention comprise an immunogenic amount of the infectious, virus particles in combination with a pharmaceutically acceptable carrier. An "immunogenic amount" is an amount of the infectious virus particles which is sufficient to evoke an immune response in the subject to which the pharmaceutical formulation is administered. An amount of from about $10^3$ to about $10^7$ particles, and preferably about $10^4$ to $10^6$ particles per dose is believed suitable, depending upon the age and species of the subject being treated, and the immunogen against which the immune response is desired.

Pharmaceutical formulations of the present invention for therapeutic use comprise a therapeutic amount of the infectious virus particles in combination with a pharmaceutically acceptable carrier. A "therapeutic amount" is an amount of the infectious virus particles which is sufficient to produce a therapeutic effect (e.g., triggering an immune response or supplying a protein to a subject in need thereof) in the subject to which the pharmaceutical formulation is administered. The therapeutic amount will depend upon the age and species of the subject being treated, and the therapeutic protein or peptide being administered. Typical dosages are an amount from about $10^1$ to about $10^5$ infectious units.

Exemplary pharmaceutically acceptable carriers include, but are not limited to, sterile pyrogen-free water and sterile pyrogen-free physiological saline solution. Subjects which may be administered immunogenic amounts of the infectious virus particles of the present invention include but are not limited to human and animal (e.g., pig, cattle, dog, horse, donkey, mouse, hamster, monkeys) subjects.

Pharmaceutical formulations of the present invention include those suitable for parenteral (e.g., subcutaneous, intracerebral, intradermal, intramuscular, intravenous and intraarticular) administration. Alternatively, pharmaceutical formulations of the present invention may be suitable for administration to the mucus membranes of a subject (e.g., intranasal administration by use of a dropper, swab, or inhaler). The formulations may be conveniently prepared in unit dosage form and may be prepared by any of the methods well known in the art.

The following examples are provided to illustrate the present invention, and should not be construed as limiting thereof. In these examples, PBS means phosphate buffered saline, EDTA means ethylene diamine tetraacetate, ml means milliliter, μl means microliter, mM means millimolar, μM means micromolar, u means unit, PFU means plaque forming units, g means gram, mg means milligram, μg means microgram, cpm means counts per minute, ic means intracerebral or intracerebrally, ip means intraperitoneal or intraperitoneally, iv means intravenous or intravenously, and sc means subcutaneous or subcutaneously.

Amino acid sequences disclosed herein are presented in the amino to carboxyl direction, from left to right. The amino and carboxyl groups are not presented in the sequence. Nucleotide sequences are presented herein by single strand only in the 5' to 3' direction, from left to right. Nucleotides and amino acids are represented herein in the manner recommended by the IUPAC-IUB Biochemical Nomenclature Commission, or (for amino acids) by either one letter or three letter code, in accordance with 37 CFR §1.822 and established usage. Where one letter amino acid code is used, the same sequence is also presented elsewhere in three letter code.

EXAMPLE I

Cells and Virus Stocks

S.A.AR86 was isolated in 1954 from a pool of Culex sp. mosquitoes collected near Johannesburg, South Africa. Weinbren et al., *S. Afr. Med. J.* 30, 631–36 (1956). Ockelbo82 was isolated from Culiseta sp. mosquitoes collected in Edsbyn, Sweden in 1982 and was associated serologically with human disease. Nikldasson et al., *Am. J. Trop. Med. Hyg.* 33, 1212–17 (1984). Girdwood S.A. was isolated from a human patient in the Johannesburg area of South Africa in 1963. Malherbe et al., *S. Afr. Med. J.* 37, 547–52 (1963). Molecularly cloned virus TR339 represents the deduced consensus sequence of Sindbis AR339. McKnight et al., *J. Virol.* 70, 1981–89 (1996); William Klimstra, personal communication. TRSB is a laboratory strain of Sindbis isolate AR339 derived from a cDNA clone pTRSB and differing from the AR339 consensus sequence at three codons. McKnight et al., *J. Virol.* 70, 1981–89 (1996). pTR5000 is a full-length cDNA clone of Sindbis AR339 following the SP6 phage promoter and containing mostly Sindbis AR339 sequences.

Stocks of all molecularly cloned viruses were prepared by electroporating genome length in vitro transcripts of their respective cDNA clones in BHK-21 cells. Heidner et al., *J. Virol.* 68, 2683–92 (1994). Girdwood S.A. (Malherbe et al., *S. Afr. Med. J.* 37, 547–52 (1963)) and Ockelbo82 (Espmark and Niklasson, *Am. J. Trop. Med. Hyg.* 33, 1203–11 (1984); Niklasson et al., *Am. J. Trop. Med. Hyg.* 33, 1212–17 (1984)) were passed one to three times in BHK-21 cells in order to produce amplified stocks of virus. All virus stocks were stored at –70° C. until needed. The titers of the virus stocks were determined on BHK-21 cells from aliquots of frozen virus.

EXAMPLE 2

Cloning the S.A.AR86 and Girdwood S.A. Genomic Sequences

The sequences of S.A.AR86 (SEQ ID NO: 1) and Girdwood S.A. (SEQ ID NO:4) were determined from uncloned reverse transcriptase-polymerase chain reaction (RT-PCR) fragments amplified from virion RNA. Heidner et al., *J. Virol.* 68, 2683–92 (1994). The sequence of the 5' 40 nucleotides was determined by directly sequencing the genomic RNA. Sanger et al., *Proc. Natl. Acad. Sci. USA* 74, 5463–67 (1977); Zimmern and Kaesberg, *Proc. Natl. Acad. Sci. USA* 75, 4257–61 (1978); Ahlquist et al., *Cell* 23, 183–89 (1981).

The S.A.AR86 genome was 11,663 nucleotides in length, excluding the 5' CAP and 3' poly(A) tail, 40 nucleotides shorter than the alphavirus prototype Sindbis strain AR339. Strauss et al., *Virology* 133, 92–110 (1984). Compared with the consensus sequence of Sindbis virus AR339 (McKnight et al., *J. Virol.* 70 1981–89 (1996)), S.A.AR86 contained two separate 6-nucleotide insertions, and one 3-nucleotide insertion in the 3' half of the nsP3 gene, a region not well conserved among alphaviruses. The two 6-nucleotide insertions were found immediately 3' of nucleotides 5403 and 5450, and the 3-nucleotide insertion was immediately 3' of nucleotide 5546 compared with the AR339 genome. In addition, S.A.AR86 contained a 54-nucleotide deletion in nsP3 which spanned nucleotides 5256 to 5311 of AR339. As a result of these deletions and insertions, S.A.AR86 nsP3 was 13 amino acids smaller than AR339, containing an 18-amino acid deletion and a total of 5 amino acids. inserted. The 3' untranslated region of S.A.AR86 contained, with respect to AR339, two 1-nucleotide deletions at nucleotides 11,513 and 11,602, and one 1-nucleotide insertion following nucleotide 11,664. The total numbers of nucleotides and predicted amino acids comprising the remaining genes of S.A.AR86 were identical to those of AR339.

The cDNA sequence of S.A.AR86 is presented in SEQ ID NO:1. Nucleotides 1 through 59 represent the 5' UTR, the non-structural polyprotein is encoded by nucleotides 60 through 7559 (nsP1--nt60 through nt1679; nsP2--nt1680 through nt4099; nsP3--nt4100 through nt5729; nsP4--nt5730 through nt7559), the structural polyprotein is encoded by nucleotides 7608 through 11342 (capsid--nt7608 through nt8399; E3--nt8400 through nt8591; E2--nt8592 through nt9860; 6K--nt9861 through nt10025; E1--nt10026 through nt11342), and the 3' UTR is represented by nucleotides 11346 through 11663.

A notable feature of the deduced amino acid sequence of S.A.AR86 (SEQ ID NO:2 and SEQ ID NO:3) was the cysteine codon in place of an opal termination codon between nsP3 and nsP4. S.A.AR86 is the only alphavirus of the Sindbis group, and one of just three alphavirus isolates sequenced to date, which do not contain an opal termination codon between nsP3 and nsP4. Takkinen, K., *Nucleic Acids Res.* 14, 5667–5682 (1986); Strauss et al., *Virology* 164, 265–74 (1988).

The genome of Girdwood S.A. was 11,717 nucleotides long excluding the 5' CAP and 3' poly(A) tail. The nucleotide sequence (SEQ ID NO:4) of the Girdwood S.A. genome and the putative amino acid sequence (SEQ ID NO:5 and SEQ ID NO:6) of the Girdwood S.A. gene products are shown in the accompanying sequence listings. Position 1902 in SEQ ID NO:5 indicates the position of the opal termination codon in the coding region of the nonstructural polyprotein. The extra nucleotides relative to AR339 were in the nonconserved half of nsP3, which contained insertions totalling 15 nucleotides, and in the 3' untranslated region which contained two 1-nucleotide deletions and a 1-nucleotide insertion with respect to the consensus Sindbis AR339 genome. The insertions found in the nsP3 gene of Girdwood S.A. were identical in position and content to those found in S.A.AR86, although Girdwood S.A. did not have the large nsP3 deletion characteristic of S.A.AR86. The remaining portions of the genome contained the same number of nucleotides and predicted amino acids as Sindbis AR339.

The cDNA sequence of Girdwood S.A. is presented in SEQ ID NO:4. An "N" in the sequence indicates that the identity of the nucleotide at that position is unknown. Nucleotides 1 through 59 represent the 5' UTR, the nonstructural polyprotein is encoded by nucleotides 60 through 7613 (nsP1--nt60 through nt1679; nsP2--nt1680 through nt4099; nsP3--nt4100 through nt5762 or nt5783; nsP4--nt5784 through nt7613), the structural polyprotein is encoded by nucleotides 7662 through 11396 (capsid--nt7662 through nt8453; E3--nt8454 through nt8645; E2--nt8646 through nt9914; 6K--9915 through nt10079; E1--nt10080 through nt11396), and the 3' UTR is represented by nucleotides 11400 through 11717. There is an opal termination codon at nucleotides 5763 through 5765.

Overall, Girdwood S.A. was 94.5% identical to the consensus Sindbis AR339 sequence, differing at 655 nucleotides not including the insertions and deletions. These nucleotide differences resulted in 88 predicted amino acid changes or a difference of 2.3%. A plurality of amino acid differences were concentrated in the nsP3 gene, which contained 32 of the amino acid changes, 25 of which were in the nonconserved 3' half.

The Girdwood S.A. nucleotides at positions 1, 3, and 11,717 could not be resolved. Because the primer used during the RT-PCR amplification of the 3' end of the genome assumed a cytosine in the 3' terminal position, the identity of this nucleotide could not be determined with certainty. However, in all alphaviruses sequenced to date there is a cytosine in this position. This, combined with the fact that no difficulty was encountered in obtaining RT-PCR product for this region with an oligo(dT) primer ending with a 3' G, suggested that Girdwood S.A. also contains a cytosine at this position. The ambiguity at nucleotide positions 1 and 3 resulted from strong stops encountered during the RNA sequencing.

EXAMPLE 3

Comparison of S.A.AR86 and Girdwood S.A. Sequences With Other Sindbis-Related Virus Sequences Table 1 examines the relationship of S.A.AR86 and Girdwood S.A. to each other and to other Sindbis-related viruses. This was accomplished by aligning the nucleotide and deduced amino acid sequences of Ockelbo82, AR339 and Girdwood S.A. to those of S.A.AR86 and then calculating the percentage identity for each gene using the programs contained within the Wisconsin-GCG package (Genetics Computer Group, 575 Science Drive, Madison, Wis. 53711); as described in more detail in McKnight et al., *J. Virol.* 70, 1981–89 (1996).

The analysis suggests that S.A.AR86 is most similar to the other South African isolate, Girdwood S.A., and that the South African isolates are more similar to the Swedish Ockelbo82 isolate than to the Egyptian Sindbis AR339 isolate. These results also suggest that it is unlikely that S.A.AR86 is a recombinant virus like WEE virus. Hahn et al., *Proc. Natl. Acad. Sci. USA* 85, 5997–6001 (1988).

TABLE 1

Comparison of the Nucleotide and Amino Acid Sequences of S.A.AR86 Virus with Those of Sindbis AR339, Ockelbo82, and Girdwood S.A. Viruses[a]

| Regions | Nucleotide Differences[b] | | | Amino Acid Differences[b] | | |
|---|---|---|---|---|---|---|
| | AR339 Number (%) | OCK82 Number (%) | GIRD | AR339 Number (%) | OCK82 Number (%) | GIRD |
| 5' untranslated | 0 (0.0) | 0 (0.0) | 1 (1.7) | — | — | — |
| nsP1 | 76 (4.7) | 37 (2.3) | 15 (0.9) | 9 (1.7) | 6 (1.1) | 2 (0.4) |
| nsP2 | 137 (5.7) | 86 (3.6) | 45 (1.9) | 15 (1.9) | 8 (1.0) | 12 (1.5) |
| nsP3 | | | | | | |
| Conserved[c] | 51 (5.7) | 35 (3.9) | 13 (1.6) | 6 (2.0) | 1 (0.3) | 1 (0.4) |
| Nonconserved[d] | 116 (6.6) | 83 (4.4) | 70 (2.2) | 45 (9.7) | 34 (7.0) | 27 (3.7) |
| nsP4 | 111 (6.1) | 68 (3.7) | 19 (1.1) | 8 (1.3) | 2 (0.3) | 4 (0.6) |
| 26s junction | 1 (2.1) | 0 (0.0) | 1 (2.1) | — | — | — |
| Capsid | 36 (4.5) | 26 (3.3) | 7 (0.9) | 1 (0.4) | 3 (1.1) | 0 (0.0) |
| E3 | 17 (8.9) | 5 (2.6) | 4 (2.1) | 1 (1.6) | 0 (0.0) | 0 (0.0) |
| E2 | 71 (5.6) | 43 (3.4) | 18 (1.4) | 12 (2.6) | 6 (1.4) | 2 (0.5) |
| 6K | 10 (6.1) | 9 (5.4) | 4 (2.4) | 2 (3.6) | 2 (3.6) | 1 (1.8) |
| E1 | 49 (3.7) | 31 (2.3) | 16 (1.2) | 7 (1.6) | 6 (1.4) | 2 (0.9) |
| 3' untranslated | 14 (4.5) | 8 (2.5) | 1 (0.3) | — | — | — |
| Totals | 689 (5.5) | 431 (3.3) | 214 (1.4) | 106 (2.3) | 68 (1.4) | 51 (0.9) |

[a]All nucleotide positions and gene boundaries are numbered according to those used for the Sindbis AR339, HR$_{sp}$ variant Genebank Accession No. J02363; Strauss et al., Virology 133, 92–110 (1984).
[b]Differences include insertions and deletions.
[c]Conserved region nucleotides 4100 to 5000 (aa 1 to aa300).
[d]Nonconserved region nucleotides 5001 to 5729 (aa301 to aa5421 S.A.AR86 numbering).

EXAMPLE 4

Neurovirulence of S.A.AR86 and Girdwood S.A.

Girdwood S.A., Ockelbo82, and S.A.AR86 are related by sequence; in contrast, it has previously been reported that only S.A.AR86 displayed the adult mouse neurovirulence phenotype. Russell et al., *J. Virol.* 63, 1619–29 (1989). These findings were confirmed by the present investigations. Briefly, groups of four female CD-1 mice (3–6 weeks of age) were inoculated ic with $10^3$ plaque-forming units (PFU) of S.A.AR86, Girdwood S.A., or Ockelbo82. Neither Girdwood S.A. nor Ockelbo82 infection produced any clinical signs of infection. Infection with S.A.AR86 produced neurological signs within four to five days and ultimately killed 100% of the mice as previously demonstrated.

Table 2 lists those amino acids of S.A.AR86 which might explain the neurovirulence phenotype in adult mice. A position was scored as potentially related to the S.A.AR86 adult neurovirulence phenotype if the S.A.AR86 amino acid differed from that which otherwise was absolutely conserved at that position in the other viruses.

TABLE 2

Divergent Amino Acids in S.A.AR86 Potentially Related to the Adult Neurovirulence Phenotype

| | Position in S.A.AR86 | S.A.AR86 Amino Acid | Conserved Amino Acid |
|---|---|---|---|
| nsP1 | 583 | Thr | Ile |
| nsP2 | 256 | Arg | Ala |
| | 648 | Ile | Val |
| | 651 | Lys | Glu |
| nsP3 | 344 | Gly | Glu |
| | 386 | Tyr | Ser |
| | 441 | Asp | Gly |
| | 445 | Ile | Met |
| | 537 | Cys | Opal |
| E2 | 243 | Ser | Leu |
| 6K | 30 | Val | Ile |
| E1 | 112 | Val | Ala |
| | 169 | Leu | Ser |

EXAMPLE 5 pS55 Molecular Clone of S.A.AR86

As a first step in investigating the unique adult mouse neurovirulence phenotype of S.A.AR86, a full-length cDNA clone of the S.A.AR86 genome was constructed. The sources of cDNA included conventional cDNA clones (Davis et al., *Virology* 171, 189–204 (1989)) as well as uncloned RT-PCR fragments derived from the S.A.AR86 genome. As described previously, these were substituted, starting at the 3' end, into pTR5000 (McKnight et al., *J. Virol.* 70, 1981–89 (1996)), a full-length Sindbis clone from which infectious genomic replicas could be derived by transcription with SP6 polymerase in vitro.

The end result was pS55, a molecular clone of S.A.AR86 from which infectious transcripts could be produced and which contained four nucleotide changes (G for A at nt 215; G for C at nt 3863; G for A at nt 5984; and C for T at nt 9113) but no amino acid coding differences with respect to the S.A.AR86 genomic RNA (amino acid sequence of S.A.AR86 presented in SEQ ID NO:2 and SEQ ID NO:3. The nucleotide sequence of clone pS55 is presented in SEQ ID NO:7.

As has been described by Simpson et al., *Virology* 222, 464–69 (1996), neurovirulence and replication of the virus derived from pS55 (S55) were compared with those of S.A.AR86. It was found that S55 exhibits the distinctive adult neurovirulence characteristic of S.A.AR86. Like S.A.AR86, S55 produces 100% mortality in adult mice infected with the virus and the survival times of animals infected with both viruses were indistinguishable. In addition, S55 and S.A.AR86 were found to replicate to essentially equivalent titers in vivo, and the profiles of S55 and S.A.AR86 virus growth in the central nervous system and periphery were very similar.

From these data it was concluded that the silent changes found in virus derived from clone pS55 had little or no effect on its growth or virulence, and that this molecularly cloned virus accurately represents the biological isolate, S.A.AR86.

EXAMPLE 6

Construction of the Consensus AR339 Virus TR339

The consensus sequence of the Sindbis virus AR339 isolate, the prototype alphavirus was deduced. The consensus AR339 sequence was inferred by comparison of the TRSB sequence (a laboratory-derived AR339 strain) with the complete or partial sequences of $HR_{sp}$ (the Gen Bank sequence; Strauss et al., *Virology* 133, 92–110 (1984)), SV1A, and NSV (AR339-derived laboratory strains; Lustig et al., *J. Virol* 62, 2329–36 (1988)), and SIN (a laboratory-derived AR339 strain; Davis et al., *Virology* 161, 101–108 (1987), Strauss et al., *J. Virol.* 65, 4654–64 (1991)). Each of these viruses was descended from AR339. Where these sequences differed from each other, they also were compared with the amino acid sequences of other viruses related to Sindbis virus: Ockelbo82, S.A.AR86, Girdwood S.A., and the somewhat more distantly related Aura virus. Rumenapf et al., Virology 208, 621–33 (1995).

The details of determining a consensus AR339 sequence and constructing the consensus virus TR339 have been described elsewhere. McKnight et al., *J. Virol.* 70, 1981–89 (1996); Klimstra et al., manuscript in preparation. The nucleotide sequence of pTR339 is presented SEQ ID NO:8. The deduced amino acid sequences of the pTR339 non-structural and structural polyproteins are shown as SEQ ID NO:9 and SEQ ID NO:10, respectively. Referring to SEQ ID NO:8, nucleotides 1 through 59 represent the 5' UTR, the non-structural polyprotein is encoded by nucleotides 60 through 7598 (nsP1--nt60 through nt1679; nsP2--nt1680 through nt4099; nsP3--nt4100 through nt5747 or 5768; nsP4--nt5769 through nt7598), the structural polyprotein is encoded by nucleotides 7647 through 11381 (capsid--nt7647 through nt8438; E3--nt8439 through nt8630; E2--nt8631 through nt9899; 6K--nt9900 through nt10064; E1--nt10065 through nt11381), and the 3' UTR is represented by nucleotides 11382 through 11703. There is an opal termination codon at nucleotides 5748 through 5750. Position 1897 in SEQ ID NO:9 indicates the position of the opal termination codon in the coding region of the nonstructural polyprotein. The consensus nucleotide sequence diverged from the pTRSB sequence at three coding positions (nsP3 528, E2 1, and E1 72). These differences are illustrated in Table 3.

TABLE 3

Amino Acid Differences Between Laboratory Strain TRSB and Molecular Clone TR339

| | nsP3 528 (nt5683) | E2 1 (nt8633) | E1 72 (nt10279) |
|---|---|---|---|
| TR339 | Arg (CGA) | Ser (AGC) | Ala (GCU) |
| TRSB | Gln (CAA) | Arg (AGA) | Val (GUU) |

EXAMPLE 7

Animals Used for In Vivo Localization Studies

Specific pathogen free CD-1 mice were obtained from Charles River Breeding Laboratories (Raleigh, N.C.) at 21 days of age and maintained under barrier conditions until approximately 37 days of age. Intracerebral (ic) inoculations were performed as previously described, Simpson et al., Virol. 222, 464–49 (1996), with 500 PFU of S51 (an attenuated mutant of S55) or $10^3$ PFU of S55. Animals inoculated peripherally were first anesthetized with METO-FANE®. Then, 25 µl of diluent (PBS, pH 7.2, 1% donor calf serum, 100 u/ml penicillin, 50 µg/ml streptomycin, 0.9 mM $CaCl_2$, and 0.5 mM $MgCl_2$) containing $10^3$ PFU of virus were injected either intravenously (iv) into the tail vein, subcutaneously (sc) into the skin above the shoulder blades on the middle of the back, or intraperitoneally (ip) in the lower right abdomen. Animals were sacrificed at various times post-inoculation as previously described. Simpson et al., Virol. 222, 464–49 (1996). Brains (including brainstems) were homogenized in diluent to 30% w/v, and right quadriceps were homogenized in diluent to 25% w/v. Homogenates were handled and titered as described previously. Simpson et al., Virol. 222, 464–49 (1996). Bone marrow was harvested by crushing both femurs from each animal in sufficient diluent to produce a 30% w/v suspension (calculated as weight of uncrushed femurs in volume of diluent). Samples were stored at −70° C. For titration, samples were thawed and clarified by centrifugation at 1,000 x g for 20 minutes at 4° C. before being titered by conventional plaque assay on BHK-21 cells.

EXAMPLE 8

Tissue Preparation for In Situ Hybridization Studies

Animals were anesthetized by ip injection of 0.5 ml AVERTIN® at various times post-inoculation followed by perfusion with 60 to 75 ml of 4% paraformaldehyde in PBS (pH 7.2) at a flow rate of 10 ml per minute. The entire carcass was decalcified for 8 to 10 weeks in 4% parafomaldehyde containing 8% EDTA in PBS (pH 6.8) at 4° C. This solution was changed twice during the decalcification period. Selected tissues were cut into blocks approximately 3 mm thick and placed into biopsy cassettes for paraffin embedding and sectioning. Blocks were embedded, sectioned and hematoxylin/eosin stained by Experimental Pathology Laboratories (Research Triangle Park, N.C.) or North Carolina State University Veterinary School Pathology Laboratory (Raleigh, N.C.).

EXAMPLE 9

In Situ Hybridization

Hybridizations were performed using a [$^{35}$S]-UTP labeled S.A.AR86 specific riboprobe derived from pDS-45. Clone pDS-45 was constructed by first amplifying a 707 base pair fragment from pS55 by PCR using primers 7241 (5'-CTGCGGCGGATTCATCTTGC-3', SEQ ID NO:11) and SC-3 (5'-CTCCAACTTAAGTG-3', SEQ ID NO:12). The resulting 707 base pair fragment was purified using a GENE CLEAN® kit (Bio101, Calif.), digested with HhaI, and cloned into the SmaI site of pSP72 (Promega). Linearizing pDS-45 with EcoRV and performing an in vitro transcription reaction with SP6 DNA-dependent, RNA polymerase (Promega) in the presence of [$^{35}$S]-UTP resulted in a riboprobe approximately 500 nucleotides in length of which 445 nucleotides were complementary to the S.A.AR86 genome (nucleotides 7371 through 7816). A riboprobe specific for the influenza strain PR-8 hemagglutinin (HA) gene was used as a control probe to test non-specific binding. The in situ hybridizations were performed as described previously (Charles et al., Virol. 208, 662–71 (1995)) using $10^5$ cpm of probe per slide.

EXAMPLE 10

Replication of S.A.AR86 in Bone Marrow

Three groups of six adult mice each were inoculated peripherally (sc, ip, or iv) with 1200 PFU of S55 (a molecular clone of S.A.AR86) in 25 $\mu$l of diluent. Under these conditions, the infection produced no morbidity or mortality. Two mice from each group were anesthetized and sacrificed at 2, 4 and 6 days post-inoculation by exsanguination. The serum, brain (including brainstem), right quadricep, and both femurs were harvested and titered by plaque assay. Virus was never detected in the quadricep samples of animals inoculated sc (Table 4). A single animal inoculated ip (two days post-inoculation) and two mice inoculated iv (at four and six days post-inoculation) had detectable virus in the right quadricep, but the titer was at or just above the limit of detection (6.25 PFU/g tissue). Virus was present sporadically or at low levels in the brain and serum of animals regardless of the route of inoculation. Virus was detected in the bone marrow of animals regardless of the route of inoculation. However, the presence of virus in bone marrow of animals inoculated sc or ip was more sporadic than animals inoculated iv, where five out of six animals had detectable virus. These results suggest that S55 targets to the bone marrow, especially following iv inoculation.

The level and frequency of virus detected in the serum and muscle suggested that virus detected in the bone marrow was not residual virus contamination from blood or connective tissue remaining in bone marrow samples. The following experiment also suggested that virus in bone marrow was not due to tissue or serum contamination. Mice were inoculated ic with 1200 PFU of S55 in 25 $\mu$l of diluent. Animals were sacrificed at 0.25, 0.5, 1, 1.5, 2, 3, 4, 5, and 6 days post-inoculation, and the carcasses were decalcified as described in Example 8. Coronal sections taken at approximately 3 mm intervals through the head, spine (including shoulder area), and hips were probed with an S55-specific [$^{35}$S]-UTP labeled riboprobe derived from pDS-45. Positive in situ hybridization signal was detected by one day post-inoculation in the bone marrow of the skull (data not shown). Weak signal also was present in some of the chondrocytes of the vertebrae, suggesting that S55 was replicating in these cells as well. Although the frequency of positive bone marrow cells was low, the signal was very intense over individual positive cells. This result strongly suggests that S55 replicates in vivo in a subset of cells contained in the bone marrow.

EXAMPLE 11

Other Sindbis Group Viruses

It was of interest to determine if the ability to replicate in the bone marrow of mice was unique to S55 or was a general feature of other viruses, both Sindbis and non-Sindbis viruses, in the Sindbis group. Six 38-day-old female CD-1 mice were inoculated iv with 25 $\mu$l of diluent containing $10^3$ PFU of S55, Ockelbo82, Girdwood S.A., TR339, or TRSB. At 2, 4 and 6 days post-inoculation two mice from each group were sacrificed and whole blood, serun, brain (including brainstem), right quadricep, and both femurs were harvested for virus titration.

The results of this experiment were similar to those with S55. TRSB infected animals had no virus detectable in serum or whole blood in any animal at any time, and with the other viruses tested, no virus was detected in the serum or whole blood of any animal beyond two days post-inoculation (detection limit, 25 PFU/ml). Neither TRSB nor TR339 was detectable in the brains of infected animals at any time post-inoculation. S55, Girdwood S.A., and Ockelbo82 were present in the brains of infected animals sporadically with the titers being at or near the 75 PFU/g level of detection. All the tested viruses were found sporadically at or slightly above the 50 PFU/g detection limit in the right quadricep of infected animals except for a single animal four days post-inoculation with TRSB which had nearly 105 PFU/g of virus in its quadricep.

The frequency at which the different viruses were detected in bone marrow varied-widely with S55 and Girdwood S.A. being the most frequently isolated (five out of six animals) and Ockelbo82 and TRSB being the least frequently isolated from bone marrow (one out of six animals and two out of six animals, respectively) (Table 4). Girdwood S.A. and S55 gave nearly identical profiles in all tissues. Girdwood S.A., unlike S.A.AR86, is not neurovirulent in adult mice (Example 4), suggesting that the adult neurovirulence phenotype is distinct from the ability of the virus to replicate efficiently in bone marrow.

S51 differs from S55 by a threonine for isoleucine substitution at amino acid residue 538 of nsP1 and is attenuated in adult mice inoculated intracerebrally. Like S55, S51 targeted to and replicated in the bone marrow of 37-day-old female CD-1 mice following ic inoculation. Mice were inoculated ic with 500 PFU of S51 and sacrificed at 4, 8, 16, and 30 days post-inoculation for determination of bone marrow and serum titers. At no time post-inoculation was virus detected in the serum above the 6.25 PFU/ml detection limit. Virus was detectable in the bone marrow samples of both animals sampled at four day post-inoculation and in one animal eight days post-inoculation (Table 5). No virus was detectable by titration on BHK-21 cells in any of the bone marrow samples beyond eight days post-inoculation. These results suggested that the attenuating mutation present in S51, which reduces the neurovirulence of the virus, did not impair acute viral replication in the bone marrow.

It was notable that the plaque size on BHK-21 cells of virus recovered on day 4 post-inoculation was smaller than the size of plaques produced by the inoculum virus, and that plaques produced from virus recovered from the day 8

TABLE 4

Titers Following IV Inoculation of Virus

| Virus | Animal | Days Post-Inoculation | Bone Marrow (PFU/g) | Serum (PFU/ml) | Blood (PFU/ml) | Brain (PFU/g) | Quadricep (PFU/g) |
|---|---|---|---|---|---|---|---|
| S55 | A | 2 | 1125 | N.D.[a] | N.D. | N.D. | N.D. |
| | B | | 488 | 50 | 200 | N.D. | N.D. |
| | A | 4 | 863 | N.D. | N.D. | N.D. | 550 |
| | B | | 113 | N.D. | N.D. | 75 | N.D. |
| | A | 6 | N.D. | N.D. | N.D. | N.D. | 50 |
| | B | | 37.5 | N.D. | N.D. | N.D. | N.D. |
| | Limit of Detection | | 37.5 | 25 | 25 | 75 | 50 |
| TR339 | A | 2 | N.D. | N.D. | N.D. | N.D. | N.D. |
| | B | | 1500 | 75 | 700 | N.D. | ND |
| | A | 4 | 1050 | N.D. | N.D. | N.D. | N.D. |
| | B | | 1762 | N.D. | N.D. | N.D. | 400 |
| | A | 6 | N.D. | N.D. | N.D. | N.D. | N.D. |
| | B | | N.D. | N.D. | N.D. | N.D. | N.D. |
| | Limit of Detection | | 37.5 | 25 | 25 | 37.5 | 50 |
| TRSB | A | 2 | N.D. | N.D. | N.D. | N.D. | N.D. |
| | B | | N.D. | N.D. | N.D. | N.D. | N.D. |
| | A | 4 | 150 | N.D. | N.D. | N.D. | 1000 |
| | B | | N.D. | N.D. | N.D. | N.D. | 100000 |
| | A | 6 | N.D. | N.D. | N.D. | N.D. | N.D. |
| | B | | 37.5 | N.D. | N.D. | N.D. | N.D. |
| | Limit of Detection | | 37.5 | 25 | 25 | 37.5 | 50 |
| Girdwood S.A. | A | 2 | 22000 | 2325 | 1450 | 300 | 50 |
| | B | | 2500 | 1200 | 2600 | N.D. | N.D. |
| | A | 4 | 788 | N.D. | N.D. | N.D. | N.D. |
| | B | | 113 | N.D. | N.D. | 75 | N.D. |
| | A | 6 | N.D. | N.D. | N.D. | N.D. | N.D. |
| | B | | 75 | N.D. | N.D. | 1700 | N.D. |
| | Limit of Detection | | 37.5 | 25 | 25 | 75 | 50 |
| Ockelbo82 | A | 2 | N.D. | 125 | 150 | N.D. | N.D. |
| | B | | N.D. | 50 | 500 | N.D. | 200 |
| | A | 4 | N.D. | N.D. | N.D. | 300 | N.D. |
| | B | | 300 | N.D. | N.D. | N.D. | N.D. |
| | A | 6 | N.D. | N.D. | N.D. | 100000 | N.D. |
| | B | | N.D. | N.D. | N.D. | N.D. | N.D. |
| | Limit of Detection | | 37.5 | 25 | 25 | 75 | 50 |

[a]"N.D." indicates that the virus titers were below the limit of detection.

EXAMPLE 12

Virus Persistence in Bone Marrow

The next step in our investigations was to evaluate the possibility that S.A.AR86 persisted long-term in bone marrow. S51 is a molecularly cloned, attenuated mutant of S55.

post-inoculation samples were even smaller and barely visible. This suggests a strong selective pressure in the bone marrow for virus that is much less efficient in forming plaques on BHK-21 cells.

To demonstrate that S51 virus genomes were present in bone marrow cells long after acute infection, four to sixweek-old female CD-1 mice were inoculated ic with 500 PFU of S51. Three months post-inoculation two animals were sacrificed, perfused with paraformaldehyde and decalcified as described in Example 8. The heads and hind limbs from these animals were paraffin embedded, sectioned, and probed with a S.A.AR86 specific [$^{35}$S]-UTP labeled riboprobe derived from clone pDS45. In situ hybridization signal was clearly present in discrete cells of the bone and bone marrow of the legs (data not shown). Furthermore, no in situ hybridization signal was detected in an adjacent control section probed with an influenza virus HA gene specific riboprobe. As the relative sensitivity of in situ hybridization is reduced in decalcified tissues (Peter Charles, personal communication), these cells likely contain a relatively high number of viral sequences, even at three months post-inoculation. No in situ hybridization signal was observed in mid-sagital sections of the heads with the S.A.AR86 specific probe, although focal lesions were observed in the brain indicative of the prior acute infection with S51.

TABLE 5

S51 Titers in Bone Marrow Following IC Inoculation of 500 PFU

| Days Post-Inoculation | Titers (Total PFU/Animal) | | Limit of Detection |
|---|---|---|---|
| | Animal A | Animal B | |
| 4 | 2100 | 380 | 62.5 |
| 8 | 62.5 | N.D.[a] | 62.5 |
| 16 | N.D. | N.D. | 62.5 |
| 30 | N.D. | N.D. | 62.5 |

"N.D." indicates that the virus titers were below the limit of detection.

EXAMPLE 13

Replication of S.A.AR86 within Bone/Joint Tissue of Adult Mice

Several old world alphaviruses, including Ross River Virus, Chikungunya virus, Okelbo82, and S.A.AR86 are associated with acute and persistent arthritis/arthralgia in humans. Molecular clones of several Sindbis group viruses, including S.A.AR86, were used to investigate alphavirus replication within bone/joint tissue.

Following intravenous inoculation of S.A.AR86 into adult CD-1 mice, viral replication was observed in bone/joint tissue, but not surrounding muscle tissue of the hind limbs. Infectious virus was detectable 24 hrs post-infection; however, viral titer within bone/joint tissue was maximal 72 hours post-infection. Fractionation of hind limbs from infected animals revealed that the hip and knee joints were the predominant sites of viral replication. Replication within bone/joint tissue appears to be a common trait of Sindbis-group viruses, since the laboratory strains TR339 and TRSB also replicated within bone/joint tissue. In situ hybridization and S.A.AR86 based double promoter vectors expressing green fluorescent protein were used to further localize S.A.AR86 infected cells within bone/joint tissue. Green fluorescent protein expression was detected in bone/joint tissue for at least one month post-inoculation. These studies demonstrated that cells within the endosteum of synovial joints were the predominant site of S.AAR86 replication.

That which is claimed is:

1. A method of introducing and expressing heterologous RNA in bone marrow cells, comprising:

(a) providing a recombinant alphavirus, said alphavirus containing a replicon RNA comprising a heterologous RNA to be expressed in said bone marrow cells; and (b) contacting said recombinant alphavirus to said bone marrow cells so that said heterologous RNA is introduced and expressed therein.

2. The method of claim 1, wherein the structural proteins of said alphavirus are South African Arbovirus No. 86 (S.A.AR86) structural proteins.

3. The method of claim 1, wherein the structural proteins of said alphavirus are Girdwood S.A. structural proteins.

4. The method of claim 1, wherein the structural proteins of said alphavirus are TR339 structural proteins.

5. The method of claim 1, wherein the structural proteins of said alphavirus are Sindbis virus structural proteins.

6. A method of introducing and expressing heterologous RNA in bone marrow cells, comprising:
   (a) providing a recombinant South African Arbovirus No. 86 (S.A.AR86), said S.A.AR86 containing a heterologous RNA to be expressed in said bone marrow cells; and
   (b) contacting said recombinant S.A.AR86 to said bone marrow cells so that said heterologous RNA is introduced and expressed therein.

7. The method of claim 6, wherein said bone marrow cells are selected from the group consisting of polymorphonuclear cells, hematopoietic stem cells, erythrocytes, macrophages, fibroblasts, osteoprogenitor cells, osteoblasts, osteoclasts, marrow stromal cells, and chondrocytes.

8. The method of claim 7, wherein said bone marrow cells are osteoblasts.

9. The method of claim 6, wherein said bone marrow cells are in a synovial joint.

10. The method of claim 6, wherein said bone marrow cells are endosteum cells.

11. The method of claim 6, wherein said bone marrow cells are endosteum cells of a synovial joint.

12. The method of claim 11, wherein said bone marrow cells are osteoblasts.

13. The method according to claim 6, wherein said contacting step is carried out in vitro.

14. The method according to claim 13, further comprising the step of administering the bone marrow cells to a subject in need thereof.

15. The method according to claim 6, wherein said contacting step is carried out in vivo in a subject in need of such treatment.

16. The method according to claim 15, wherein said S.A.AR86 is administered by a parenteral route.

17. The method according to claim 16, wherein said S.A.AR86 is administered by a method selected from the group consisting of subcutaneous, intracerebral, intradermal, intramuscular, intravenous and intraarticular administration.

18. The method according to claim 6, wherein said heterologous RNA encodes a protein or peptide.

19. The method according to claim 18, wherein said heterologous RNA encodes an immunogenic protein or peptide.

20. The method according to claim 19, wherein said immunogenic protein or peptide is a viral antigen.

21. The method according to claim 20, wherein said immunogenic protein or peptide is selected from the group consisting of an influenza immunogen, an orthomyxovirus immunogen, a lentivirus immunogen, an equine infectious anemia virus immunogen, a simian immunodeficiency virus immunogen, a human immunodeficiency virus immunogen, a Lassa fever virus immunogen, an arenavirus immunogen, a vaccinia virus immunogen, a poxvirus immunogen, a yellow fever virus immunogen, a Japanese encephalitis virus immunogen, a flavivirus immunogen, an Ebola virus immunogen, a Marburg virus immunogen, a filovirus immunogen, a bunyavirus immunogen, a Rift Valley Fever immunogen, a Congo-Crimean hemorrhagic fever virus immunogen, a Sandfly fever Sicilian virus immunogen, and a coronavirus immunogen.

22. The method according to claim 20, wherein said immunogenic protein or peptide is a human immunodeficiency virus immunogen.

23. The method according to claim 19, wherein said S.A.AR86 virus contains a heterologous RNA segment, said heterologous RNA segment comprising a promoter operable in said bone marrow cells operatively associated with said heterologous RNA.

24. The method of claim 23, wherein said promoter is a S.A.AR86 26S promoter.

25. The method according to claim 18, wherein said heterologous RNA encodes a therapeutic protein or peptide.

26. The method according to claim 25, wherein said protein or peptide is selected from the group consisting of hormones, growth factors, interleukins, cytokines, chemokines, and enzymes.

27. The method according to claim 6, wherein said heterologous RNA encodes an antisense oligonucleotide or a ribozyme.

28. The method according to claim 6, wherein said S.A.AR86 contains a replicon RNA comprising the heterologous RNA.

29. The method of claim 6, wherein said S.A.AR86 comprises one or more attenuating mutations.

30. A method of introducing and expressing heterologous RNA in bone marrow cells, comprising:
   (a) providing a recombinant Girdwood S.A. virus, said Girdwood S.A. virus containing a heterologous RNA to be expressed in said bone marrow cells; and
   (b) contacting said recombinant Girdwood S.A. virus to said bone marrow cells so that said heterologous RNA is introduced and expressed therein.

31. The method of claim 30, wherein said bone marrow cells are selected from the group consisting of polymorphonuclear cells, hematopoietic stem cells, erythrocytes, macrophages, fibroblasts, osteoprogenitor cells, osteoblasts, osteoclasts, marrow stromal cells, and chondrocytes.

32. The method according to claim 30, wherein said contacting step is carried out in vitro.

33. The method according to claim 32, further comprising the step of administering the bone marrow cells to a subject in need thereof.

34. The method according to claim 30, wherein said heterologous RNA encodes an immunogenic protein or peptide.

35. The method according to claim 30, wherein said heterologous RNA encodes a therapeutic protein or peptide.

36. The method according to claim 30, wherein said heterologous RNA encodes an antisense oligonucleotide or a ribozyme.

37. The method according to claim 30, wherein said Girdwood S.A. contains a replicon RNA comprising the heterologous RNA.

38. A method of introducing and expressing heterologous RNA in bone marrow cells, comprising:
   (a) providing a recombinant Sindbis virus, said Sindbis virus containing a heterologous RNA to be expressed in said bone marrow cells; and
   (b) contacting said recombinant Sindbis virus to said bone marrow cells so that said heterologous RNA is introduced and expressed therein.

39. The method of claim 38, wherein said bone marrow cells are selected from the group consisting of polymorphonuclear cells, hematopoietic stem cells, erythrocytes, macrophages, fibroblasts, osteoprogenitor cells, osteoblasts, osteoclasts, marrow stromal cells, and chondrocytes.

40. The method according to claim 38, wherein said contacting step is carried out in vitro.

41. The method according to claim 40, further comprising the step of administering the bone marrow cells to a subject in need thereof.

42. The method according to claim 38, wherein said heterologous RNA encodes an immunogenic protein or peptide.

43. The method according to claim 38, wherein said heterologous RNA encodes a therapeutic protein or peptide.

44. The method according to claim 38, wherein said heterologous RNA encodes an antisense oligonucleotide or a ribozyme.

45. The method according to claim 38, wherein said Sindbis virus contains a replicon RNA comprising the heterologous RNA.

46. A method of introducing and expressing heterologous RNA in bone marrow cells, comprising:
   (a) providing a recombinant Sindbis strain TR339 virus, said Sindbis strain TR339 virus containing a heterologous RNA to be expressed in said bone marrow cells; and
   (b) contacting said recombinant Sindbis strain TR339 virus to said bone marrow cells so that said heterologous RNA is introduced and expressed therein.

47. The method of claim 46, wherein said bone marrow cells are selected from the group consisting of polymorphonuclear cells, hematopoietic stem cells, erythrocytes, macrophages, fibroblasts, osteoprogenitor cells, osteoblasts, osteoclasts, marrow stromal cells, and chondrocytes.

48. The method according to claim 46, wherein said contacting step is carried out in vitro.

49. The method according to claim 48, further comprising the step of administering the bone marrow cells to a subject in need thereof.

50. The method according to claim 46, wherein said heterologous RNA encodes an immunogenic protein or peptide.

51. The method according to claim 46, wherein said heterologous RNA encodes a therapeutic protein or peptide.

52. The method according to claim 46, wherein said heterologous RNA encodes an antisense oligonucleotide or a ribozyme.

53. The method according to claim 46, wherein said Sindbis strain TR339 virus contains a replicon RNA comprising the heterologous RNA.

* * * * *

UNITED STATES PATENT AND TRADEMARK OFFICE
CERTIFICATE OF CORRECTION

PATENT NO. : 6,583,121 B1
DATED : June 24, 2003
INVENTOR(S) : Johnston et al.

It is certified that error appears in the above-identified patent and that said Letters Patent is hereby corrected as shown below:

Title page,
Item [75], Inventor, the following should be added:
-- Mark T. Heise, Durham, NC --
Item [56], References Cited, OTHER PUBLICATIONS, should read -- L. Ye Bulychyov, et al. "Disease Course in Guinea Pigs After Aerogenous Infection With Venezuelan Equine Encephalomyelitis Virus," English Abstract attached. 1195. --.

Column 145,
Line 21, should read -- 11. The method of claim 10, wherein said bone marrow --

Signed and Sealed this

Fourth Day of May, 2004

JON W. DUDAS
*Acting Director of the United States Patent and Trademark Office*